(12) United States Patent
Heine et al.

(10) Patent No.: US 9,278,954 B2
(45) Date of Patent: Mar. 8, 2016

(54) PYRROLIDINE DERIVATIVES, PHARMACEUTICAL COMPOSITIONS AND USES THEREOF

(71) Applicants: Niklas Heine, Bicerach an der Riss (DE); Martin Fleck, Warthausen (DE); Bernd Nosse, Biberach an der Riss (DE); Gerald Juergen Roth, Biberach an der Riss (DE)

(72) Inventors: Niklas Heine, Bicerach an der Riss (DE); Martin Fleck, Warthausen (DE); Bernd Nosse, Biberach an der Riss (DE); Gerald Juergen Roth, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/275,873

(22) Filed: May 12, 2014

(65) Prior Publication Data
US 2014/0343083 A1 Nov. 20, 2014

(30) Foreign Application Priority Data

May 17, 2013 (EP) .................................... 13168294

(51) Int. Cl.
| | |
|---|---|
| C07D 403/04 | (2006.01) |
| C07D 207/12 | (2006.01) |
| C07D 401/04 | (2006.01) |
| C07D 413/14 | (2006.01) |
| C07D 403/14 | (2006.01) |
| C07D 417/14 | (2006.01) |

(52) U.S. Cl.
CPC ............ *C07D 403/04* (2013.01); *C07D 207/12* (2013.01); *C07D 401/04* (2013.01); *C07D 403/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| 6,313,127 B1 * | 11/2001 | Waterson et al. ........ 514/253.01 |
|---|---|---|
| 2011/0212939 A1 | 9/2011 | Bertram et al. |

FOREIGN PATENT DOCUMENTS

| WO | 9728128 A1 | 8/1997 |
|---|---|---|
| WO | 9731907 A1 | 9/1997 |
| WO | 2007009236 A1 | 1/2007 |
| WO | 2007134457 A1 | 11/2007 |
| WO | 2007143824 A1 | 12/2007 |
| WO | 2009054983 A1 | 4/2009 |
| WO | 2009054984 A1 | 4/2009 |
| WO | 2009105715 A1 | 8/2009 |
| WO | WO2009/131196 | * 10/2009 |
| WO | 2010004347 A1 | 1/2010 |
| WO | 2014056771 A1 | 4/2014 |

OTHER PUBLICATIONS

Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Abdel-Magid et al., Treatment of Obesity and Related Disorders with Acetyl-CoA Carboxylase Inhibitors. ACS Medicinal Chemistry Letters, 2013, 4, 16-17.*
CAPLUS printout of U.S. Pat. No. 6,313,127.*
International Search Report and Written Opinion for corresponding application PCT/EP2014/059537, date of mailing Sep. 1, 2014.

* cited by examiner

*Primary Examiner* — Michael Barker
*Assistant Examiner* — Po-Chih Chen
(74) *Attorney, Agent, or Firm* — Michael P. Morris; Alan R. Stempel

(57) ABSTRACT

Pyrrolidine derivatives which are inhibitors of acetyl-CoA carboxylase(s) and their use in the treatment of obesity and type-2 diabetes. An exemplary compound is 2-(4-(1-[5-Chloro-6-(2-hydroxy-2-methyl-propoxy)-pyrimidin-4-yl]-(R)-pyrrolidin-3-yloxy)-phenyl)-N-cyclopropyl-propionamide.

13 Claims, No Drawings

PYRROLIDINE DERIVATIVES, PHARMACEUTICAL COMPOSITIONS AND USES THEREOF

FIELD OF THE INVENTION

This invention relates to new compounds, in particular pyrrolidine derivatives, to processes for preparing such compounds, to their use as inhibitors of acetyl-CoA carboxylase(s), to methods for their therapeutic use, in particular in diseases and conditions mediated by the inhibition of acetyl-CoA carboxylase(s), and to pharmaceutical compositions comprising them.

BACKGROUND OF THE INVENTION

Obesity is a major public health issue not only for the EU, USA, Japan but also for the world in general. It is associated with a number of serious diseases including diabetes, dyslipidemia, hypertension, cardiovascular and cerebrovascular diseases. Although the underlying mechanisms are not yet fully understood, the impairement of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (Saggerson D. Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr. Journal of Cellular Biochemistry 99:1476-1488, 2006; Corbett J W, Harwood J H Jr., Recent Pat Cardiovasc Drug Discov. 2007 November; 2(3):162-80).

Furthermore recent data show that cellular toxicity mediated by lipids (lipotoxicity) is implicated in the susceptibitlity to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers Diabetes 2011; 60:306-14; P Ebeling, B Essén-Gustaysson, J A Tuominen and V A Koivisto Diabetologia 41: 111-115; K J Nadeau, J G Regensteiner, T A Bauer, M S Brown, J L Dorosz, A Hull, P Zeitler, B Draznin, J E B. Reusch J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26).

Furthermore in central nervous system disorders including but not limited to Alzheimer's disease, Parkinson disease and epilepsy, impairements in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (S T Henderson Neurotherapeutics, 2008, 5:470-480; L C Costantini, L J Barr, J L Vogel, S T Henderson BMC Neurosci. 2008, 9 Suppl 2:S16; K W Baranano, A L Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, A D, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Barahano, A L Hartman. Curr Treat Options Neurol. 2008; 10:410-9).

Furthermore, the potential of ACC inhibitors as antifungal agents and as antibacterial agents is well documented (L. Tong, H J Harwood Jr. Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (Munger J, B D Bennett, A Parikh, X J Feng, J McArdle, H A Rabitz, T Shenk, J D Rabinowitz. *Nat. Biotechnol.* 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

AIM OF THE PRESENT INVENTION

The aim of the present invention is to provide new compounds, in particular new pyrrolidine derivatives, which are active with regard to acetyl-CoA carboxylase(s).

Another aim of the present invention is to provide new compounds, in particular new pyrrolidine derivatives, which are active with regard to ACC2.

A further aim of the present invention is to provide new compounds, in particular new pyrrolidine derivatives, which have an inhibitory effect on acetyl-CoA carboxylase(s) in vitro and/or in vivo and possess suitable pharmacological and pharmacokinetic properties to use them as medicaments.

A further aim of the present invention is to provide new compounds, in particular new pyrrolidine derivatives, which have an inhibitory effect on ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular pyrrolidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to acetyl-CoA carboxylase(s).

According to another aspect of the present invention it has been found that the new compounds of general formula (I) as described hereinafter exhibit an inhibiting activity with regard to ACC2.

In a first aspect the present invention provides a compound of general formula $$(R^1)_n-Ar^1-N\underset{R^5}{\overset{O-Ar^2}{\bigcirc}}\underset{O}{\overset{R^2}{\bigvee}}N\underset{R^4}{\overset{R^3}{\bigvee}}\quad (I)$$

wherein $Ar^1$ is selected from the group $Ar^1$-G1 consisting of: phenylene and 6-membered heteroarylene containing 1, 2 or 3 nitrogen atoms, $R^1$ is selected from the group $R^1$-G1 consisting of:
halogen, CN, OH, —$NO_2$, $C_{1-6}$-alkyl, $C_{2-4}$-alkenyl, $C_{3-7}$-cycloalkyl, —($C_{1-3}$-alkyl)-($C_{3-7}$-cycloalkyl), —O—($C_{1-6}$-alkyl), —O—($C_{3-7}$-cycloalkyl), —O—($C_{1-3}$-alkyl)-($C_{3-7}$-cycloalkyl), —$NH_2$, heterocyclyl, —($C_{1-3}$-alkyl)-heterocyclyl, —O-(heterocyclyl), —O—($C_{1-3}$-alkyl)-(heterocyclyl), —O-phenyl and —O—($C_{1-3}$-alkyl)-phenyl, wherein each alkyl, cycloalkyl and heterocyclyl is optionally substituted with one or more substituents selected from F and OH;

wherein in the $NH_2$-group, one or both hydrogen atoms may independently of each other be replaced by a group selected from $C_{1-6}$-alkyl, $C_{3-7}$-cycloalkyl and —($C_{1-3}$-alkyl)-($C_{3-7}$-cycloalkyl), wherein said $C_{1-6}$-alkyl, $C_{3-7}$-cycloalkyl and —($C_{1-3}$-alkyl)-($C_{3-7}$-cycloalkyl) groups may each be substituted by one or more F or OH, wherein said substituents are the same or different; and wherein each heterocyclyl group is selected from a 4- to 7-membered monocyclic heterocyclic ring that contains 1, 2 or 3 heteroatoms independently selected from N, O and S and may be substituted with one or more substituents independently of each other selected from methyl, —$CF_3$, F and OH, wherein, if two methyl groups are attached to the same carbon atom of the heterocyclyl group, they may be connected to each other to form a spiro-cyclopropyl group;

or, if two $R^1$-groups are attached to adjacent C-atoms of $Ar^1$, they may be linked with each other and together form a $C_{3-5}$-alkylene bridging group in which 1, 2 or 3—$CH_2$—groups may independently of each be replaced by —O—, —C(=O)—, —S—, —S(=O)—, —S(=O)$_2$—, —NH— or —N($C_{1-4}$-alkyl)-, wherein the alkylene bridge may optionally be substituted by one or two $C_{1-3}$-alkyl groups;

n is 0, 1, 2 or 3;

$Ar^2$ is selected from the group $Ar^2$-G1 consisting of: phenylene and pyridinylene,
  which are each optionally substituted with one or more substituents independently of each other selected from F, Cl, —O—$CH_3$ and $CH_3$;

$R^2$ is selected from the group $R^2$-G1 consisting of: H and $C_{1-4}$-alkyl optionally substituted with 1-3 F;

$R^3$ is selected from the group $R^3$-G1 consisting of: H and $C_{1-4}$-alkyl;

$R^4$ is selected from the group $R^4$-G1 consisting of:
  H, $C_{1-6}$-alkyl, $C_{3-7}$-cycloalkyl, ($C_{3-7}$-cycloalkyl)-($C_{1-3}$-alkyl)-, $C_{3-6}$-alkenyl, $C_{3-6}$-alkynyl, heterocyclyl, heterocyclyl-($C_{1-3}$-alkyl)-, aryl, aryl-($C_{1-3}$-alkyl)-, 5- or 6-membered heteroaryl containing 1, 2 or 3 heteroatoms independently selected from N, O and S and (5-membered heteroaryl)-($C_{1-3}$-alkyl)-, wherein the heteroaryl moiety has 5 ring atoms and contains 1, 2 or 3 heteroatoms independently selected from N, O and S,
    wherein each cycloalkyl and heterocyclyl may be optionally substituted with one or more $C_{1-4}$-alkyl, and
    wherein in each cycloalkyl and heterocyclyl a —$CH_2$- group may optionally be replaced by —C(=O)—, and
    wherein each alkyl, cycloalkyl and heterocyclyl may be optionally substituted with one or more groups independently selected from the group consisting of: F, Cl, Br, CN, OH and optionally mono- or polyfluorated —O—($C_{1-4}$-alkyl), wherein the alkyl moiety of said —O—($C_{1-3}$-alkyl) group may be substituted by one or more F, and
    wherein each aryl and heteroaryl group may be optionally substituted with one or more substituents independently of each other selected from F, Cl, —O—$CH_3$, —O—$CF_3$, —O—$CHF_2$, $CH_3$ and —NH—C(=O)—($C_{1-3}$-alkyl);

or $R^3$ and $R^4$ are connected with each other and together with the N-atom to which they are attached form a group selected from the group $R^3R^4$N-G1 consisting of:
  azetidinyl, pyrrolidinyl, piperidinyl and azepanyl,
    wherein in each of these cyclic groups one or two $CH_2$- groups may independently of each other be replaced by N, O, S, C(=O) or $SO_2$, and/or
    wherein each of these groups may be substituted by one or more F or $C_{1-4}$-alkyl; and $R^5$ is selected from the group $R^5$-G1 consisting of H, F, Cl, CN and —O—($C_{1-3}$-alkyl), wherein the alkyl moiety of the —O—($C_{1-3}$-alkyl) group may be substituted by one or more F;

wherein each of the above-mentioned alkyl and —O-alkyl groups may be substituted by one or more F;

a tautomer or stereoisomers thereof,
  or a salt thereof,
  or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described hereinbefore and hereinafter.

According to another aspect of the invention, there is provided a compound of the general formula (I) or a pharmaceutically acceptable salt thereof for a therapeutic method as described hereinbefore and hereinafter.

In a further aspect this invention relates to a method for treating a disease or condition mediated by the inhibition of acetyl-CoA carboxylase(s) in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of acetyl-CoA carboxylase(s).

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $Ar^1$, $Ar^2$, $R^1$, $R^2$, $R^3$, $R^4$, $R^5$ and n, are defined as above and hereinafter. If residues, substituents or groups occur several times in a compound, as for example $R^1$, they may have the same or different meanings. Some preferred meanings of individual groups and substituents of the compounds according to the invention will be given hereinafter. Any and each of these definitions may be combined with each other.

$Ar^1$:

$Ar^1$-G1:

The group $Ar^1$ is preferably selected from the group $Ar^1$-G1 as defined hereinbefore and hereinafter.

$Ar^1$-G2:

In another embodiment the group $Ar^1$ is selected from the group $Ar^1$-G2 consisting of: phenylene or a 6-membered heteroarylene group containing 1 or 2 nitrogen atoms.

$Ar^1$-G3:

In another embodiment the group $Ar^1$ is selected from the group $Ar^1$-G3 consisting of: phenylene, pyridinylene and pyrimidinylene.

$Ar^1$-G4:

In another embodiment the group $Ar^1$ is selected from the group $Ar^1$-G4 consisting of:

$Ar^1$-G5:

In another embodiment the group $Ar^1$ is selected from the group $Ar^1$-G5 consisting of:

$Ar^1$-G6:

In another embodiment the group $Ar^1$ is selected from the group $Ar^1$-G6 consisting of:

According to a preferred embodiment, $Ar^1$ is phenylene.

According to another preferred embodiment, $Ar^1$ is pyridin-2-yl.

According to another preferred embodiment, $Ar^1$ is pyridin-4-yl.

According to another preferred embodiment, $Ar^1$ is pyrimidin-4-yl.

$R^1$:

$R^1$-G1:

The group $R^1$ is preferably selected from the group $R^1$-G1 as defined hereinbefore and hereinafter.

$R^1$-G2:

In another embodiment the group $R^1$ is independently of one another selected from the group $R^1$-G2 consisting of:

F, Cl, Br, CN, OH, $C_{1-4}$-alkyl, $C_{3-7}$-cycloalkyl, —O—($C_{1-6}$-alkyl), —O—($C_{3-7}$-cycloalkyl), —O—($C_{1-3}$-alkyl)-($C_{3-7}$-cycloalkyl), —NH$_2$, heterocyclyl, —O—($C_{1-3}$-alkyl)-(heterocyclyl), —O-phenyl and —O—($CH_{1-2}$-phenyl, wherein each alkyl, cycloalkyl and heterocyclyl is optionally substituted with one or more substituents selected from F and OH;

wherein in the NH$_2$-group, one or both hydrogen atoms may independently of each other be replaced by a group selected from $C_{1-6}$-alkyl and $C_{3-7}$-cycloalkyl, wherein said $C_{1-6}$-alkyl and $C_{3-7}$ cycloalkyl groups may each be substituted by one or more F or OH, wherein said substituents are the same or different; and wherein each heterocyclyl group is selected from tetrahydrofuranyl, tetrahydropyranyl, pyrrolidinyl, piperidinyl, piperazinyl and morpholinyl and may be substituted with one or more F or OH;

or, if two $R^1$-groups are attached to adjacent C-atoms of $Ar^1$, they may be linked with each other and together form a $C_{3-5}$-alkylene bridging group in which 1, 2 or 3 —CH$_2$— groups may independently of each be replaced by —O—, —C(=O)—, —S—, —NH— or —N($C_{1-4}$-alkyl)-, wherein the alkylene bridge may optionally be substituted by one or two $C_{1-3}$-alkyl groups.

$R^1$-G3:

In another embodiment the group $R^1$ is selected from the group $R^1$-G3 consisting of: F, Cl, Br, CN, OH, $C_{1-3}$-alkyl, $C_{3-5}$-cycloalkyl, —O—($C_{1-6}$-alkyl), —O—($C_{3-7}$-cycloalkyl), —O—($C_{1-3}$-alkyl)-($C_{3-5}$-cycloalkyl), —NH$_2$, heterocyclyl, —O-phenyl and —O—($CH_2$)$_{1-2}$-phenyl, wherein each alkyl, cycloalkyl and heterocyclyl is optionally substituted with one or more substituents selected from F and OH;

wherein in the NH$_2$-group, one or both hydrogen atoms may independently of each other be replaced by a group selected from $C_{1-4}$-alkyl and $C_{3-5}$-cycloalkyl; and wherein each heterocyclyl group is selected from pyrrolidinyl, piperidinyl, piperazinyl and morpholinyl and may be substituted with one or more F or OH;

or, if two $R^1$-groups are attached to adjacent C-atoms of $Ar^1$, they may be linked with each other and together form a $C_{3-5}$-alkylene bridging group in which 1 or 2-CH$_2$— groups may independently of each be replaced by —O—, —NH— or —N($C_{1-4}$-alkyl)-, wherein the alkylene bridge may optionally be substituted by one or two methyl groups.

$R^1$-G4:

In another embodiment the group $R^1$ is selected from the group $R^1$-G4 consisting of: F, Cl, Br, CN, OH, $C_{1-3}$-alkyl, $C_{3-5}$-cycloalkyl, —O—($C_{1-6}$-alkyl), —O—($C_{3-7}$-cycloalkyl), —O—($C_{1-3}$-alkyl)-($C_{3-5}$-cycloalkyl), —NH$_2$, heterocyclyl, —O-phenyl and —O—($CH_2$)$_{1-2}$-phenyl, wherein each alkyl, cycloalkyl and heterocyclyl is optionally substituted with one or more substituents selected from F and OH;

wherein in the NH$_2$-group, one or both hydrogen atoms may independently of each other be replaced by a group selected from $C_{1-4}$-alkyl and $C_{3-5}$-cycloalkyl; and wherein each heterocyclyl group is selected from pyrrolidinyl and morpholinyl and may be substituted with one or two F or OH;

or, if two $R^1$-groups are attached to adjacent C-atoms of $Ar^1$, they may be linked with each other and together form a —O—CH$_2$—CH$_2$—CH$_2$—O— group.

$R^1$-G4a:

In another embodiment the group $R^1$ is selected from the group $R^1$-G4a consisting of: F, Cl, Br, CN, OH, $C_{1-3}$-alkyl, $C_{3-5}$-cycloalkyl, —O—($C_{1-6}$-alkyl), —O—($C_{3-7}$-cycloalkyl), —O—(C$_{1-3}$-alkyl)-(C$_{3-5}$-cycloalkyl), —NH$_2$, heterocyclyl, —O-phenyl and —O—(CH$_2$)$_{1-2}$-phenyl,
wherein each alkyl, cycloalkyl and heterocyclyl is optionally substituted with one or more substituents selected from F and OH;
wherein in the NH$_2$-group, one or both hydrogen atoms may independently of each other be replaced by a group selected from C$_{1-4}$-alkyl and C$_{3-5}$-cycloalkyl; and
wherein each heterocyclyl group is selected from pyrrolidinyl and morpholinyl and may be substituted with one or two F or OH;
or, if two R$^1$-groups are attached to adjacent C-atoms of Ar$^1$, they may be linked with each other and together form a —O—OH$_2$—OH$_2$—OH$_2$—O— group;
or, if n is 2, the second R$^1$ group is selected from the group consisting of F, Cl, CN, and CH$_3$.
Preferably, n is 1 or 2.

R$^1$-G5:
In another embodiment the group R$^1$ is selected from the group R$^1$-G5 consisting of: F, Cl, CF$_3$, —O—(C$_{1-5}$-alkyl), —O—(C$_{3-7}$-cycloalkyl), —O—OH$_2$—(C$_{3-5}$-cycloalkyl) and —NH$_2$,
wherein each alkyl and cycloalkyl is optionally substituted with one or more substituents selected from F and OH;
wherein in the NH$_2$-group, one or both hydrogen atoms may independently of each other be replaced by C$_{1-4}$-alkyl.

R$^1$-G5a:
In another embodiment the group R$^1$ is selected from the group R$^1$-G5a consisting of: CF$_3$, —O—(C$_{1-5}$-alkyl), —O—(C$_{3-7}$-cycloalkyl), —O—CH$_2$—(C$_{3-5}$-cycloalkyl) and —NH$_2$,
wherein each alkyl and cycloalkyl is optionally substituted with one or more substituents selected from F and OH;
wherein in the NH$_2$-group, one or both hydrogen atoms may independently of each other be replaced by C$_{1-4}$-alkyl;
or, if n is 2, the second R$^1$ group is selected from the group consisting of F and Cl.
Preferably, n is 1 or 2.

R$^1$-G6:
In another embodiment the group R$^1$ is selected from the group R$^1$-G6 consisting of: F, Cl, Br, CN, C$_{1-3}$-alkyl, cyclopropyl, —O—(C$_{1-5}$-alkyl), —O—(C$_{3-7}$-cycloalkyl), —O—(C$_{1-3}$-alkyl)-(C$_{3-5}$-cycloalkyl), —O-phenyl, pyrrolidinyl, morpholinyl, —O-benzyl, and —NR$^{N1}$R$^{N2}$,
wherein R$^{N1}$ is H or C$_{1-2}$-alkyl, and
R$^{N2}$ is C$_{1-5}$-alkyl or C$_{3-5}$-cycloalkyl,
wherein each alkyl is linear or branched, and
wherein the pyrrolidinyl group and each alkyl and cycloalkyl group are optionally substituted with 1 to 3 F or with one OH.

R$^1$-G6a:
In another embodiment the group R$^1$ is selected from the group R$^1$-G6a consisting of: F, Cl, CF$_3$, -continued R$^1$-G6b:
In another embodiment the group R$^1$ is selected from the group R$^1$-G6b consisting of: CF$_3$, or, if n is 2, the second R$^1$ group is selected from the group consisting of F and Cl.
Preferably, n is 1 or 2.

n
n is 0, 1, 2 or 3.
Preferably, n is 1, 2 or 3.
More preferably, n is 1 or 2.
In one embodiment, n is 2.
In another embodiment, n is 1.
Preferred Groups for the (R$^1$)$_n$—Ar$^1$— Moiety include, but are not Limited to:

More Preferred Groups for the $(R^1)_n$—$Ar^1$— Moiety include, but are not Limited to:

$Ar^2$

$Ar^2$-G1:

The group $Ar^2$ is preferably selected from the group $Ar^2$-G1 as defined hereinbefore and hereinafter.

$Ar^2$-G2:

In another embodiment the group $Ar^2$ is selected from the group $Ar^2$-G2 consisting of: phenylene, which is optionally substituted with F.

$Ar^2$-G3:

In another embodiment the group $Ar^2$ is selected from the group $Ar^2$-G3 consisting of: phenylene, which is optionally monosubstituted with F.

$Ar^2$-G4:

In another embodiment the group $Ar^2$ is selected from the group $Ar^2$-G4 consisting of:

13

[chemical structure: 1,4-phenylene with two attachment points]

R²
R²-G1:
  The group R² is preferably selected from the group R²-G1 as defined hereinbefore and hereinafter.
R²-G2:
  In another embodiment the group R² is selected from the group R²-G2 consisting of: H and $C_{1-2}$-alkyl.
R²-G3:
  In another embodiment, the group R² is selected from the group R²-G3 consisting of $CH_3$.
R³:
R³-G1:
  The group R³ is preferably selected from the group R³-G1 as defined hereinbefore and hereinafter.
R³-G2:
  In one embodiment the group R³ is selected from the group R³-G2 consisting of H and $C_{1-2}$-alkyl.
R³-G3:
  In another embodiment the group R³ is selected from the group R³-G3 consisting of H and $CH_3$.
R³-G4:
  In another embodiment the group R³ is selected from the group R³-G4 consisting of H.
R⁴:
R⁴-G1:
  The group R⁴ is preferably selected from the group R⁴-G1 as defined hereinbefore and hereinafter.
R⁴-G2:
  In one embodiment the group R⁴ is selected from the group R⁴-G2 consisting of: H, $C_{1-5}$-alkyl, $C_{3-5}$-cycloalkyl, ($C_{3-5}$-cycloalkyl)-$CH_2$—, $C_{3-5}$-alkenyl, $C_{3-5}$-alkynyl, heterocyclyl, heterocyclyl-($C_{1-3}$-alkyl)-, phenyl, 6-membered heteroaryl containing 1 or 2 N atoms and thiazolyl-$CH_2$—,
    wherein the heterocyclyl group is selected from the group consisting of oxetanyl, tetrahydrofuranyl and tetrahydropyranyl, and
    wherein each cycloalkyl may be optionally substituted with one or two $CH_3$, and
    wherein each alkyl and cycloalkyl may be optionally substituted with one or more groups independently selected from the group consisting of: F, Cl, ON, OH, —O—$CHF_2$, —O—$CF_3$ and —O—$CH_3$, and
    wherein the phenyl, thiazolyl and 6-membered heteroaryl groups may each be optionally substituted with one or two substituents independently of each other selected from F, Cl and —NH—C(=O)—$CH_3$.
R⁴-G3:
  In another embodiment the group R⁴ is selected from the group R⁴-G3 consisting of:
H;
$C_{1-5}$-alkyl optionally substituted with one to three F and/or one CN or OH;
$C_{3-5}$-cycloalkyl optionally substituted with one $CH_3$, wherein said $CH_3$-group may be substituted with one to three F;
($C_{3-5}$-cycloalkyl)-$CH_2$— optionally substituted in the cycloalkyl moiety with one or two F;
$C_{3-5}$-alkenyl;
$C_{3-5}$-alkynyl;
oxetanyl, tetrahydrofuranyl, tetrahydropyranyl;
oxetanyl-$CH_2$—;
phenyl optionally substituted with F;

14 pyridinyl, pyrimidinyl and
thiazolyl-$CH_2$— optionally substituted with —NH—C(=O)—$CH_3$.
R⁴-G4:
  In another embodiment the group R⁴ is selected from the group R⁴-G4 consisting of:

[chemical structures showing various R⁴ groups including: H, $CH_3$, ethyl, fluoroethyl, difluoroethyl, trifluoroethyl, isopropyl with CN, propyl variants with CH3, cyano-isopropyl, hydroxy-isopropyl variants, hydroxypropyl, hydroxyisobutyl, cyclopropyl, methylcyclopropyl, cyclobutyl, cyclopropylmethyl, cyclobutylmethyl, difluorocyclobutyl, allyl, butenyl, methallyl, propargyl, butynyl, oxetanyl, tetrahydropyranyl, oxetanylmethyl, fluorophenyl, pyridinyl, pyrimidinyl, and acetamido-thiazolylmethyl]

R⁴-G5:
  In another embodiment the group R⁴ is selected from the group R⁴-G5 consisting of:
ethyl optionally substituted with 1-3 F,
cyclopropyl optionally substituted with methyl and
propyn-3-yl.
R⁴-G5a:
  In another embodiment the group R⁴ is selected from the group R⁴-G5a consisting of: ethyl, —$CH_2$—$CHF_2$, cyclopropyl and

[Structure: cyclopropyl with CH3 substituent, attachment point *]

[Structure: azetidinyl ring with N attached via * and F substituent]

$R^3R^4N$:
$R^3R^4N$-G1:
The groups $R^3$ and $R^4$ may be connected with each other and together with the N-atom to which they are attached form a group that is preferably selected from the group $R^3R^4N$-G1 as defined hereinbefore and hereinafter.
$R^3R^4N$-G2:
In one embodiment the groups $R^3$ and $R^4$ may be connected with each other and together with the N-atom to which they are attached form a group selected from the group $R^3R^4N$-G2 consisting of:
  azetidinyl, pyrrolidinyl and piperidinyl,
  wherein each of these groups may be substituted by one or more F or $CH_3$.
$R^3R^4N$-G3:
In another embodiment the groups $R^3$ and $R^4$ may be connected with each other and together with the N-atom to which they are attached form a group selected from the group $R^3R^4N$-G3 consisting of:

$R^5$:
$R^5$-G1:
The group $R^5$ is preferably selected from the group $R^5$-G1 as defined hereinbefore and hereinafter.
$R^5$-G2:
In one embodiment the group $R^5$ is selected from the group $R^5$-G2 consisting of H, F, Cl, CN, —O—$CF_3$, —O—$CHF_2$ and —O—$CH_3$.
$R^5$-G3:
In another embodiment the group $R^5$ is selected from the group $R^5$-G3 consisting of H and F.
$R^5$-G4:
In another embodiment the group $R^5$ is selected from the group $R^5$-G4 consisting of H.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| Embodiment | $R^1$ | $Ar^1$ | $Ar^2$ | $R^2$ | $R^5$ | $R^3, R^4$ | n |
|---|---|---|---|---|---|---|---|
| E-1 | $R^1$-G1 | $Ar^1$-G1 | $Ar^2$-G1 | $R^2$-G1 | $R^5$-G1 | $R^3$-G1 and $R^4$-G1 or $R^3R^4N$-G1 | 0, 1, 2 or 3 |
| E-2 | $R^1$-G2 | $Ar^1$-G2 | $Ar^2$-G2 | $R^2$-G2 | $R^5$-G3 | $R^3$-G2 and $R^4$-G2 or $R^3R^4N$-G2 | 1, 2 or 3 |
| E-3 | $R^1$-G3 | $Ar^1$-G3 | $Ar^2$-G4 | $R^2$-G3 | $R^5$-G3 | $R^3$-G3 and $R^4$-G3 or $R^3R^4N$-G3 | 1, 2 or 3 |
| E-4 | $R^1$-G4a | $Ar^1$-G3 | $Ar^2$-G4 | $R^2$-G3 | $R^5$-G4 | $R^3$-G3 and $R^4$-G3 or $R^3R^4N$-G3 | 1, 2 or 3 |
| E-5 | $R^1$-G4a | $Ar^1$-G3 | $Ar^2$-G4 | $R^2$-G3 | $R^5$-G4 | $R^3$-G4 and $R^4$-G4 or $R^3R^4N$-G3 | 1 or 2 |
| E-6 | $R^1$-G6 | $Ar^1$-G3 | $Ar^2$-G4 | $R^2$-G3 | $R^5$-G4 | $R^3$-G4 and $R^4$-G5a or $R^3R^4N$-G3 | 1 or 2 |
| E-7 | $R^1$-G6b | $Ar^1$-G3 | $Ar^2$-G4 | $R^2$-G3 | $R^5$-G4 | $R^3$-G4 and $R^4$-G5a or $R^3R^4N$-G3 | 1 or 2 |
| E-8 | $R^1$-G3 | $Ar^1$-G5 | $Ar^2$-G4 | $R^2$-G3 | $R^5$-G4 | $R^3$-G3 and $R^4$-G3 or $R^3R^4N$-G3 | 1 or 2 |
| E-9 | $R^1$-G4a | $Ar^1$-G5 | $Ar^2$-G4 | $R^2$-G3 | $R^5$-G4 | $R^3$-G3 and $R^4$-G3 or $R^3R^4N$-G3 | 1 or 2 |
| E-10 | $R^1$-G4a | $Ar^1$-G5 | $Ar^2$-G4 | $R^2$-G3 | $R^5$-G4 | $R^3$-G4 and $R^4$-G4 or $R^3R^4N$-G3 | 1 or 2 |
| E-11 | $R^1$-G6 | $Ar^1$-G5 | $Ar^2$-G4 | $R^2$-G3 | $R^5$-G4 | $R^3$-G4 and $R^4$-G5a or $R^3R^4N$-G3 | 1 or 2 |
| E-12 | $R^1$-G6b | $Ar^1$-G5 | $Ar^2$-G4 | $R^2$-G3 | $R^5$-G4 | $R^3$-G4 and $R^4$-G5a | 1 or 2 |
| E-13 | $R^1$-G3 | $Ar^1$-G6 | $Ar^2$-G4 | $R^2$-G3 | $R^5$-G4 | $R^3$-G3 and $R^4$-G3 or $R^3R^4N$-G3 | 1 or 2 |
| E-14 | $R^1$-G4a | $Ar^1$-G6 | $Ar^2$-G4 | $R^2$-G3 | $R^5$-G4 | $R^3$-G3 and $R^4$-G3 or $R^3R^4N$-G3 | 1 or 2 |
| E-15 | $R^1$-G4a | $Ar^1$-G6 | $Ar^2$-G4 | $R^2$-G3 | $R^5$-G4 | $R^3$-G4 and $R^4$-G4 or $R^3R^4N$-G3 | 1 or 2 |

| Embodiment | R¹ | Ar¹ | Ar² | R² | R⁵ | R³, R⁴ | n |
|---|---|---|---|---|---|---|---|
| E-16 | R¹-G6 | Ar¹-G6 | Ar²-G4 | R²-G3 | R⁵-G4 | R³-G4 and R⁴-G5a or R³R⁴N-G3 | 1 or 2 |
| E-17 | R¹-G6b | Ar¹-G6 | Ar²-G4 | R²-G3 | R⁵-G4 | R³-G4 and R⁴-G5a | 1 or 2 |

The following preferred embodiments of compounds of the formula (I) are described using generic formulae (I.1) to (I.11b), wherein any tautomers and stereoisomers, solvates, hydrates and salts thereof, in particular the pharmaceutically acceptable salts thereof, are encompassed.

-continued (I.5a)

(I.5b)

(I.6)

(I.6a)

(I.6b)

(I.7)

(I.7a)

(I.7b)

-continued (I.8)

(I.8a)

(I.8b)

(I.9)

(I.9a)

(I.9b)

(I.10)

(I.10a)

-continued (I.10b)

(I.11)

(I.11a)

(I.11b)

wherein in each of the above formulae (I.1) to (I.11b), the groups Ar$^1$, R$^1$, R$^2$, R$^3$, R$^4$, R$^5$ and n are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | Formula | R$^1$ | Ar$^1$ | R$^2$ | R$^5$ | R$^3$, R$^4$ | n |
|---|---|---|---|---|---|---|---|
| E-18 | (I.4) | R$^1$-G4a | — | — | — | R$^3$-G3 and R$^4$-G3 or R$^3$R$^4$N-G3 | 1 or 2 |
| E-19 | (I.4) | R$^1$-G6 | — | — | — | R$^3$-G4 and R$^4$-G4 or R$^3$R$^4$N-G3 | 1 or 2 |
| E-20 | (I.4) | R$^1$-G6b | — | — | — | R$^3$-G4 and R$^4$-G5a or R$^3$R$^4$N-G3 | 1 or 2 |
| E-21 | (I.5) | R$^1$-G4a | — | — | — | R$^3$-G3 and R$^4$-G3 or R$^3$R$^4$N-G3 | 1 or 2 |
| E-22 | (I.5) | R$^1$-G6 | — | — | — | R$^3$-G4 and R$^4$-G4 or R$^3$R$^4$N-G3 | 1 or 2 |
| E-23 | (I.5) | R$^1$-G6b | — | — | — | R$^3$-G4 and R$^4$-G5a or R$^3$R$^4$N-G3 | 1 or 2 |
| E-24 | (I.6) | R$^1$-G4a | — | — | — | R$^3$-G3 and R$^4$-G3 or R$^3$R$^4$N-G3 | 1 or 2 |
| E-25 | (I.6) | R$^1$-G6 | — | — | — | R$^3$-G4 and R$^4$-G4 or R$^3$R$^4$N-G3 | 1 or 2 |
| E-26 | (I.6) | R$^1$-G6b | — | — | — | R$^3$-G4 and R$^4$-G5a or R$^3$R$^4$N-G3 | 1 or 2 |
| E-27 | (I.7) | R$^1$-G4a | — | — | — | R$^3$-G3 and R$^4$-G3 or R$^3$R$^4$N-G3 | 1 or 2 |
| E-28 | (I.7) | R$^1$-G6 | — | — | — | R$^3$-G4 and R$^4$-G4 or R$^3$R$^4$N-G3 | 1 or 2 |
| E-29 | (I.7) | R$^1$-G6b | — | — | — | R$^3$-G4 and R$^4$-G5a or R$^3$R$^4$N-G3 | 1 or 2 |
| E-30 | (I.8) | R$^1$-G4a | — | — | — | R$^3$-G3 and R$^4$-G3 or R$^3$R$^4$N-G3 | 1 or 2 |
| E-31 | (I.8) | R$^1$-G6 | — | — | — | R$^3$-G4 and R$^4$-G4 or R$^3$R$^4$N-G3 | 1 or 2 |
| E-32 | (I.8) | R$^1$-G6b | — | — | — | R$^3$-G4 and R$^4$-G5a or R$^3$R$^4$N-G3 | 1 or 2 |
| E-33 | (I.9) | R$^1$-G4a | — | — | — | R$^3$-G3 and R$^4$-G3 or R$^3$R$^4$N-G3 | 1 or 2 |
| E-34 | (I.9) | R$^1$-G6 | — | — | — | R$^3$-G4 and R$^4$-G4 or R$^3$R$^4$N-G3 | 1 or 2 |
| E-35 | (I.9) | R$^1$-G6b | — | — | — | R$^3$-G4 and R$^4$-G5a or R$^3$R$^4$N-G3 | 1 or 2 |
| E-36 | (I.10) | R$^1$-G4a | — | — | — | R$^3$-G3 and R$^4$-G3 or R$^3$R$^4$N-G3 | 1 or 2 |
| E-37 | (I.10) | R$^1$-G6 | — | — | — | R$^3$-G4 and R$^4$-G4 or R$^3$R$^4$N-G3 | 1 or 2 |
| E-38 | (I.10) | R$^1$-G6b | — | — | — | R$^3$-G4 and R$^4$-G5a or R$^3$R$^4$N-G3 | 1 or 2 |
| E-39 | (I.11) | R$^1$-G4a | — | — | — | R$^3$-G3 and R$^4$-G3 or R$^3$R$^4$N-G3 | 1 or 2 |
| E-40 | (I.11) | R$^1$-G6 | — | — | — | R$^3$-G4 and R$^4$-G4 or R$^3$R$^4$N-G3 | 1 or 2 |
| E-41 | (I.11) | R$^1$-G6b | — | — | — | R$^3$-G4 and R$^4$-G5a or R$^3$R$^4$N-G3 | 1 or 2 |

A preferred embodiment of the present invention concerns compounds of general formula (I.2)

wherein
n is 1 or 2;
Ar$^1$ is selected from the group consisting of:

R$^1$ is selected from the group consisting of F, Cl, Br, CN, OH, C$_{1-3}$-alkyl, C$_{3-5}$-cycloalkyl, —O—(C$_{1-6}$-alkyl), —O—(C$_{3-7}$-cycloalkyl), —O—(C$_{1-3}$-alkyl)-(C$_{3-5}$-cycloalkyl), —NH$_2$, heterocyclyl, —O-phenyl and —O—(CH$_2$)$_{1-2}$-phenyl,
   wherein each alkyl, cycloalkyl and heterocyclyl is optionally substituted with one or more substituents selected from F and OH;
   wherein in the NH$_2$-group, one or both hydrogen atoms may independently of each other be replaced by a group selected from C$_{1-4}$-alkyl and C$_{3-5}$-cycloalkyl; and
   wherein each heterocyclyl group is selected from pyrrolidinyl and morpholinyl and may be substituted with one or two F or OH;
or, if two R$^1$-groups are attached to adjacent C-atoms of Ar$^1$, they may be linked with each other and together form a —O—CH$_2$—CH$_2$—CH$_2$—O— group;

or, if n is 2, the second R¹ group is selected from the group consisting of F, Cl, CN, and CH$_3$;

R$^3$ is H or CH$_3$; and

R$^4$ is selected from the group consisting of:

H;

C$_{1-5}$-alkyl optionally substituted with one to three F and/or one CN or OH;

C$_{3-5}$-cycloalkyl optionally substituted with one CH$_3$, wherein said CH$_3$-group may be substituted with one to three F;

(C$_{3-5}$-cycloalkyl)-CH$_2$— optionally substituted in the cycloalkyl moiety with one or two F;

C$_{3-5}$-alkenyl;

C$_{3-5}$-alkynyl;

oxetanyl, tetrahydrofuranyl, tetrahydropyranyl;

oxetanyl-CH$_2$—;

phenyl optionally substituted with F;

pyridinyl, pyrimidinyl and thiazolyl-CH$_2$— optionally substituted with —NH—C(=O)—CH$_3$;

or R$^3$ and R$^4$ are connected with each other and together with the N-atom to which they are attached form the group

[structure: *—N(azetidine)—F];

or a salt thereof.

Another preferred embodiment of the present invention concerns compounds of general formula (I.3)

[structure showing (R¹)$_n$—Ar¹—N(pyrrolidine)—O—phenyl—CH(CH$_3$)—C(=O)—N(H)(R$^4$)]

wherein the (R¹)$_n$—Ar¹— moiety is selected from a group consisting of:

[structures showing various aryl groups with CF$_3$, F, Cl, O-alkyl, O-cyclobutyl, O-cyclopentyl substituents]

[continued structures: pyridinyl-O-CH$_2$-difluorocyclopropyl; pyridinyl-O-cyclopentyl with F; fluoropyridinyl-NH-ethyl; pyridinyl-O-butyl; pyrimidinyl-N(CH$_3$)(CH$_2$CH$_3$); pyrimidinyl-N(CH$_3$)(CH$_2$CH$_2$CH$_3$); pyrimidinyl-N(CH$_2$CH$_3$)$_2$; fluoropyrimidinyl-N(CH$_3$)$_2$; fluoropyrimidinyl-O-CH$_2$-C(CH$_3$)(F)(F); fluoropyrimidinyl-O-CH$_2$-C(OH)(CH$_3$)$_2$; and chloropyrimidinyl-O-CH$_2$-C(OH)(CH$_3$)$_2$]

and

R$^4$ is selected from the group consisting of:

ethyl, —CH$_2$—CHF$_2$, cyclopropyl and

[structure: methylcyclopropyl];

or a pharmaceutically acceptable salt thereof.

Preferred compounds of the invention include:

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably, the compounds are obtained analogously to the methods of preparation explained more fully hereinafter, in particular as described in the experimental section.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of acetyl-CoA carboxylase(s) (ACC) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

wherein the carboxy group is attached to the third carbon atom of the propyl group. The terms "1-methylpropyl-", "2,2-dimethylpropyl-" or "cyclopropylmethyl-" group represent the following groups:

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $-(CH_2)-$, $-(CH_2-CH_2)-$, $-(CH(CH_3))-$, $-(CH_2-CH_2-CH_2)-$, $-(C(CH_3)_2)-$, $-(CH(CH_2CH_3))-$, $-(CH(CH_3)-CH_2)-$, $-(CH_2-CH(CH_3))-$, $-(CH_2-CH_2-CH_2-CH_2)-$, $-(CH_2-CH_2-CH(CH_3))-$, $-(CH(CH_3)-CH_2-CH_2)-$, $-(CH_2-CH(CH_3)-CH_2)-$, $-(CH_2-C(CH_3)_2)-$, $-(C(CH_3)_2-CH_2)-$, $-(CH(CH_3)-CH(CH_3))-$, $-(CH_2-CH(CH_2CH_3))-$, $-(CH(CH_2CH_3)-CH_2)-$, $-(CH(CH_2CH_2CH_3))-$, $-(CHCH(CH_3)_2)-$ and $-C(CH_3)(CH_2CH_3)-$.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes $-CH=CH_2$, $-CH=CH-CH_3$, $-CH_2-CH=CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes $-CH=CH-$, $-CH=CH-CH_2-$, $-CH_2-CH=CH-$.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes $-C\equiv CH$, $-C\equiv C-CH_3$, $-CH_2-C\equiv CH$.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes $-C\equiv C-$, $-C\equiv C-CH_2-$, $-CH_2-C\equiv C-$.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cylcoalkyl, $C_{3-10}$-cycloalkenyl, octahydro-pentalenyl, octahydroindenyl, decahydronaphthyl, indanyl, tetrahydronaphthyl. Most preferably, the term $C_{3-n}$-carbocyclyl denotes $C_{3-n}$-cylcoalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably, the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O), with r=0, 1 or 2, which in addition may have a carbonyl group. More preferably, the term "heterocyclyl" as used herein, either alone or in combination with another radical, means a saturated or unsaturated, even more preferably, a saturated mono-, bi- or spirocyclic-ring system containing 1, 2, 3 or 4 heteroatoms selected from N, O or $S(O)_r$ with r=0, 1 or 2 which in addition may have a carbonyl group. The term "heterocyclyl is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

The term "heteroaryl" means a mono- or polycyclic, preferably mono- or bicyclic-ring system containing one or more heteroatoms selected from N, O or S(O)$_r$ with r=0, 1 or 2 wherein at least one of the heteroatoms is part of an aromatic ring, and wherein said ring system may have a carbonyl group. More preferably, the term "heteroaryl" as used herein, either alone or in combination with another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

-continued

Many of the terms given above may be used repeatedly in the definition of a formula or group and in each case have one of the meanings given above, independently of one another.

All rests and substituents as defined hereinbefore and hereinafter may be substituted with one or more F atoms.

Pharmacological Activity

The activity of the compounds of the invention may be demonstrated using the following ACC2 assay:

Spectrophotometric 384 Well Assay

Malonyl CoA formation by acetyl CoA carboxylases is stoichometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM KHCO$_3$, 10 mM MgCl$_2$, 0.5 mg/ml BSA, 3.75 mM reduced L-glutathione, 15 U/ml lactate dehydrogenase, 0.5 mM phosphoenolpyruvate, 15 U/ml pyruvate kinase, compounds at different concentrations at final DMSO concentrations of 1%.

The enzymatic reaction is then started by addition of a mixture of NADH, acetyl Coenzyme A (both 2000 f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')−S('LOW'))*100. Compounds will give values between 100% CTL (no inhibition) and 0% CTL (complete inhibition).

For IC$_{50}$ value determination, the sample slope in the presence of the test compound after subtraction of the low controls (S(compound)−S('LOW')) are used.

An IC$_{50}$ value is derived from the compound slopes at different dosages after subtraction of the low controls (S(compound)−S('LOW')) by non-linear regression curve fitting (equation y=(A+((B−A)/(1+((C/x)^D))))).

The compounds of general formula (I) according to the invention for example have IC$_{50}$ values below 5000 nM, particularly below 1000 nM, preferably below 300 nM, most preferably below 100 nM.

In the following table the activity expressed as IC$_{50}$ (μM) of compounds according to the invention is presented wherein the IC$_{50}$ values are determined in the ACC2 assay as described hereinbefore. The term "Example" refers to the example numbers according to the following experimental section.

| Example | IC$_{50}$ [μM] |
|---|---|
| 1.1 | 0.139 |
| 1.2 | 0.061 |
| 1.3 | 0.101 |
| 1.4 | 0.118 |
| 1.5 | 0.133 |
| 1.6 | 0.140 |
| 1.7 | 0.170 |
| 1.8 | 0.179 |
| 1.9 | 0.195 |
| 1.10 | 0.205 |
| 1.11 | 0.213 |
| 1.12 | 0.220 |
| 1.13 | 0.233 |
| 1.14 | 0.244 |
| 1.15 | 0.263 |
| 1.16 | 0.266 |
| 1.17 | 0.272 |
| 1.18 | 0.286 |
| 1.19 | 0.296 |
| 1.20 | 0.306 |
| 1.21 | 0.309 |
| 1.22 | 0.311 |
| 1.23 | 0.315 |
| 1.24 | 0.319 |
| 1.25 | 0.322 |
| 1.26 | 0.325 |
| 1.27 | 0.345 |
| 1.28 | 0.346 |
| 1.29 | 0.367 |
| 1.30 | 0.378 |
| 1.31 | 0.381 |
| 1.32 | 0.402 |
| 1.33 | 0.403 |
| 1.34 | 0.405 |
| 1.35 | 0.410 |
| 1.36 | 0.413 |
| 1.37 | 0.418 |
| 1.38 | 0.420 |
| 1.39 | 0.421 |
| 1.40 | 0.437 |
| 1.41 | 0.438 |
| 1.42 | 0.441 |
| 1.43 | 0.443 |
| 1.44 | 0.454 |
| 1.45 | 0.463 |
| 1.46 | 0.470 |
| 1.47 | 0.472 |
| 1.48 | 0.480 |
| 1.49 | 0.492 |
| 1.50 | 0.501 |
| 1.51 | 0.512 |
| 1.52 | 0.533 |
| 1.53 | 0.538 |
| 1.54 | 0.547 |
| 1.55 | 0.573 |
| 1.56 | 0.579 |
| 1.57 | 0.591 |
| 1.58 | 0.598 |
| 1.59 | 0.603 |
| 1.60 | 0.620 |
| 1.61 | 0.626 |
| 1.62 | 0.637 |
| 1.63 | 0.652 |
| 1.64 | 0.658 |
| 1.65 | 0.667 |
| 1.66 | 0.687 |
| 1.67 | 0.706 |
| 1.68 | 0.724 |
| 1.69 | 0.748 |
| 1.70 | 0.749 |

-continued

| Example | IC$_{50}$ [µM] |
|---|---|
| 1.71 | 0.779 |
| 1.72 | 0.789 |
| 1.73 | 0.798 |
| 1.74 | 0.813 |
| 1.75 | 0.818 |
| 1.76 | 0.838 |
| 1.77 | 0.849 |
| 1.78 | 0.878 |
| 1.79 | 0.907 |
| 1.80 | 0.907 |
| 1.81 | 0.934 |
| 1.82 | 0.940 |
| 1.83 | 1.069 |
| 1.84 | 1.121 |
| 1.85 | 1.225 |
| 1.86 | 1.379 |
| 1.87 | 1.379 |
| 1.88 | 1.779 |
| 1.89 | 1.883 |
| 1.90 | 2.226 |
| 1.91 | 2.921 |
| 1.92 | 3.702 |
| 1.93 | 5.485 |
| 2.1 | 0.095 |
| 2.2 | 0.179 |
| 2.3 | 0.188 |
| 2.4 | 0.399 |
| 2.5 | 0.575 |
| 2.6 | 0.808 |
| 3.1 | 0.235 |
| 3.2 | 0.259 |
| 3.3 | 0.280 |
| 3.4 | 0.300 |
| 3.5 | 0.318 |
| 3.6 | 0.352 |
| 3.7 | 0.613 |
| 3.8 | 0.622 |
| 3.9 | 0.739 |
| 3.10 | 0.955 |
| 3.11 | 1.015 |
| 3.12 | 1.026 |
| 3.13 | 1.953 |
| 4.1 | 0.288 |
| 4.2 | 0.575 |
| 5 | 1.765 |
| 6.1 isomer 1 | 0.057 |
| 6.1 isomer 2 | 0.775 |
| 6.2 isomer 1 | 0.086 |
| 6.2 isomer 2 | 0.177 |
| 6.2 isomer 3 | 0.219 |
| 6.2 isomer 4 | 1.483 |
| 6.3 isomer 1 | 0.095 |
| 6.3 isomer 2 | 1.099 |
| 6.4 isomer 1 | 0.121 |
| 6.4 isomer 3 | 0.127 |
| 6.4 isomer 2 | 0.681 |
| 6.5 isomer 1 | 0.135 |
| 6.5 isomer 2 | 0.872 |
| 6.6 isomer 1 | 0.126 |
| 6.7 isomer 1 | 0.609 |
| 6.8 isomer 1 | 0.043 |
| 6.8 isomer 2 | 0.789 |
| 7.1 | 0.041 |
| 7.2 | 0.072 |
| 7.3 | 0.190 |
| 7.4 | 0.224 |
| 7.5 | 0.225 |
| 7.6 | 0.229 |
| 7.7 | 0.265 |
| 7.8 | 0.274 |
| 7.9 | 0.315 |
| 7.10 | 0.329 |
| 7.11 | 0.365 |
| 7.12 | 0.375 |
| 7.13 | 0.379 |
| 7.14 | 0.407 |
| 7.15 | 0.408 |
| 7.16 | 0.410 |
| 7.17 | 0.414 |
| 7.18 | 0.429 |
| 7.19 | 0.435 |
| 7.20 | 0.445 |
| 7.21 | 0.454 |
| 7.22 | 0.455 |
| 7.23 | 0.470 |
| 7.24 | 0.473 |
| 7.25 | 0.500 |
| 7.26 | 0.542 |
| 7.27 | 0.563 |
| 7.28 | 0.583 |
| 7.29 | 0.600 |
| 7.30 | 0.630 |
| 7.31 | 0.639 |
| 7.32 | 0.715 |
| 7.33 | 0.821 |
| 7.34 | 0.075 |
| 8.1 | 0.104 |
| 8.2 | 0.353 |
| 8.3 | 0.543 |
| 8.4 | 0.910 |
| 9.1 | 0.444 |
| 9.2 | 0.975 |

In view of their ability to inhibit acetyl-CoA carboxylase(s), the compounds of general formula (I) according to the invention and the corresponding salts thereof are theoretically suitable for the treatment, including preventative treatment of all those diseases or conditions which may be affected or which are mediated by the inhibition of acetyl-CoA carboxylase(s), in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase(s), in particular ACC2, in a patient, preferably in a human.

In yet another aspect the present invention relates a method for treating, including preventing a disease or condition mediated by the inhibition of acetyl-CoA carboxylase(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as is hyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, micro-albuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance.

Obesity and overweight are generally defined by body mass index (BMI), which is correlated with total body fat and estimates the relative risk of disease. BMI is calculated by weight in kilograms divided by height in meters squared (kg/m$^2$). Overweight is typically defined as a BMI of 25-29.9 kg/m$^2$, and obesity is typically defined as a BMI of 30 kg/m$^2$ or greater.

According to another aspect the compounds of the present invention are particularly suitable for treating, inclduing preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:
A. disorders of fatty acid metabolism and glucose utilization disorders; disorders in which insulin resistance is involved;
B. hepatic disorders and conditions related thereto, including:
   fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;
C. skin disorders and conditions and those associated with polyunsaturated fatty acids, such as
   eczema, acne, sebaceous gland diseases, psoriasis, keloid scar formation or prevention, other diseases related to mucous membrane fatty acid composition;
D. primary hypertriglyceridemia or secondary hypertriglyceridemias following familial histiocytic reticulosis, lipoprotein lipase deficiency, hyperlipoproteinemias, apolipoprotein deficiency (e.g. apoCII or apoE deficiency);
E. diseases or conditions related to neoplastic cellular proliferation, for example benign or malignant tumors, cancer, neoplasias, metastases, carcinogenesis;
F. diseases or conditions related to neurological, psychiatric or immune disorders or conditions;
G. other diseases or conditions in which inflammatory reactions, cell differentiation and/or other ACC-mediated aspects may for example be involved are:
   atherosclerosis such as, for example (but not restricted thereto), coronary sclerosis including angina pectoris or myocardial infarction, stroke, ischemic, stroke and transient ischemic attack (TIA),
   peripheral occlusive disease,
   vascular restenosis or reocclusion,
   chronic inflammatory bowel diseases such as, for example, Crohn's disease and ulcerative colitis,
   pancreatitis,
   sinusitis,
   retinopathy, ischemic retinopathy,
   adipose cell tumors,
   lipomatous carcinomas such as, for example, liposarcomas,
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
   tumors in which ACC is up regulated,
   acute and chronic myeloproliferative disorders and lymphomas, angiogenesis
   neurodegenerative disorders including Alzheimer's disease, multiple sclerosis, Parkinson's disease, epilepsy,
   erythemato-squamous dermatoses such as, for example, psoriasis,
   acne vulgaris,
   other skin disorders and dermatological conditions which are modulated by PPAR,
   eczemas and neurodermatitis,
   dermatitis such as, for example, seborrheic dermatitis or photodermatitis,
   keratitis and keratoses such as, for example, seborrheic keratoses, senile keratoses, actinic keratoses, photo-induced keratoses or keratosis follicularis,
   keloids and keloid prophylaxis,
   bacterial infections,
   fungal infections,
   warts, including condylomata or condylomata acuminata
   viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV). venereal papillomata, viral warts such as, for example, molluscum contagiosum, leukoplakia,
   papular dermatoses such as, for example, lichen planus,
   skin cancer such as, for example, basal-cell carcinomas, melanomas or cutaneous T-cell lymphomas,
   localized benign epidermal tumors such as, for example, keratoderma, epidermal naevi,
   chilblains;
   high blood pressure,
   polycystic ovary syndrome (PCOS),
   asthma,
   cystic fibrosis,
   osteoarthritis,
   lupus erythematosus (LE) or inflammatory rheumatic disorders such as, for example rheumatoid arthritis,
   vasculitis,
   wasting (cachexia),
   gout, ischemia/reperfusion syndrome,
acute respiratory distress syndrome (ARDS)
viral diseases and infections
lipodystrophy and lipodystrophic conditions, also for treating adverse drug effect;
myophathies and lipid myopathis (such as carnitine palmitoyltransferase I or II deficiency);

H. formation of muscles and a lean body or muscle mass formation.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11beta-hydroxy steroid dehydrogenase-1 (11beta-HSD type 1) inhibitors, stearoyl-CoA desaturase-1 (SCD-1) inhibitors, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-Y antagonists (e.g., NPY Y5 antagonists), $PY_{Y3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitors, histamine 3 antagonists or inverse agonists, neuromedin U agonists, MTP/ApoB inhibitors (e.g., gut-selective MTP inhibitors), opioid antagonists, orexin antagonists, and the like.

Preferred anti-obesity agents for use in the combination aspects of the present invention include gut-selective MTP inhibitors CCKa agonists, 5HT2c agonists, MCR4 agonists, lipase inhibitors, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include sodium-glucose co-transporter (SGLT) inhibitors, 11beta-hydroxy steroid dehydrogenase-1 (11beta-HSD type 1) inhibitors, phosphodiesterase (PDE) 10 inhibitors, diacylglycerol acyltransferase (DGAT) 1 or 2 inhibitors, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, an alpha-amylase inhibitors (e.g., tendamistat, trestatin and AL-3688), alpha-glucoside hydrolase inhibitors (e.g., acarbose), alpha-glucosidase inhibitors (e.g., adiposine, camiglibose, emiglitate, miglitol, voglibose, pradimicin-Q, and salbostatin), PPAR gamma agonists (e.g., balaglitazone, ciglitazone, darglitazone, englitazone, isaglitazone, pioglitazone, rosiglitazone and troglitazone), PPAR alpha/gamma agonists (e.g., CLX-0940, GW-1536, GW-20 1929, GW-2433, KRP-297, L-796449, LR-90, MK-0767 and SB-219994), biguanides (e.g., metformin), GLP-1 derivatives, glucagon-like peptide 1 (GLP-1) agonists (e.g., Byetta™, exendin-3 and exendin-4), GLP-1 receptor and glucagon receptor co-agonists, glucagon receptor antagonists, GIP receptor antagonists, protein tyrosine phosphatase-1 B (PTP-1 B) inhibitors (e.g., trodusquemine, hyrtiosal extract), SIRT-1 activators (e.g. reservatrol), dipeptidyl peptidease IV (DPP-IV) inhibitors (e.g., sitagliptin, vildagliptin, alogliptin, linagliptin and saxagliptin), insulin secretagogues, GPR119 agonists, GPR40 agonists, TGR5 agonists, MNK2 inhibitors, GOAT (Ghrelin O-Acyltransferase) inhibitors, fatty acid oxidation inhibitors, A2 antagonists, c-jun amino-terminal kinase (JNK) inhibitors, insulins, insulin derivatives, fast acting insulins, inhalable insulins, oral insulins, insulin mimetics, glycogen phosphorylase inhibitors, VPAC2 receptor agonists and glucokinase activators.

Preferred anti-diabetic agents are metformin, glucagon-like peptide 1 (GLP-1) agonists (e.g., Byetta™), GLP-1 receptor and glucagon receptor co-agonists, sodium-glucose co-transporter (SGLT) inhibitors, 11beta-hydroxy steroid dehydrogenase-1 (11beta-HSD type 1) inhibitors and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the acetyl-CoA carboxylase(s), in particular ACC2, in particular diseases or conditions as described hereinbefore and hereinafter.

In yet another aspect the present invention relates a method for treating, including preventing a disease or condition mediated by the inhibition of acetyl-CoA carboxylase(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

Synthesis Schemes

Compounds of general formula (I) may be prepared by palladium-mediated Buchwald reactions or copper-mediated Ullmann reactions of aryl- or heteroarylhalides ($Ar^1$—Z; II), that are optionally substituted with 1-3 $R^1$, with pyrrolidines (III), wherein Z is a leaving group and for example denotes Cl, Br or I.

Compounds of general formula (I) may alternatively be prepared by amide coupling reactions of carboxylic acids (IV) with amines (V) mediated by coupling reagents such as for example 2-(1H-benzotriazol-1-yl)-1,1,3,3-tetramethyluronium tetrafluoroborat (TBTU), 1-chloro-N,N-2-trimethylpropenylamine, benzotriazol-1-yloxy)tripyrrolidino-phosphonium hexafluorophosphate and 2-chloro-1,3-dimethyl-2-imidazolinium hexafluorophosphate.

Compounds of general formula (VI), wherein Py is a pyridinylene or pyrimidinylene group that is optionally substituted with one or two $R^1$, may be prepared by nucleophilic aromatic substitution reactions ($S_NAr$) of pyrimidyl or pyridyl halides (VII) with pyrrolidines (III), wherein Z is a leaving group which for example denotes F, Cl, Br, I.

Compounds of general formula (VIII) may be prepared by aromatic substitution of pyrimidyl or pyridyl halides (IX) with amines (X) wherein $R^{N1}$ and $R^{N2}$ are independently of each other selected from the group consisting of H, $C_{1-6}$-alkyl, $C_{3-7}$-cycloalkyl and —($C_{1-3}$-alkyl)-($C_{3-7}$-cycloalkyl), wherein said $C_{1-6}$-alkyl, $C_{3-7}$-cycloalkyl and —($C_{1-3}$-alkyl)-($C_{3-7}$-cycloalkyl) groups may each be substituted by one or more F or OH, wherein said substituents are the same or different; or wherein $R^{N1}$ and $R^{N2}$ together form a 4- to 7-membered monocyclic heterocyclic ring that additionally to the nitrogen atom to which $R^{N1}$ and $R^{N2}$ are attached may contain 1 or 2 hetereoatoms independently selected from N, O and S and that may be substituted with one or more F or OH and Z is a leaving group which for example denotes F or Cl, Br, I.

(IX) + (X) → (VIII)

Compounds of general formula (XI), wherein Py is a pyridinylene or pyrimidinylene group that is optionally substituted with one or two R¹, may be prepared by palladium-mediated Suzuki reactions of pyrimidinyl or pyridyl halides (IX) with boronic acids (XII) or corresponding boronic esters wherein Z is a leaving group which for example denotes Cl, Br or I.

(IX) + (XII) → (XI)

Carboxylic acids of general formula (IV) may be prepared by hydrolysis of esters (XIII) under aqueous conditions either using acidic or basic conditions wherein Y is an alkyl group which for example denotes methyl or ethyl.

Esters of general formula (XIII) are prepared analogously to compounds of general formula (I) from pyrrolidines (III), e.g. by palladium-mediated Buchwald reactions or copper-mediated Ullmann reactions or by nucleophilic aromatic substitution reactions (see above).

(XIII) → (IV)

Carboyxlic acids of general formula (XIV) may be prepared by aromatic substitution of pyrimidyl or pyridyl halides (XV) with amines (X) wherein $R^{N1}$ and $R^{N2}$ are as defined above and Y is an alkyl group which for example denotes methyl or ethyl and Z is a leaving group which for example denotes F or Cl, Br, I followed by hydrolysis of the ester.

(XV) + (X) → (XIV)

Carboyxlic acids of general formula (XVI) may be prepared by aromatic substitution of pyrimidyl or pyridyl halides (XV) with alcohols (XVII) wherein $R^{O1}$ is selected from the group consisting of $C_{1-6}$-alkyl, $C_{3-7}$-cycloalkyl, —($C_{1-3}$-alkyl)-($C_{3-7}$-cycloalkyl), heterocyclyl, —($C_{1-3}$-alkyl)-(heterocyclyl), phenyl and —($C_{1-3}$-alkyl)-phenyl, wherein each alkyl, cycloalkyl and heterocyclyl is optionally substituted with one or more substituents selected from F and OH; and wherein each heterocyclyl group is selected from a 4- to 7-membered monocyclic heterocyclic ring that contains 1, 2 or 3 hetereoatoms independently selected from N, O and S and may be substituted with one or more F or OH; and Y is an alkyl group which for example denotes methyl or ethyl and Z is a leaving group which for example denotes F or Cl, Br, I followed by hydrolysis of the ester. Alcohols are used in their deprotonated form.

(XV) + (XIX)

-continued (XVI)

Compounds of general formula (III) may be prepared by nucleophilic displacement of protected pyrrolidines (XVIII) by phenols (XIX) under inversion of configuration followed by a deprotection reaction suited to remove the chosen protection group, wherein PG is a protecting group and for example denotes tert.-butoxycarbonyl or benzyloxycarbonyl and Z is a leaving group and for example denotes mesylate, tosylate, Cl, Br or I.

(XVIII) + (XIX) → (III)

The synthetic routes presented may rely on the use of protecting groups. For example, reactive groups present, such as hydroxy, carbonyl, carboxy, amino, alkylamino or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

EXPERIMENTAL PART

The Examples that follow are intended to illustrate the present invention without restricting it. The terms "ambient temperature" and "room temperature" are used interchangeably and designate a temperature of about 20° C.

| Abreviations: | |
|---|---|
| aq. | aqueous |
| ACN | acetonitrile |
| BOC | tert-butoxy-carbonyl- |
| d | day |
| DCM | dichloromethane |
| DIPEA | N,N-diisopropylethylamine |
| DMF | N,N-dimethylformamide |
| EtOAc | ethyl acetate |
| EtOH | ethanol |
| eq | equivalent |
| Ex | example |
| h | hour |
| MeOH | methanol |
| min | minute |
| n.d. | not determined |
| NMP | N-methyl-2-pyrrolidone |
| PE | petroleum ether |
| Prep. | preparative |
| r.t. | room temperature (about 20° C.) |
| sat. | saturated |
| TEA | triethylamine |
| TF/TFA | trifluoroacetic acid |
| THF | tetrahydrofuran |
| TBTU | 2-(1H-benzotriazol-1-yl)-1,1,3,3-tetramethyluronium tetrafluoroborat |

PREPARATION OF STARTING COMPOUNDS

Example I

N-Ethyl-2-(4-hydroxy-phenyl)-propionamide

-continued

[structure: 2-(4-hydroxyphenyl)-N-ethyl-propionamide]

To 4.00 g (24.1 mmol) 2-(4-hydroxyphenyl)propionic acid in 50 mL THF and 5 ml DMF are added 6.76 g (66.1 mmol) TEA and 8.50 g TBTU. The reaction mixture is stirred at r.t. for 5 min, then 36.1 ml (2 mold solution; 72.2 mmol) ethylamine are added. The reaction mixture is stirred at r.t. 5 h. The solvent is removed in vacuo and the crude product is purified by prep. HPLC-MS (ACN/H$_2$O/NH$_4$OH).

$C_{11}H_{15}NO_2$ (M=193.2 g/mol)
ESI-MS: 194 [M+H]$^+$
R$_t$ (HPLC): 0.43 min (method E)

Example II (S)-3-Methanesulfonyloxy-pyrrolidine-1-carboxylic acid tert-butyl ester

[reaction scheme]

To 3.44 g (187 mmol) (S)-1-Boc-3-pyrrolidinol in 15 ml THF are added 1.70 mL (21.6 mmol) of methanesulfonyl chloride at 0° C. The reaction mixture is stirred for 1 h. Water is added and it is extracted with EtOAc (3×). The organic layer is washed with an aq. NaHCO$_3$ solution and dried over MgSO$_4$. The solvent is removed in vacuo.

$C_{10}H_{19}NO_5S$ (M=265.3 g/mol)
R$_t$ (HPLC): 0.67 min (method B)

Example III (R)-N-Ethyl-2-[4-(pyrrolidin-3-yloxy)-phenyl]-propionamide

[reaction scheme continued]

a) A mixture of 4.74 g (17.9 mmol) of example II, 3.42 g (17.7 mmol) of example 1 and 11.5 g (35.4 mmol) Cs$_2$CO$_3$ in 30 mL DMF is stirred at 80° C. for 16 h and further 24 h at 100° C. The reaction mixture is cooled to r.t. and water and EtOAc are added. The layers are separated and the aq. layer is extracted with EtOAc. The organic layers are combined, washed with 4N NaOH and sat. aq. NaHCO$_3$ solution, dried over MgSO$_4$, filtered and the solvent is removed in vacuo. The crude product is used without further purification.

$C_{20}H_{30}N_2O_4$ (M=362.5 g/mol)
ESI-MS: 380 [M+NH$_4$]$^+$
R$_t$ (HPLC): 0.88 min (method B)

b) The mixture of 5.70 g of the above mentioned product in 10 ml dioxane and 15 ml of HCl (4N in dioxane) is stirred for 3 h at r.t. The reaction mixture is adjusted to an alkaline pH with 1N aq. NaOH solution and is extracted with DCM. The organic layers are combined, washed with aq. NaHCO$_3$ solution, dried over MgSO$_4$, filtered and the solvent is removed in vacuo. The resulting product is purified by prep. HPLC-MS (ACN/H$_2$O/NH$_4$OH).

$C_{15}H_{22}N_2O_2$ (M=262.3 g/mol)
ESI-MS: 263 [M+H]$^+$
R$_t$ (HPLC): 0.64 min (method E)

Example IV 2-(4-Hydroxy-phenyl)-propionic acid ethyl ester

[reaction scheme]

To a mixture of 13.0 g (78.2 mmol) of 2-(4-hydroxyphenyl) propionic acid in 250 ml EtOH 5.82 ml (78.2 mmol) thionyl chloride are added slowly at 0° C. The reaction mixture is stirred at 70° C. for 2 h. After cooling to r.t. the solvent is removed in vacuo. The residue is mixed with toluene and the solvent is removed again.

$C_{11}H_{14}O_3$ (M=194.2 g/mol)
ESI-MS: 195 [M+H]$^+$
R$_t$ (HPLC): 0.77 min (method B)

Example V

(R)-2-[4-(Pyrrolidin-3-yloxy)-phenyl]-propionic acid ethyl ester hydrochloride a) The mixture of 11.0 g (41.5 mmol) of example II, 8.05 g (41.5 mmol) of example IV and 27.0 g (82.9 mmol) Cs$_2$CO$_3$ in 150 mL DMF is stirred at 80° C. for 16 h. 2.0 g of example II are added and it is stirred for 2 h at 80° C. Then the reaction mixture is poured into icewater and is extracted with EtOAc. The organic layers are combined, washed with brine, dried over MgSO$_4$, filtered and the solvent is removed in vacuo. The crude product is purified by flash chromatography (silica gel, DCM/MeOH 98/2).

C$_{20}$H$_{29}$NO$_5$ (M=363.5 g/mol)

ESI-MS: 364 [M+H]$^+$

R$_t$ (HPLC): 1.03 min (method B)

b) The mixture of 10.4 g (28.6 mmol) of the above mentioned product and 28.6 ml of 4N HCl in dioxane is stirred for 2 h at r.t. The solvent is removed in vacuo. The residue is mixed with water and extracted with DCM. The aq. layers are combined and the solvent is removed in vacuo.

C$_{15}$H$_{21}$NO$_3$*HCl (M=299.8 g/mol)

ESI-MS: 264 [M+H]$^+$

R$_t$ (HPLC): 0.63 min (method E)

Example VI

2-(4-[1-(3-Fluoro-2-propylamino-pyridin-4-yl)-(R)-pyrrolidin-3-yloxy]-phenyl)-propionic acid a) The mixture of 0.83 g (5.00 mmol) of 2,4-dichloro-3-fluoro-pyridine, 1.50 g (5.00 mmol) of example V and 2.77 g (20.0 mmol) of K$_2$CO$_3$ in NMP is stirred at 80° C. for 16 h and further 5 h at 100° C. 1.50 ml of TEA is added and the reaction mixture is stirred at 80° C. for 19 h. Then the reaction mixture is cooled to r.t., diluted with water and extracted with EtOAc. The organic layers are combined, the solvent is removed in vacuo and the crude product is purified by prep. HPLC-MS (ACN/H$_2$O/TFA).

C$_{20}$H$_{22}$ClFN$_2$O$_3$ (M=392.9 g/mol)

ESI-MS: 393 [M+H]$^+$

R$_t$ (HPLC): 1.01 min (method B)

b) 750 mg (1.91 mmol) of the above mentioned product are mixed with 25 ml dioxane under nitrogen atmosphere. 757 mg (7.64 mmol) of soduim-tert-butylat, 785 µl (9.55 mmol) of propylamine, 87 mg (0.10 mmol) of tris-(dibenzylidenaceton)-dipalladium(0) and 114 mg (0.38 mmol) of 2-(di-tert-butylphosphino)biphenyl are added. The reaction mixture is stirred at 80° C. for 2 h. The reaction mixture is diluted with water and extracted with EtOAc. The organic layer is washed with 0.1N aq. NaOH. The aq. layers are combined, acidified with 1N HCl and extracted with EtOAc. The aq. layer is sat. with NaCl and extraceted with ACN/EtOAc. The organic layers are combined dried over MgSO$_4$, filtered and the solvent is removed in vacuo. The residue is purified by prep. HPLC-MS (ACN/H$_2$O/TFA). The product is isolated as TFA salt.

C$_{21}$H$_{26}$FN$_3$O$_3$*C$_2$HF$_3$O$_2$ (M=501.5 g/mol)

ESI-MS: 388 [M+H]$^+$

R$_t$ (HPLC): 0.71 min (method B)

Example VII

2-(4-(1-[6-(2,2-Difluoro-propoxy)-5-fluoro-pyrimidin-4-yl]-(R)-pyrrolidin-3-yloxy)-phenyl)-propionic acid

-continued a) To the mixture of 1.50 g (5.00 mmol) of example V and 0.84 g (5.00 mmol) of 4,6-dichloro-5-fluoro-pyrimidine in 10 ml THF are added 1.48 ml (10.5 mmol) of TEA. The reaction mixture is stirred at r.t. for 4 h. Then the reaction mixture is diluted with water and extracted with EtOAc. The organic layers are combined, washed with water and brine and dried over MgSO$_4$. The solvent is removed in vacuo.

$C_{19}H_{21}ClFN_3O_3$ (M=393.8 g/mol)
ESI-MS: 394 [M+H]$^+$
R$_t$ (HPLC): 1.07 min (method B)

b) 695 mg (7.24 mmol) of 2,2-difluoropropanol are dissolved in 4 ml THF. 421 mg (9.65 mmol) of sodium hydride (55% in mineral oil) are added slowly and portionwise. It is stirred for 15 min. 1.90 g (4.82 mmol) of the above mentioned product are dissolved in 4 ml THF and are added slowly. The reaction mixture is stirred at 50° C. for 2 h. The reaction mixture is cooled to r.t and stirred for 16 h. The reaction mixture is diluted with water, THF is removed in vacuo. The residue is extracted with EtOAc. The aq. layer is acidified with 1N HCl and extracted with EtOAc. The organic layers are combined dried over MgSO$_4$, filtered and the solvent is removed in vacuo. The residue is purified by prep. HPLC-MS (ACN/H$_2$O/TFA).

$C_{20}H_{22}F_3N_3O_4$ (M=425 g/mol)
ESI-MS: 426 [M+H]$^+$
R$_t$ (HPLC): 0.97 min (method B)

Example VIII 2-(4-(1-[5-Chloro-6-(2-hydroxy-2-methyl-propoxy)-pyrimidin-4-yl]-(R)-pyrrolidin-3-yloxy)-phenyl-propionic acid -continued a) The mixture of 0.92 g (5.0 mmol) of 4,5,6-trichloropyrimidine, 1.50 g (5.00 mmol) of example V and 2.07 g (15.0 mmol) of K$_2$CO$_3$ in ACN is stirred at r.t. for 16 h and further 4 h at 70° C. 1.0 ml of TEA is added and the reaction mixture is stirred at 70° C. for 1 h and at r.t. 2 d. Then the reaction mixture is filtered, the precipitate is washed with EtOAc and the solvent is removed in vacuo. The residue is extracted with water and EtOAc, the organic layer is washed with brine, dried over MgSO$_4$, filtered and the solvent is removed in vacuo. The crude product is purified by prep. HPLC-MS (ACN/H$_2$O/TFA). The needed fractions are combined and the ACN is removed in vacuo. The residue is extracted with EtOAc. The organic layer is washed with brine, dried over MgSO$_4$, filtered and the solvent is removed in vacuo.

$C_{19}H_{21}Cl_2N_3O_3$ (M=410.3 g/mol)
ESI-MS: 410 [M+H]$^+$
R$_t$ (HPLC): 1.11 min (method B)

b) 835 mg (9.26 mmol) of 2-methyl-propane-1,2-diol are dissolved in 4 ml THF. 424 mg (9.72 mmol) of sodium hydride (55% in mineral oil) are added slowly and portionwise. It is stirred for 15 min. 1.90 g (4.82 mmol) of the above mentioned product are dissolved in 4 ml THF and are added slowly. The reaction mixture is stirred at r.t. for 3 h. The reaction mixture is diluted with water, THF is removed in vacuo. The residue is extracted with EtOAc. The aq. layer is acidified with 1N HCl and extracted with EtOAc. The organic layers are combined dried over MgSO$_4$, filtered and the solvent is removed in vacuo. The residue is purified by prep. HPLC-MS (ACN/H$_2$O/TFA).

$C_{21}H_{26}ClN_3O_5$ (M=435.9 g/mol)
ESI-MS: 436 [M+H]$^+$
R$_t$ (HPLC): 0.58 min (method E)

Example IX 2-(4-[1-(2-Dimethylamino-5-fluoro-pyrimidin-4-yl)-(R)-pyrrolidin-3-yloxy]-phenyl)-propionic acid a) 0.840 g (5.00 mmol) of 2,4-dichlor-5-fluoropyrimidine are dissolved in 50 ml acetone and cooled to 0° C. 2.07 g (15.0 mmol) of K₂CO₃ and 1.50 g (5.00 mmol) of example V are added. The reaction mixture is stirred at r.t. for 16 h and further 5 h at 70° C. 0.70 ml of TEA are added and the reaction mixture is stirred at r.t. for 16 h. Then the reaction mixture is filtered, the precipitate is washed with EtOAc and the solvent is removed in vacuo. The residue is extracted with water and EtOAc, the organic layer is washed with brine, dried over MgSO₄, filtered and the solvent is removed in vacuo. The crude product is purified by prep. HPLC-MS (ACN/H₂O/TFA). The needed fractions are combined and the ACN is removed in vacuo. The residue is extracted with EtOAc. The organic layer is washed with brine, dried over MgSO₄, filtered and the solvent is removed in vacuo.

C₁₉H₂₁ClFN₃O₃ (M=393.8 g/mol)

ESI-MS: 394 [M+H]⁺

R$_t$ (HPLC): 1.06 min (method B)

b) 1.10 g (2.79 mmol) of the above mentioned product are dissolved in 10 ml NMP. 1.17 ml (8.38 mmol) TEA and 456 mg (5.59 mmol) of dimethylmine hydrochloride are added and the reaction mixture is stirred at 60° C. for 16 h. 6 eq TEA and 6 eq dimethylamine hydrochloride are added and it is stirred at 90° C. for 21 h. The reaction mixture is diluted with water and extracted with EtOAc. The organic layers are combined, washed with brine, dried over MgSO₄, filtered and the solvent is removed in vacuo. The residue is purified by prep. HPLC-MS (ACN/H₂O/TFA). The needed fractions are combined and the ACN is removed in vacuo. The residue is extracted with EtOAc, dried over MgSO₄, filtered and the solvent is removed in vacuo.

C₂₁H₂₇FN₄O₃ (M=402.5 g/mol)

ESI-MS: 403 [M+H]⁺

R$_t$ (HPLC): 0.78 min (method B)

c) 1.00 g (2.48 mmol) of the above mentioned product are dissolved in 20 ml EtOH. 9.94 ml (9.94 mmol) of 1N aq. NaOH are added and it is stirred at 50° C. for 2 h. The reaction mixture is acidified with 1N aq. HCl. EtOH is removed in vacuo. The residue is extracted with EtOAc. The aq. layer is saturated with NaCl and extracted once more with EtOAc. The combined organic layers are dried over MgSO₄, filtered and the solvent is removed in vacuo.

C₁₉H₂₃FN₄O₃ (M=374.4 g/mol)

ESI-MS: 375 [M+H]⁺

R$_t$ (HPLC): 0.68 min (method B)

Example X

2-Bromo-5-(2,2-difluoro-cyclopropylmethoxy)-pyridine

The mixture of 5.00 g (28.7 mmol) of 2-bromo-5-hydroxypyridine, 6.14 g (35.9 mmol) of 1-bromomethyl-2,2-difluorocyclopropane and 9.93 g (71.8 mmol) of K₂CO₃ in 100 ml ACN is stirred at 70° C. for 14 h. The reaction mixture is diluted with EtOAc, washed with water and 1N aq. NaOH, dried over MgSO₄, filtered and the solvent is removed in vacuo.

C₉H₈BrF₂NO (M=264.1 g/mol)

ESI-MS: 264 [M+H]⁺

R$_t$ (HPLC): 0.84 min (method E)

Example XI 2-(4-(1-[5-(2,2-Difluoro-cyclopropylmethoxy)-pyridin-2-yl]-(R)-pyrrolidin-3-yloxy)-phenyl)-propionic acid 1.40 g (4.67 mmol) of example V are dissolved in 30 ml dioxane under nitrogen atmosphere. 1.20 g (12.1 mmol) of sodium tert.butylate and 0.80 g (3.0 mmol) of example X are added. Then 139 mg (0.15 mmol) of tris-(dibenzylidenaceton)-dipalladium (0) and 181 mg (0.61 mmol) of 2-(di-tert-butylphosphino)biphenyl are added and the reaction mixture is stirred at 80° C. for 3 h. The reaction mixture is diluted with water and extracted with EtOAc. The organic layer is washed with 0.1N aq. NaOH. The combined aq. layers are acidified with 1N aq. HCl and extracted with EtOAc. The aq. layer is saturated with NaCl and extracted once more with EtOAc. The organic layers are combined, dried over MgSO$_4$, filtered and the solvent is removed in vacuo.

The residue is purified by prep. HPLC-MS (ACN/H$_2$O/TFA).

C$_{22}$H$_{24}$F$_2$N$_2$O$_4$ (M=418.4 g/mol)
ESI-MS: 419 [M+H]$^+$
R$_t$ (HPLC): 0.71 min (method B)

Example XII

(R)-2-(4-[1-(2-Chloro-pyrimidin-4-yl)-pyrrolidin-3-yloxy]-phenyl)-N-ethyl-propionamide 0.50 g (1.9 mmol) of example III are dissolved in 10 ml ACN. 0.50 ml (2.9 mmol) of DIPEA and 284 mg (1.91 mmol) of 2,4-dichloropyrimidine are added. The reaction mixture is stirred at r.t. over night. The solvent is removed in vacuo. The residue is diluted with water and EtOAc. The layers are separated. The organic layer is washed with 10% aq. KHSO$_4$, dried over MgSO$_4$, filtered and the solvent is removed in vacuo.

C$_{19}$H$_{23}$ClN$_4$O$_2$ (M=374.9 g/mol)
ESI-MS: 375 [M+H]$^+$
R$_t$ (HPLC): 1.05 min (method C)

Example XIII

2-(4-(1-[5-Fluoro-6-(2-hydroxy-2-methyl-propoxy)-pyrimidin-4-yl]-(R)-pyrrolidin-3-yloxy)-phenyl)-propionic acid a) step VII a)
b) 398 mg (4.42 mmol) of 2-methyl-propane-1,2-diol are dissolved in 50 ml THF. Molecular sieve is added and it is stirred for 15 min. The molecular sieve is filtered off. 130 mg (2.95 mmol) of sodium hydride (55% in mineral oil) are added to the filtrate. The mixture is stirred for 10 min, then 580 mg (1.47 mmol) of the product mentioned above (step XIII a) are added. The reaction mixture is stirred at r.t. for 45 min and at 50° C. over night. 130 mg (2.95 mmol) of sodium hydride (55% in mineral oil) and 580 mg (1.47 mmol) of the above mentioned product are added. The reaction mixture is stirred at 50° C. for 5 h and then at 50° C. over night. The solvent is removed in vacuo. The residue is dissolved in water/DMF and acidified with HCl and then purified by prep. HPLC-MS (ACN/H$_2$O/TFA).

O$_{21}$H$_{26}$FN$_3$O$_5$ (M=419.5 g/mol)
ESI-MS: 420 [M+H]$^+$
R$_t$ (HPLC): 0.86 min (method B)

Example XIV

2-(4-[1-(5-Fluoro-6-propylamino-pyrimidin-4-yl)-(R)-pyrrolidin-3-yloxy]-phenyl)-propionic acid a) step VII a)
b) 420 mg (1.07 mmol) of the above mentioned product, 0.11 ml (1.3 mmol) of propylamine and 0.37 ml (2.1 mmol) of DIPEA are dissolved in 4 ml NMP. The reaction mixture is stirred in a sealed tube at 80° C. over night. 350 µl of propylamine are added and the reaction mixture is stirred at 80° C. for 2 d. The reaction mixture is diluted with water/MeOH and purified by prep. HPLC-MS (ACN/H$_2$O/TFA).

C$_{22}$H$_{29}$FN$_4$O$_3$ (M=416.5 g/mol)
ESI-MS: 417 [M+H]$^+$
R$_t$ (HPLC): 0.86 min (method B)

c) The mixture of 450 mg (1.08 mmol) of the above mentioned product and 2.16 ml (2.16 mmol) 1N aq. NaOH in 10 ml EtOH is stirred at r.t. for 2 h. 2 ml of 1N aq. NaOH are added and it is stirred at r.t. over night. EtOH is removed in vacuo. The residue is diluted with water and acidified with 1N aq. HCl. EtOAc is added and the layers are seperated. The aq. layer is extracted once more with EtOAc. The combined organic layers are dried over MgSO$_4$, filtered and the solvent is removed in vacuo.

$C_{20}H_{25}FN_4O_3$ (M=388.4 g/mol)
ESI-MS: 389 [M+H]$^+$
R$_t$ (HPLC): 0.73 min (method B)

Example XV

1-Bromo-4-cyclobutoxy-benzene

The mixture of 2.50 g (14.5 mmol) of 4-bromophenol, 2.04 ml (21.7 mmol) of cyclobutyl bromide and 7.99 g (57.8 mmol) of K$_2$CO$_3$ in 25 ml DMF is stirred at 120° C. over night. The reaction mixture is extracted with water and EtOAc. The organic layer is dried, filtered and the solvent is removed in vacuo.

$C_{10}H_{11}BrO$ (M=227.1 g/mol)
ESI-MS: 227 [M+H]$^+$
R$_t$ (HPLC): 1.39 min (method D)

Example XVI

2-Bromo-5-(2,2-difluoro-cyclopropylmethoxy)-pyridine

The mixture of 0.30 g (1.7 mmol) of 2-bromo-5-hydroxy-pyridine, 0.59 g (3.5 mmol) of 1-bromoethyl-2,2-difluorocyclopropane and 0.60 g (4.3 mmol) of K$_2$CO$_3$ in 10 ml ACN is stirred at 70° C. over night. The reaction mixture is filtered over alumina/activated carbon. The solvent is removed in vacuo.

$C_9H_8BrF_2NO$ (M=264.1 g/mol)
ESI-MS: 264 [M+H]$^+$
R$_t$ (HPLC): 0.91 min (method A)

Example XVII

1-Bromo-4-cyclobutylmethoxy-benzene

The mixture of 2.50 g (14.5 mmol) of 4-bromophenol, 2.44 ml (21.7 mmol) of bromomethylcyclobutane and 7.99 g (57.8 mmol) of K$_2$CO$_3$ in 3 ml DMF is stirred at 100° C. over night. The reaction mixture is extracted with water and EtOAc. The organic layer is dried, filtered and the solvent is removed in vacuo.

$C_{11}H_{13}BrO$ (M=241.1 g/mol)
ESI-MS: 240 [M*$^+$]
R$_t$ (HPLC): 1.33 min (method A)

Example XVIII

2-Chloro-5-(2,2-diIfluoro-cyclopropylmethoxy)-pyrimidine

The mixture of 150 mg (1.15 mmol) of 2-chloro-5-hydroxypyrimidine, 295 mg (1.72 mmol) of 1-bromoethyl-2,2-difluorocyclopropane and 318 mg (2.30 mmol) of $K_2CO_3$ in 3 ml DMF is stirred at 80° C. over night. The reaction mixture is extracted with water and DCM. The organic layer is dried, filtered and the solvent is removed in vacuo. The residue is purified by prep. HPLC-MS (MeOH/$H_2O$/$NH_4OH$).

$C_8H_7ClF_2N_2O$ (M=220.1 g/mol)

ESI-MS: 221 [M+H]$^+$ $R_t$ (HPLC): 1.21 min (method G)

Example XIX

2-Ethoxy-4-iodo-pyridine

The mixture of 40.0 g (167 mmol) of 2-chloro-4-iodopyridine and 70.0 ml (188 mmol) of sodium ethoxide in 80 ml EtOH is stirred at reflux over night. The solvent is removed in vacuo. The residue is extracted with water and DCM. The organic layer is dried over $MgSO_4$, filtered and the solvent is removed in vacuo. The residue is purified by flash chromatography (silica gel, DCM).

$C_7H_8INO$ (M=249.1 g/mol)

ESI-MS: 250 [M+H]$^+$

PREPARATION OF FINAL COMPOUNDS

Example 1

Example 1.1 (General Route)

2-(4-(1-[5-Chloro-6-(2-hydroxy-2-methyl-propoxy)-pyrimidin-4-yl]-(R)-pyrrolidin-3-yloxy)-phenyl)-N-cyclopropyl-propionamide 4.4 mg (0.010 mmol) of example VIII are dissolved in 100 µL DMF, 5.2 µl (0.030 mmol) of DIPEA and 3.5 mg (0.010 mmol) TBTU are added. This mixture is stirred at r.t. for 10 min. Then a mixture of 0.6 mg (0.01 mmol) cyclopropylamine in 100 µl DMF is added and the reaction mixture is stirred at r.t. for 3 h. 13.3 µl (0.040 mmol) of 3 N aq. $K_2CO_3$ are added. After 20 min. the reaction mixture is filtered through a pad of basic alumina and eluted with DMF/MeOH (9/1). Removal of the solvent in vacuo yields the title compound.

$C_{24}H_{31}ClN_4O_4$ (M=475.0 g/mol)

ESI-MS: 475 [M+H]$^+$ $R_t$ (HPLC): 1.05 min (method H)

The following compounds are prepared analogously to example 1.1.

| Ex. | Starting material (acid) | Starting material (amine) †, ‡ | Structure | Mass spec result | HPLC retention time (method) |
|---|---|---|---|---|---|
| 1.1 | VIII | NH$_2$-cyclopropyl | 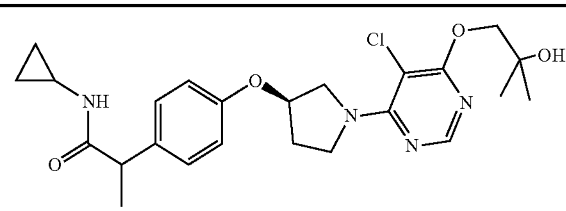 | 475 [M + H]$^+$ | 1.05 (H) |

-continued

| Ex. | Starting material (acid) | Starting material (amine) †, ‡ | Structure | Mass spec result | HPLC retention time (method) |
|---|---|---|---|---|---|
| 1.2 | VI | cyclopropylamine | 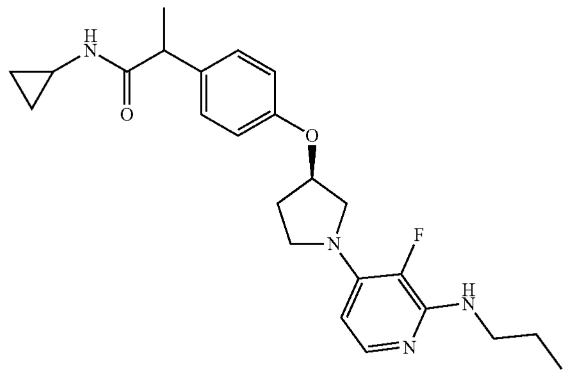 [SMILES: CCCNc1nccc(N2CC[C@@H](Oc3ccc(C(C)C(=O)NC4CC4)cc3)C2)c1F] | 427 [M + H]⁺ | 0.75 (H) |
| 1.3 | VI | 2-methylcyclopropylamine·HCl | 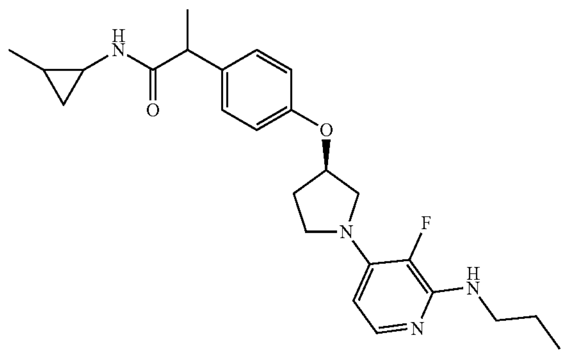 [SMILES: CCCNc1nccc(N2CC[C@@H](Oc3ccc(C(C)C(=O)NC4CC4C)cc3)C2)c1F] | 441 [M + H]⁺ | 0.80 (H) |
| 1.4* | VI | 2-methylcyclopropylamine | 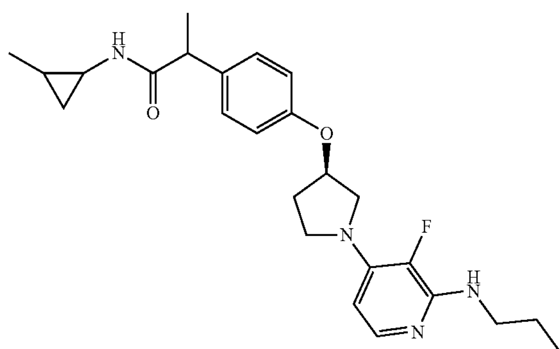 | 441 [M + H]⁺ | 0.81 (H) |
| 1.5 | VII | cyclopropylamine | 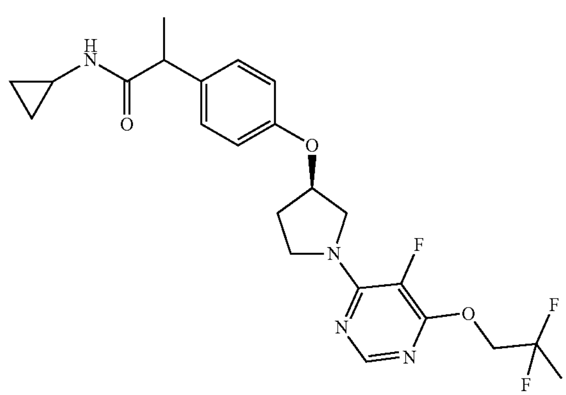 [SMILES: CC(C(=O)NC1CC1)c1ccc(O[C@@H]2CCN(c3ncnc(OCC(C)(F)F)c3F)C2)cc1] | 465 [M + H]⁺ | 1.20 (H) |

-continued

| Ex. | Starting material (acid) | Starting material (amine) †, ‡ | Structure | Mass spec result | HPLC retention time (method) |
|---|---|---|---|---|---|
| 1.6* | IX | 2-methylcyclopropylamine | 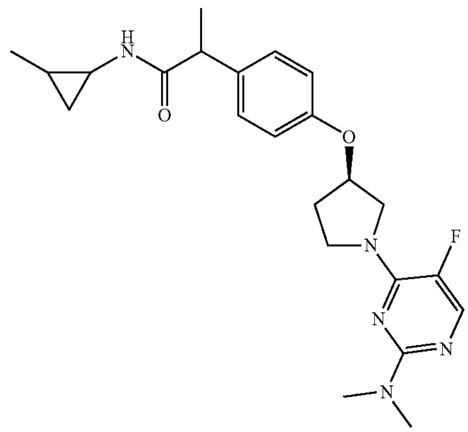 [SMILES: CC(C(=O)NC1CC1C)c1ccc(O[C@@H]2CCN(c3nc(N(C)C)ncc3F)C2)cc1] | 427 [M + H]+ | 0.77 (H) |
| 1.7 | IX | cyclopropylamine | 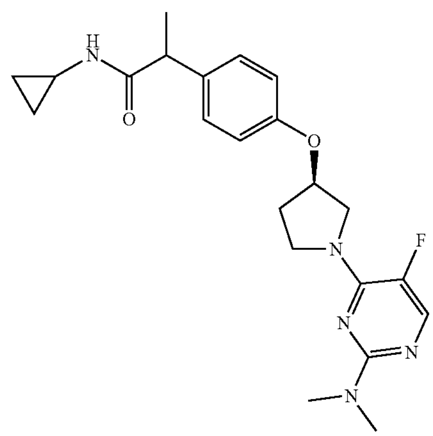 [SMILES: CC(C(=O)NC1CC1)c1ccc(O[C@@H]2CCN(c3nc(N(C)C)ncc3F)C2)cc1] | 414 [M + H]+ | 0.72 (H) |
| 1.8 | XI | cyclopropylamine | 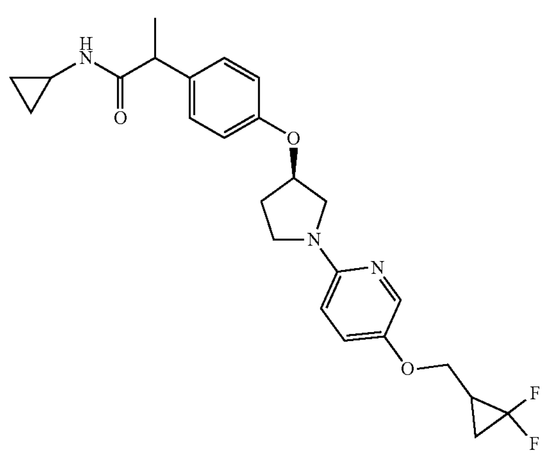 [SMILES: CC(C(=O)NC1CC1)c1ccc(O[C@@H]2CCN(c3ccc(OCC4CC4(F)F)cn3)C2)cc1] | 458 [M + H]+ | 0.77 (H) |

| Ex. | Starting material (acid) | Starting material (amine) †, ‡ | Structure | Mass spec result | HPLC retention time (method) |
|---|---|---|---|---|---|
| 1.9 | IX | cyclopropylamine·HCl (methyl-substituted) | (structure) | 428 [M + H]+ | 0.77 (H) |
| 1.10* | XI | methylcyclopropylamine | (structure) | 472 [M + H]+ | 0.83 (H) |
| 1.11 | VI | ethylamine·HCl | (structure) | 415 [M + H]+ | 0.74 (H) |

| Ex. | Starting material (acid) | Starting material (amine) †, ‡ | Structure | Mass spec result | HPLC retention time (method) |
|---|---|---|---|---|---|
| 1.12 | XI | NH₂-cyclopropyl-methyl · ClH | 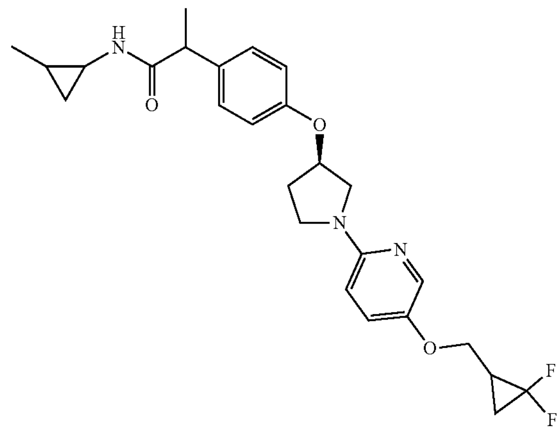 [SMILES: CC(C(=O)NC1CC1C)c1ccc(O[C@@H]2CCN(c3ccc(OCC4CC4(F)F)cn3)C2)cc1] | 472 [M + H]⁺ | 0.82 (H) |
| 1.13* | VIII | NH₂-cyclopropyl-methyl | 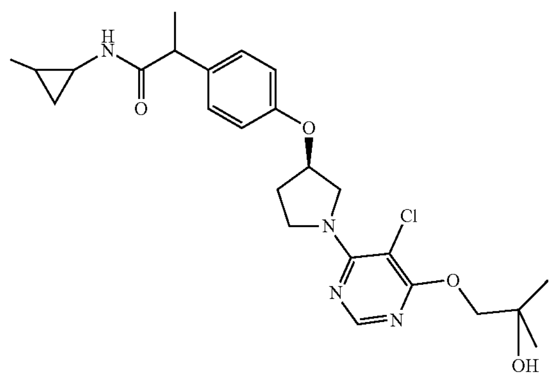 [SMILES: CC(C(=O)NC1CC1C)c1ccc(O[C@@H]2CCN(c3ncnc(OCC(C)(C)O)c3Cl)C2)cc1] | 489 [M + H]⁺ | 1.13 (H) |
| 1.14* | VII | NH₂-cyclopropyl-methyl | 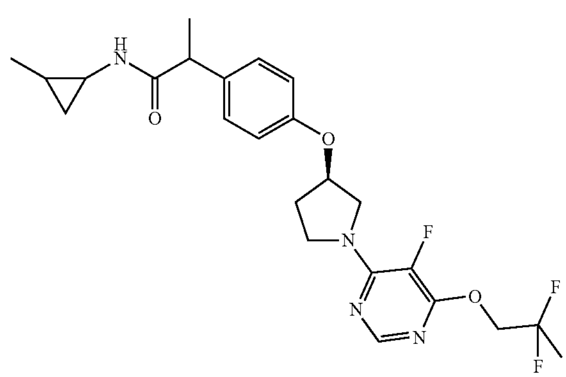 [SMILES: CC(C(=O)NC1CC1C)c1ccc(O[C@@H]2CCN(c3ncnc(OCC(C)(F)F)c3F)C2)cc1] | 479 [M + H]⁺ | 1.26 (H) |

-continued

| Ex. | Starting material (acid) | Starting material (amine) †, ‡ | Structure | Mass spec result | HPLC retention time (method) |
|---|---|---|---|---|---|
| 1.15 | XI | F-CH(F)-CH2-NH2 | (structure) | 482 [M + H]+ | 0.80 (H) |
| 1.16 | VI | HC≡C-CH2-NH2 · ClH | (structure) | 425 [M + H]+ | 0.77 (H) |
| 1.17 | VIII | CH3CH2-NH2 · ClH | (structure) | 463 [M + H]+ | 1.05 (H) |

| Ex. | Starting material (acid) | Starting material (amine) †, ‡ | Structure | Mass spec result | HPLC retention time (method) |
|---|---|---|---|---|---|
| 1.18 | VI | | 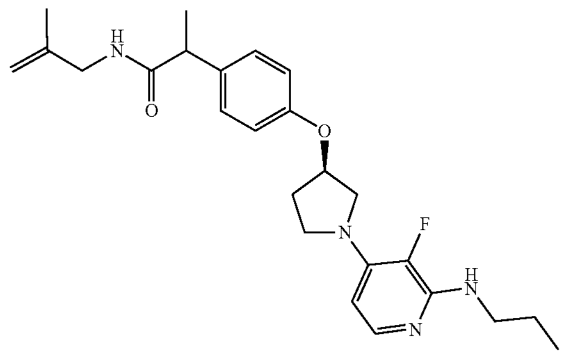 [SMILES: C=C(C)CNC(=O)C(C)c1ccc(O[C@@H]2CCN(c3ccnc(NCCC)c3F)C2)cc1] | 441 [M + H]+ | 0.82 (H) |
| 1.19 | VI | | 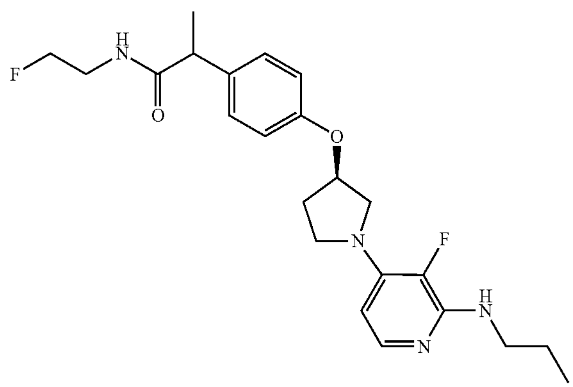 [SMILES: CCCNc1nccc(N2CC[C@@H](Oc3ccc(C(C)C(=O)NCCF)cc3)C2)c1F] | 433 [M + H]+ | 0.74 (H) |
| 1.20 | VIII | | 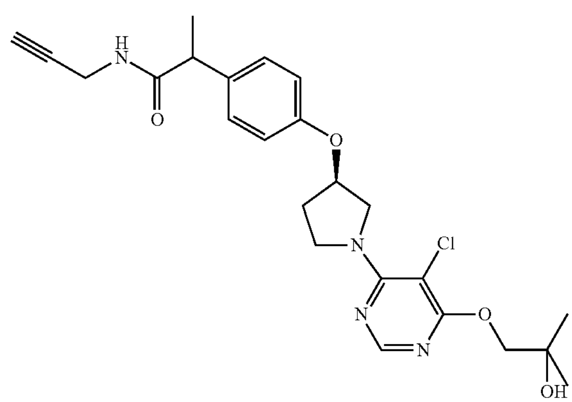 [SMILES: C#CCNC(=O)C(C)c1ccc(O[C@@H]2CCN(c3ncnc(OCC(C)(C)O)c3Cl)C2)cc1] | 473 [M + H]+ | 1.07 (H) |
| 1.21 | VI | | 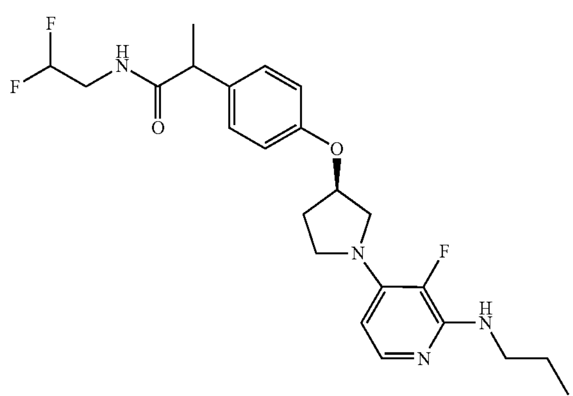 [SMILES: CCCNc1nccc(N2CC[C@@H](Oc3ccc(C(C)C(=O)NCC(F)F)cc3)C2)c1F] | 451 [M + H]+ | 0.78 (H) |

-continued

| Ex. | Starting material (acid) | Starting material (amine) †, ‡ | Structure | Mass spec result | HPLC retention time (method) |
|---|---|---|---|---|---|
| 1.22 | VII | NH₂-(2-methylcyclopropyl)·ClH | 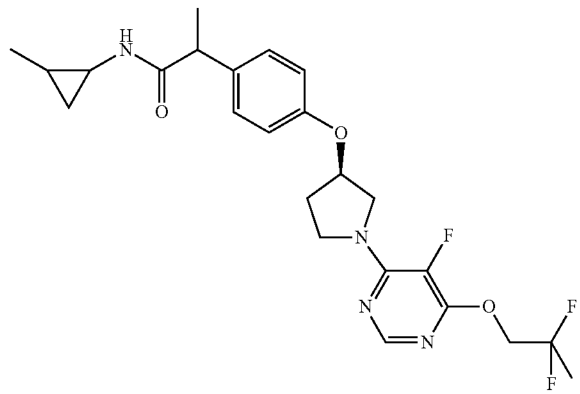 [SMILES: CC(C(=O)NC1CC1C)c1ccc(O[C@@H]2CCN(c3ncnc(OCC(C)(F)F)c3F)C2)cc1] | 479 [M + H]⁺ | 1.26 (H) |
| 1.23 | VIII | 2-methylallylamine | 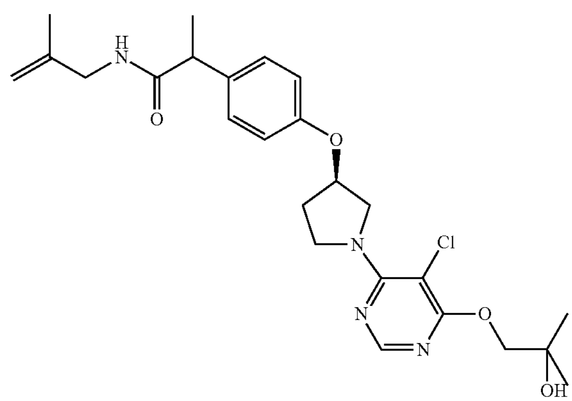 [SMILES: C=C(C)CNC(=O)C(C)c1ccc(O[C@@H]2CCN(c3ncnc(OCC(C)(C)O)c3Cl)C2)cc1] | 489 [M + H]⁺ | 1.14 (H) |
| 1.24 | VI | isopropylamine | 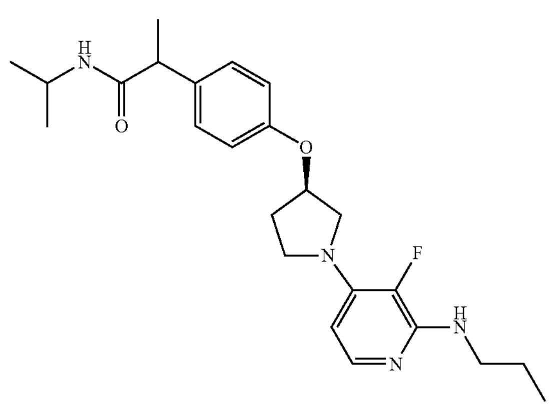 [SMILES: CCCNc1nccc(N2CC[C@@H](Oc3ccc(C(C)C(=O)NC(C)C)cc3)C2)c1F] | 429 [M + H]⁺ | 0.78 (H) |

-continued

| Ex. | Starting material (acid) | Starting material (amine) †, ‡ | Structure | Mass spec result | HPLC retention time (method) |
|---|---|---|---|---|---|
| 1.25 | VIII | allylamine | 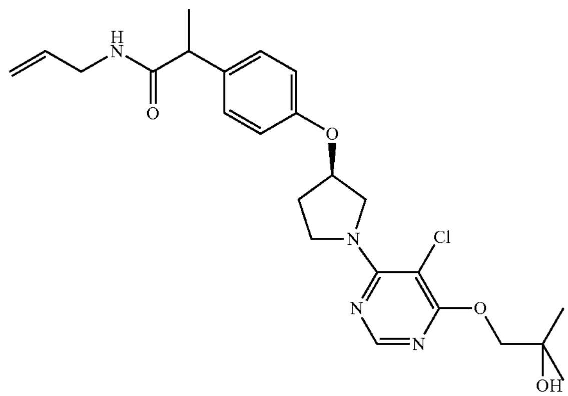 [SMILES: C=CCNC(=O)C(C)c1ccc(O[C@@H]2CCN(c3ncnc(OCC(C)(C)O)c3Cl)C2)cc1] | 475 [M + H]⁺ | 1.09 (H) |
| 1.26 | VIII | 2-methylcyclopropylamine · ClH | 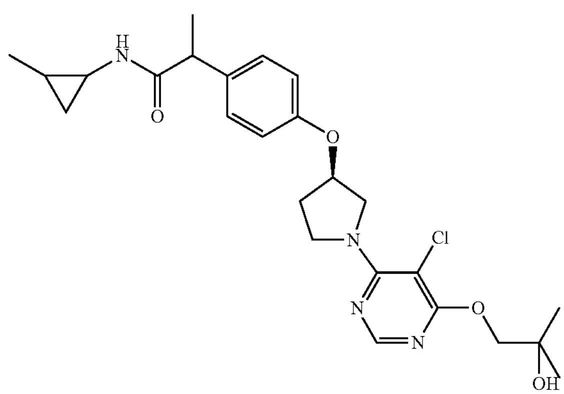 [SMILES: CC(C(=O)NC1CC1C)c1ccc(O[C@@H]2CCN(c3ncnc(OCC(C)(C)O)c3Cl)C2)cc1] | 489 [M + H]⁺ | 1.13 (H) |
| 1.27 | IX | ethylamine · ClH | 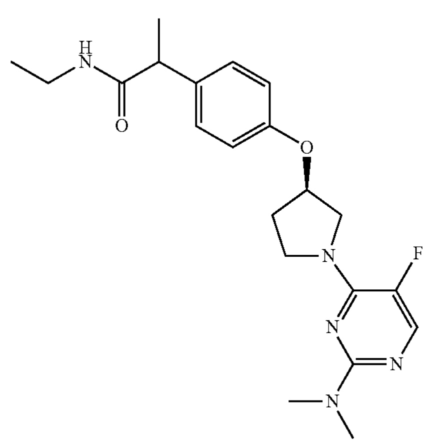 [SMILES: CCNC(=O)C(C)c1ccc(O[C@@H]2CCN(c3nc(N(C)C)ncc3F)C2)cc1] | 402 [M + H]⁺ | 0.71 (H) |

-continued

| Ex. | Starting material (acid) | Starting material (amine) †, ‡ | Structure | Mass spec result | HPLC retention time (method) |
|---|---|---|---|---|---|
| 1.28 | XI | CH₃NH₂ · ClH | 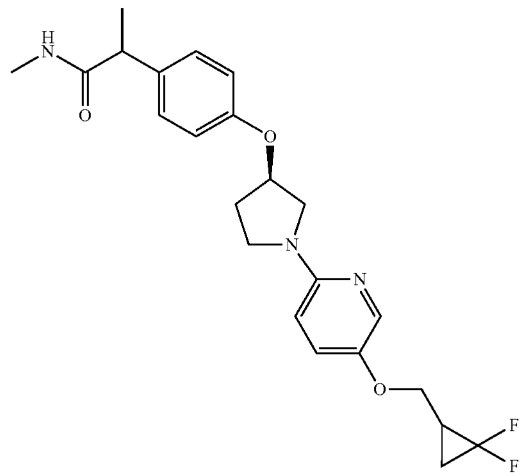 [SMILES: CNC(=O)C(C)c1ccc(O[C@@H]2CCN(c3ccc(OCC4CC4(F)F)cn3)C2)cc1] | 432 [M + H]⁺ | 0.73 (H) |
| 1.29 | VI | (S)-sec-butylamine | 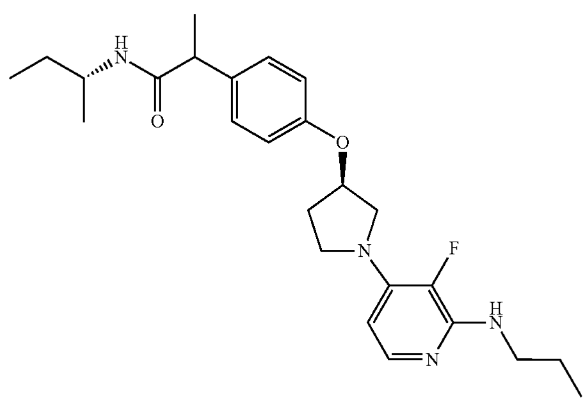 [SMILES: CCCNc1nccc(N2CC[C@@H](Oc3ccc(C(C)C(=O)N[C@H](C)CC)cc3)C2)c1F] | 443 [M + H]⁺ | 0.82 (H) |
| 1.30 | VIII | CH₃CH₂NH₂ · ClH | 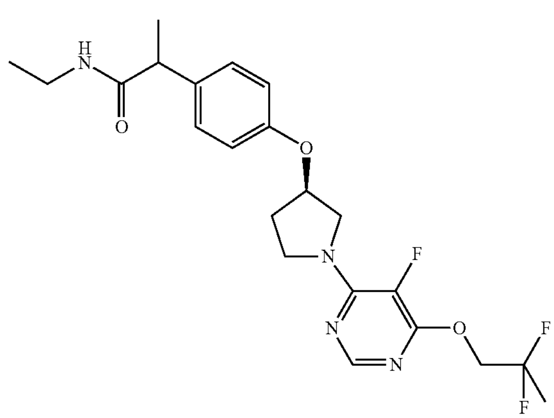 [SMILES: CCNC(=O)C(C)c1ccc(O[C@@H]2CCN(c3ncnc(OCC(C)(F)F)c3F)C2)cc1] | 453 [M + H]⁺ | 1.20 (H) |

-continued

| Ex. | Starting material (acid) | Starting material (amine) †, ‡ | Structure | Mass spec result | HPLC retention time (method) |
|---|---|---|---|---|---|
| 1.31 | XI | allyl-NH₂ | (structure) | 458 [M + H]⁺ | 0.80 (H) |
| 1.32 | VI | propyl-NH₂ · ClH | (structure) | 429 [M + H]⁺ | 0.78 (H) |
| 1.33 | VI | allyl-NH₂ | (structure) | 427 [M + H]⁺ | 0.78 (H) |

| Ex. | Starting material (acid) | Starting material (amine) †, ‡ | Structure | Mass spec result | HPLC retention time (method) |
|---|---|---|---|---|---|
| 1.34 | VIII | CH₃NH₂ ClH | 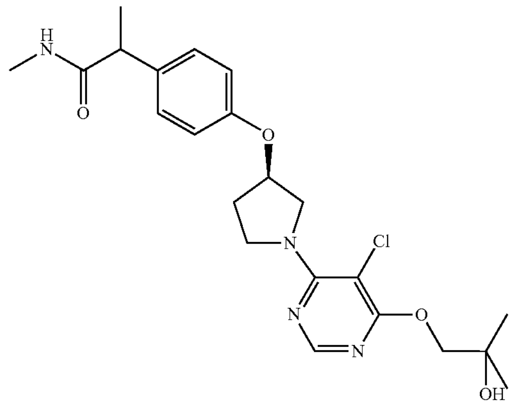 [SMILES: CNC(=O)C(C)c1ccc(O[C@@H]2CCN(c3ncnc(OCC(C)(C)O)c3Cl)C2)cc1] | 449 [M + H]⁺ | 0.99 (H) |
| 1.35 | VI | 3-aminopyridine | 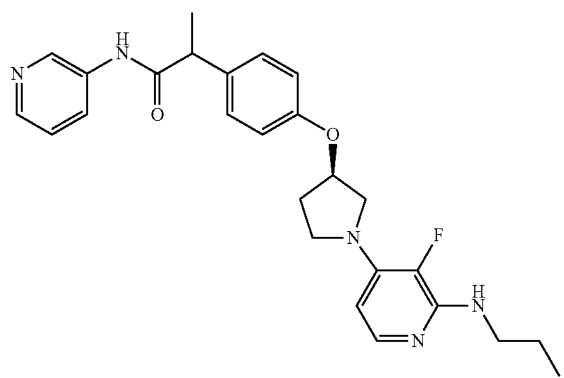 [SMILES: CCCNc1nccc(N2CC[C@@H](Oc3ccc(C(C)C(=O)Nc4cccnc4)cc3)C2)c1F] | | 0.64 (H) |
| 1.36 | VIII | 2,2-difluoroethylamine | 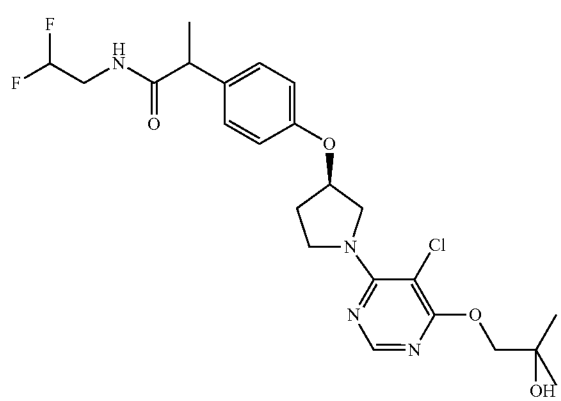 [SMILES: CC(C(=O)NCC(F)F)c1ccc(O[C@@H]2CCN(c3ncnc(OCC(C)(C)O)c3Cl)C2)cc1] | 499 [M + H]⁺ | 1.10 (H) |

-continued

| Ex. | Starting material (acid) | Starting material (amine) †, ‡ | Structure | Mass spec result | HPLC retention time (method) |
|---|---|---|---|---|---|
| 1.37 | XI | ![methallylamine] | 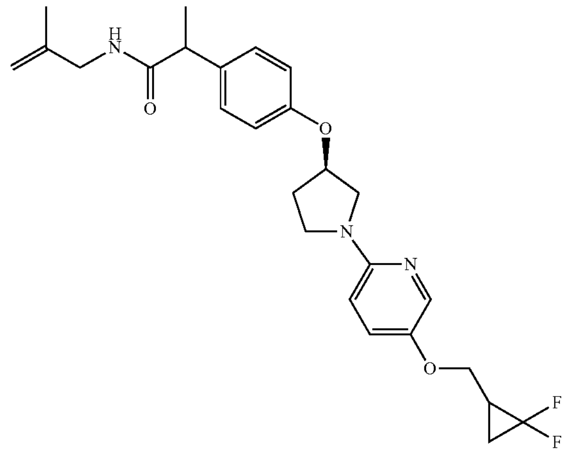 [SMILES: C=C(C)CNC(=O)C(C)c1ccc(O[C@@H]2CCN(c3ccc(OCC4CC4(F)F)cn3)C2)cc1] | 472 [M + H]⁺ | 0.84 (H) |
| 1.38 | VI | 2,2,2-trifluoroethylamine | 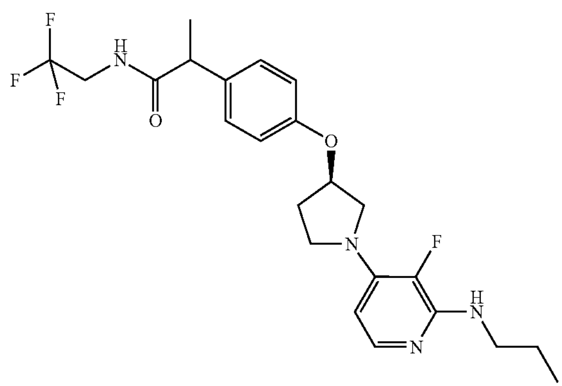 [SMILES: CCCNc1nccc(N2CC[C@@H](Oc3ccc(C(C)C(=O)NCC(F)(F)F)cc3)C2)c1F] | 469 [M + H]⁺ | 0.83 (H) |
| 1.39 | XI | 2-fluoroethylamine·ClH | 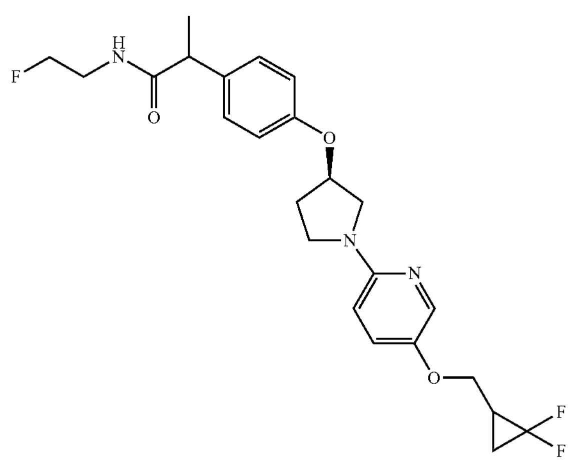 [SMILES: CC(C(=O)NCCF)c1ccc(O[C@@H]2CCN(c3ccc(OCC4CC4(F)F)cn3)C2)cc1] | 464 [M + H]⁺ | 0.77 (H) |

-continued

| Ex. | Starting material (acid) | Starting material (amine) †, ‡ | Structure | Mass spec result | HPLC retention time (method) |
|---|---|---|---|---|---|
| 1.40 | VIII | propylamine · ClH | N-propyl amide with 4-phenoxy, (S)-pyrrolidinyl, 5-chloro-6-(2-hydroxy-2-methylpropoxy)pyrimidine | 477 [M + H]⁺ | 1.11 (H) |
| 1.41 | VI | cyclobutylamine | N-cyclobutyl amide with 4-phenoxy, (S)-pyrrolidinyl, 3-fluoro-2-(propylamino)pyridine | 441 [M + H]⁺ | 0.81 (H) |
| 1.42 | VII | propargylamine · ClH | N-propargyl amide with 4-phenoxy, (S)-pyrrolidinyl, 5-fluoro-6-(2,2,2-trifluoroethoxy)pyrimidine | 463 [M + H]⁺ | 1.21 (H) |

-continued

| Ex. | Starting material (acid) | Starting material (amine) †, ‡ | Structure | Mass spec result | HPLC retention time (method) |
|---|---|---|---|---|---|
| 1.43 | IX | F-CH(F)-CH2-NH2 | (structure) | 438 [M + H]+ | 0.74 (H) |
| 1.44 | IX | CH2=C(CH3)-CH2-NH2 | (structure) | 428 [M + H]+ | 0.78 (H) |
| 1.45 | VII | CH2=CH-CH2-NH2 | (structure) | 465 [M + H]+ | 1.23 (H) |

-continued

| Ex. | Starting material (acid) | Starting material (amine) †, ‡ | Structure | Mass spec result | HPLC retention time (method) |
|---|---|---|---|---|---|
| 1.46 | VII | | 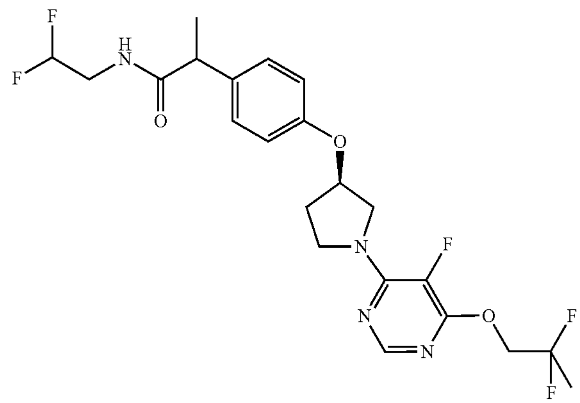 [SMILES: CC(C(=O)NCC(F)F)c1ccc(O[C@@H]2CCN(c3ncnc(OCC(C)(F)F)c3F)C2)cc1] | 489 [M + H]⁺ | 1.23 (H) |
| 1.47 | VIII | | 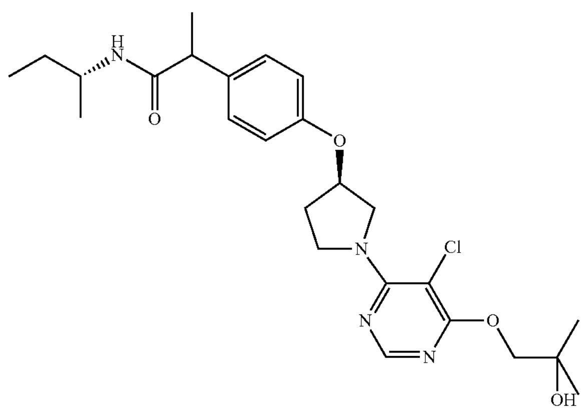 [SMILES: CC[C@@H](C)NC(=O)C(C)c1ccc(O[C@@H]2CCN(c3ncnc(OCC(C)(C)O)c3Cl)C2)cc1] | 491 [M + H]⁺ | 1.16 (H) |
| 1.48 | VII | | 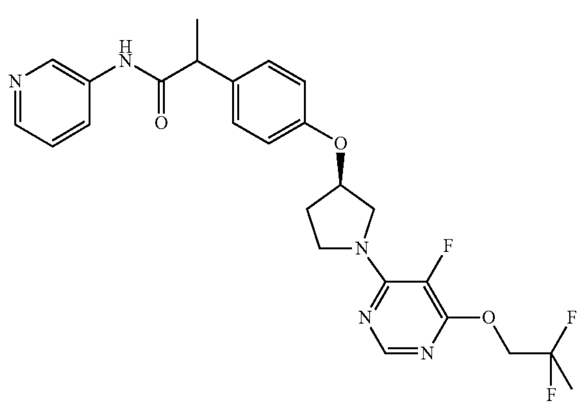 [SMILES: CC(C(=O)Nc1cccnc1)c1ccc(O[C@@H]2CCN(c3ncnc(OCC(C)(F)F)c3F)C2)cc1] | 502 [M + H]⁺ | 0.91 (H) |

|Ex.|Starting material (acid)|Starting material (amine) †, ‡|Structure|Mass spec result|HPLC retention time (method)|
|---|---|---|---|---|---|
|1.49|VIII|isopropylamine|(structure)|477 [M + H]+|1.11 (H)|
|1.50|VIII|cyclobutylamine|(structure)|489 [M + H]+|1.14 (H)|
|1.51|IX|2-fluoroethylamine ClH|(structure)|420 [M + H]+|0.71 (H)|

-continued

| Ex. | Starting material (acid) | Starting material (amine) †, ‡ | Structure | Mass spec result | HPLC retention time (method) |
|---|---|---|---|---|---|
| 1.52 | XI | propylamine·HCl | (structure) | 460 [M + H]+ | 0.81 (H) |
| 1.53 | VII | 2-methylallylamine | (structure) | 479 [M + H]+ | 1.27 (H) |
| 1.54 | VIII | 2-fluoroethylamine·HCl | (structure) | 481 [M + H]+ | 1.04 (H) |

-continued

| Ex. | Starting material (acid) | Starting material (amine) †, ‡ | Structure | Mass spec result | HPLC retention time (method) |
|---|---|---|---|---|---|
| 1.55 | VII | F-CH₂CH₂-NH₂ · ClH | (2-fluoroethyl amide of 2-(4-{[pyrrolidin-3-yl]oxy}phenyl)propanamide, pyrrolidine N-linked to 5-fluoro-6-(2,2,2-trifluoroethoxy)pyrimidin-4-yl) | 471 [M + H]⁺ | 1.19 (H) |
| 1.56 | IX | CH₃-NH₂ · ClH | (N-methyl amide of 2-(4-{[pyrrolidin-3-yl]oxy}phenyl)propanamide, pyrrolidine N-linked to 2-(dimethylamino)-5-fluoropyrimidin-4-yl) | 388 [M + H]⁺ | 0.97 (H) |
| 1.57 | XI | (S)-H₂N-CH(CH₃)-CH₂OH | ((S)-1-hydroxypropan-2-yl amide of 2-(4-{[pyrrolidin-3-yl]oxy}phenyl)propanamide, pyrrolidine N-linked to 5-{[2,2-difluorocyclopropyl]methoxy}pyrimidin-2-yl) | 476 [M + H]⁺ | 0.72 (H) |

| Ex. | Starting material (acid) | Starting material (amine) †, ‡ | Structure | Mass spec result | HPLC retention time (method) |
|---|---|---|---|---|---|
| 1.58 | XI | | 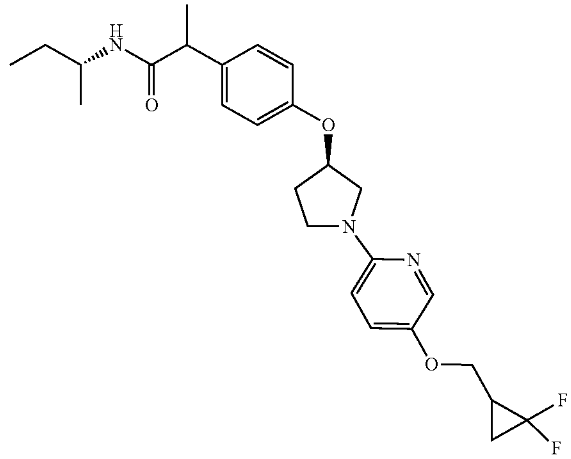 [SMILES: CC[C@@H](C)NC(=O)C(C)c1ccc(O[C@@H]2CCN(c3ccc(OCC4CC4(F)F)cn3)C2)cc1] | 474 [M + H]+ | 0.84 (H) |
| 1.59 | VII | | 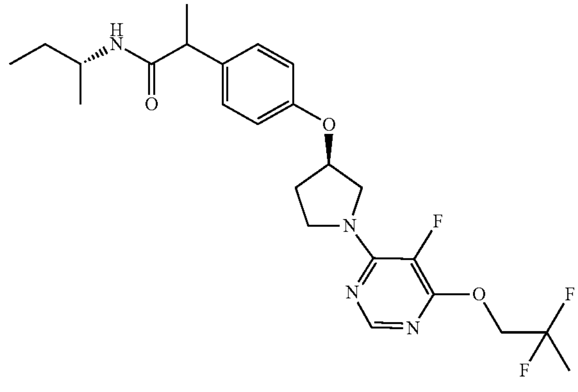 [SMILES: CC[C@@H](C)NC(=O)C(C)c1ccc(O[C@@H]2CCN(c3ncnc(OCC(C)(F)F)c3F)C2)cc1] | 481 [M + H]+ | 1.29 (H) |
| 1.60 | IX | | 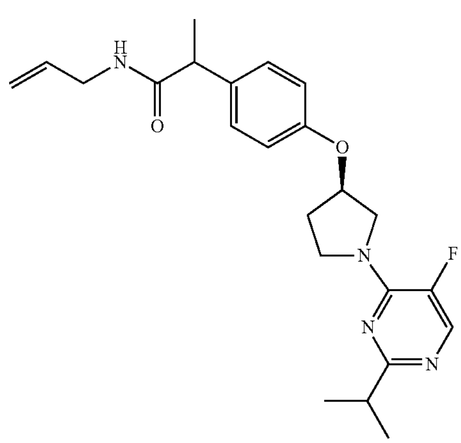 [SMILES: C=CCNC(=O)C(C)c1ccc(O[C@@H]2CCN(c3nc(C(C)C)ncc3F)C2)cc1] | 414 [M + H]+ | 0.74 (H) |

| Ex. | Starting material (acid) | Starting material (amine) †, ‡ | Structure | Mass spec result | HPLC retention time (method) |
|---|---|---|---|---|---|
| 1.61 | VI | oxetan-3-amine ClH | 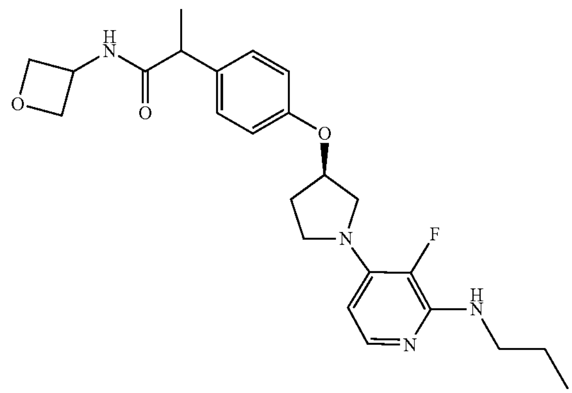 [SMILES: CCCNc1nccc(N2CC[C@@H](Oc3ccc(C(C)C(=O)NC4COC4)cc3)C2)c1F] | 443 [M + H]+ | 0.70 (H) |
| 1.62 | XI | 2,2,2-trifluoroethylamine | 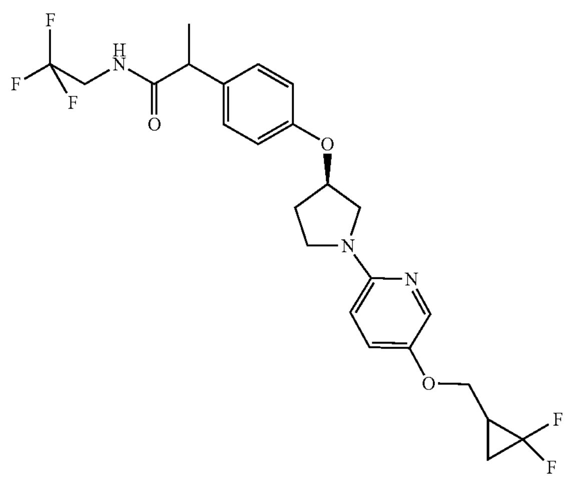 [SMILES: CC(C(=O)NCC(F)(F)F)c1ccc(O[C@@H]2CCN(c3ccc(OCC4CC4(F)F)cn3)C2)cc1] | 500 [M + H]+ | 0.85 (H) |
| 1.63 | XI | isopropylamine | 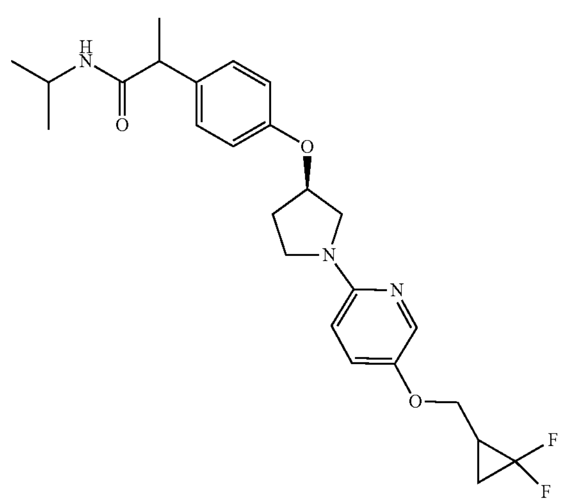 [SMILES: CC(C)NC(=O)C(C)c1ccc(O[C@@H]2CCN(c3ccc(OCC4CC4(F)F)cn3)C2)cc1] | 460 [M + H]+ | 0.80 (H) |

| Ex. | Starting material (acid) | Starting material (amine) †, ‡ | Structure | Mass spec result | HPLC retention time (method) |
|---|---|---|---|---|---|
| 1.64 | VII | F₃C-CH₂-NH₂ (2,2,2-trifluoroethylamine derivative with extra F) | 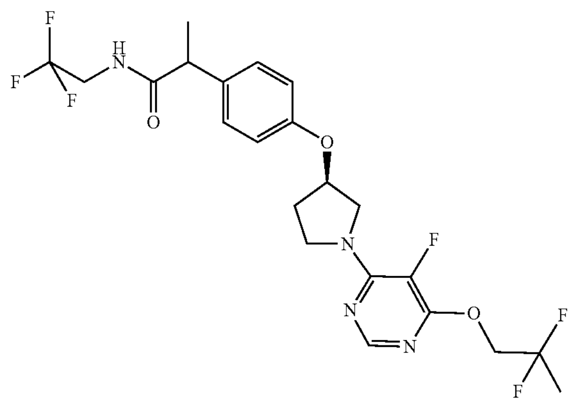 [SMILES: CC(C(=O)NCC(F)(F)F)c1ccc(O[C@@H]2CCN(c3ncnc(OCC(C)(F)F)c3F)C2)cc1] | 507 [M + H]⁺ | 1.28 (H) |
| 1.65 | IX | propylamine·HCl | 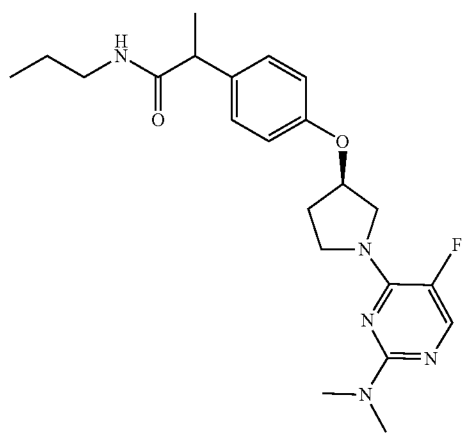 [SMILES: CCCNC(=O)C(C)c1ccc(O[C@@H]2CCN(c3nc(N(C)C)ncc3F)C2)cc1] | 416 [M + H]⁺ | 0.75 (H) |
| 1.66 | VII | cyclobutylamine | 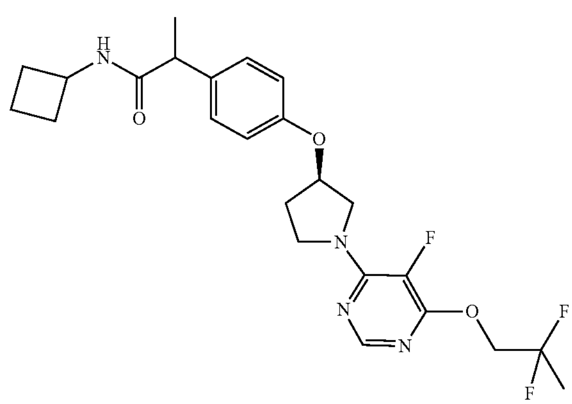 [SMILES: CC(C(=O)NC1CCC1)c1ccc(O[C@@H]2CCN(c3ncnc(OCC(C)(F)F)c3F)C2)cc1] | 479 [M + H]⁺ | 1.27 (H) |

-continued

| Ex. | Starting material (acid) | Starting material (amine) †, ‡ | Structure | Mass spec result | HPLC retention time (method) |
|---|---|---|---|---|---|
| 1.67 | XI | oxetan-3-amine ·ClH | 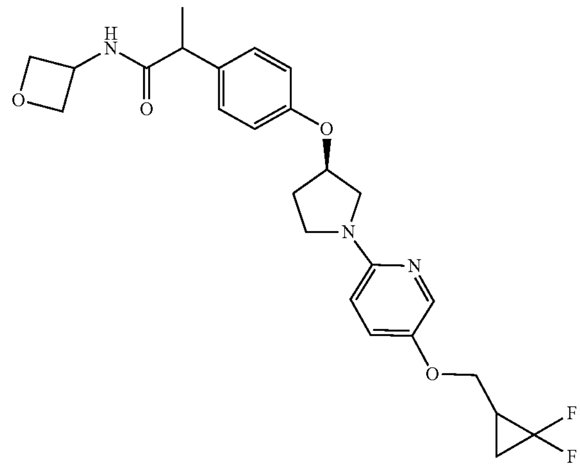 [SMILES: CC(C(=O)NC1COC1)c1ccc(O[C@@H]2CCN(c3ccc(OCC4CC4(F)F)cn3)C2)cc1] | 474 [M + H]+ | 0.73 (H) |
| 1.68 | IX | oxetan-3-amine ·ClH | 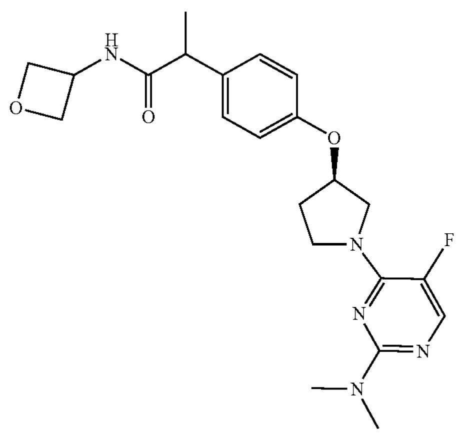 [SMILES: CC(C(=O)NC1COC1)c1ccc(O[C@@H]2CCN(c3nc(N(C)C)ncc3F)C2)cc1] | 430 [M + H]+ | 0.67 (H) |
| 1.69 | IX | 2,2,2-trifluoroethylamine | 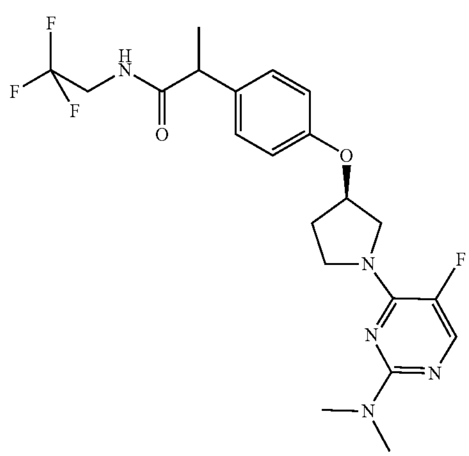 [SMILES: CC(C(=O)NCC(F)(F)F)c1ccc(O[C@@H]2CCN(c3nc(N(C)C)ncc3F)C2)cc1] | 456 [M + H]+ | 0.80 (H) |

-continued

| Ex. | Starting material (acid) | Starting material (amine) †, ‡ | Structure | Mass spec result | HPLC retention time (method) |
|---|---|---|---|---|---|
| 1.70 | XI | 5-aminopyrimidine | 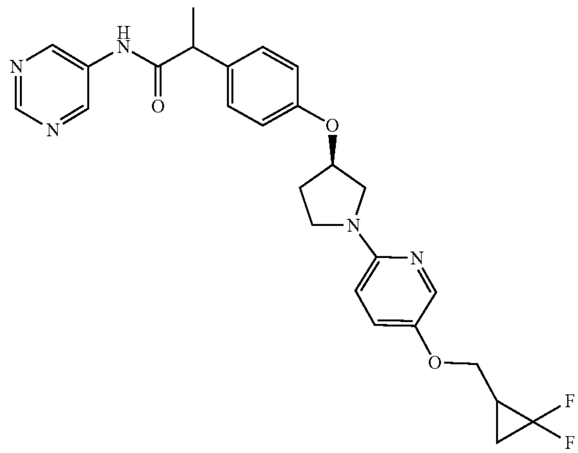 [SMILES: CC(C(=O)Nc1cncnc1)c1ccc(O[C@@H]2CCN(c3ccc(OCC4CC4(F)F)cn3)C2)cc1] | 496 [M + H]+ | 0.78 (H) |
| 1.71 | VI | but-3-en-1-amine | 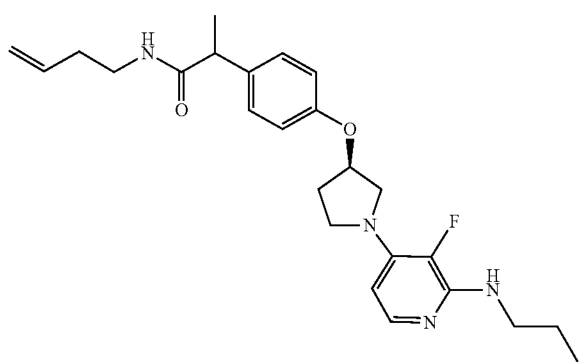 [SMILES: C=CCCNC(=O)C(C)c1ccc(O[C@@H]2CCN(c3ccnc(NCCC)c3F)C2)cc1] | 441 [M + H]+ | 0.81 (H) |
| 1.72 | VI | (S)-2-aminopropan-1-ol | 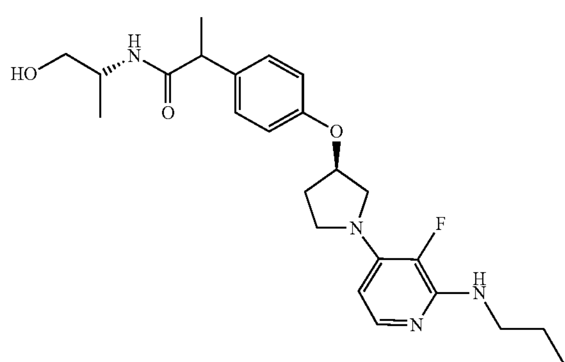 | 445 [M + H]+ | 0.69 (H) |

-continued

| Ex. | Starting material (acid) | Starting material (amine) †, ‡ | Structure | Mass spec result | HPLC retention time (method) |
|---|---|---|---|---|---|
| 1.73 | XI | ethyl(methyl)amine | 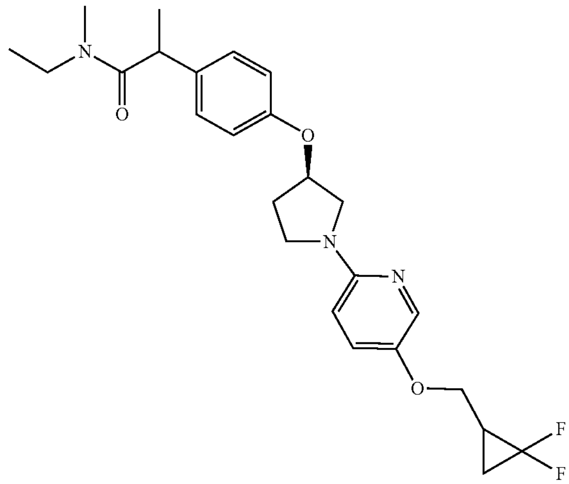 [SMILES: CCN(C)C(=O)C(C)c1ccc(O[C@@H]2CCN(c3ccc(OCC4CC4(F)F)cn3)C2)cc1] | 460 [M + H]+ | 0.81 (H) |
| 1.74 | VIII | 2,2,2-trifluoroethylamine | 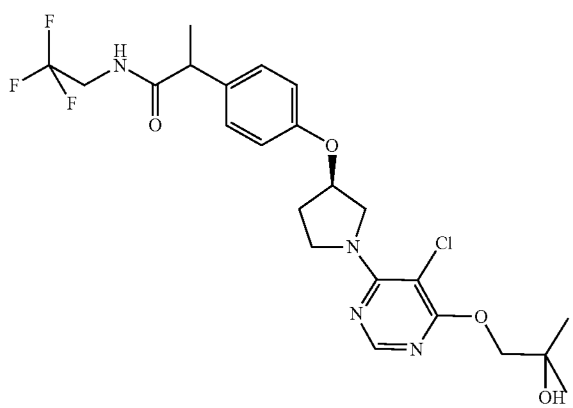 [SMILES: CC(C(=O)NCC(F)(F)F)c1ccc(O[C@@H]2CCN(c3ncnc(OCC(C)(C)O)c3Cl)C2)cc1] | 517 [M + H]+ | 1.15 (H) |
| 1.75 | VII | propylamine ClH | 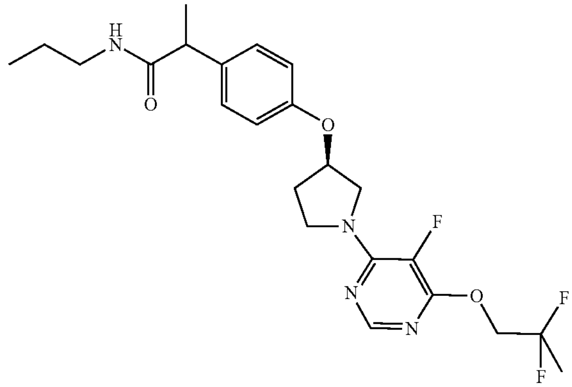 [SMILES: CCCNC(=O)C(C)c1ccc(O[C@@H]2CCN(c3ncnc(OCC(C)(F)F)c3F)C2)cc1] | 467 [M + H]+ | 1.25 (H) |

| Ex. | Starting material (acid) | Starting material (amine) †, ‡ | Structure | Mass spec result | HPLC retention time (method) |
|---|---|---|---|---|---|
| 1.76 | VII | H₂N-CH(CH₃)-CH₂OH (S) | (structure) | 483 [M + H]⁺ | 1.09 (H) |
| 1.77 | IX | H₂N-CH(CH₃)-CH₂OH (S) | (structure) | 432 [M + H]⁺ | 0.65 (H) |
| 1.78 | IX | cyclobutyl-NH₂ | (structure) | 428 [M + H]⁺ | 0.78 (H) |

-continued

| Ex. | Starting material (acid) | Starting material (amine) †, ‡ | Structure | Mass spec result | HPLC retention time (method) |
|---|---|---|---|---|---|
| 1.79 | XI | isobutylamine | 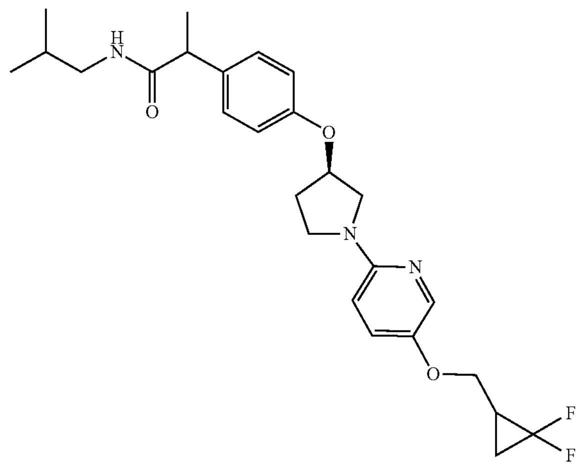 [SMILES: CC(C)CNC(=O)C(C)c1ccc(O[C@@H]2CCN(c3ccc(OCC4CC4(F)F)cn3)C2)cc1] | 474 [M + H]+ | 0.86 (H) |
| 1.80 | VII | isopropylamine | 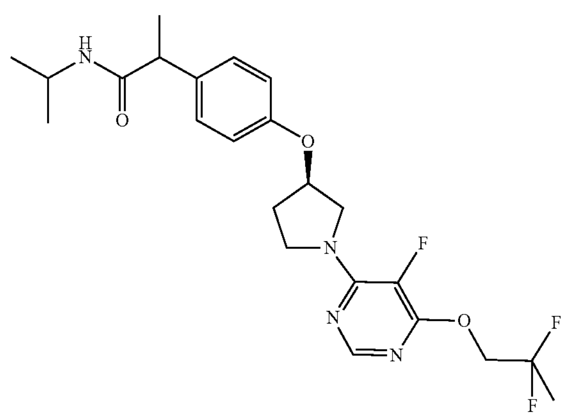 [SMILES: CC(C)NC(=O)C(C)c1ccc(O[C@@H]2CCN(c3ncnc(OCC(C)(F)F)c3F)C2)cc1] | 467 [M + H]+ | 1.25 (H) |
| 1.81 | IX | isopropylamine | 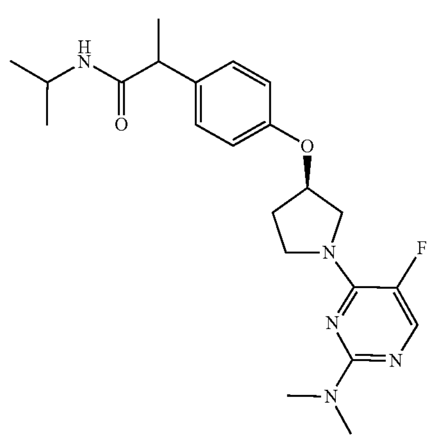 [SMILES: CC(C)NC(=O)C(C)c1ccc(O[C@@H]2CCN(c3nc(N(C)C)ncc3F)C2)cc1] | 416 [M + H]+ | 0.75 (H) |

-continued

| Ex. | Starting material (acid) | Starting material (amine) †, ‡ | Structure | Mass spec result | HPLC retention time (method) |
|---|---|---|---|---|---|
| 1.82 | XI | cyclobutyl-NH₂ | 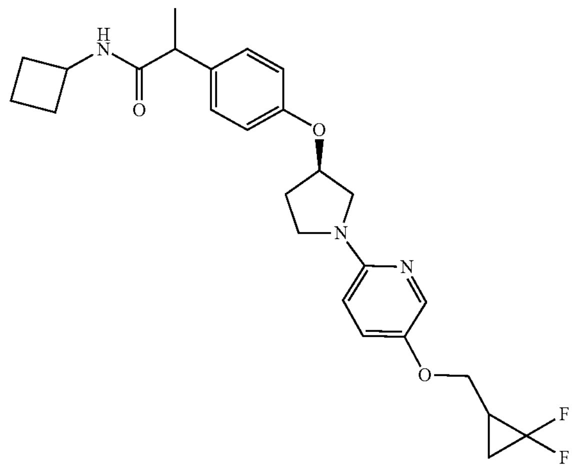 [SMILES: CC(C(=O)NC1CCC1)c1ccc(O[C@@H]2CCN(c3ccc(OCC4CC4(F)F)cn3)C2)cc1] | 472 [M + H]⁺ | 0.83 (H) |
| 1.83 | VIII | cyclopropylmethyl-NH₂ | 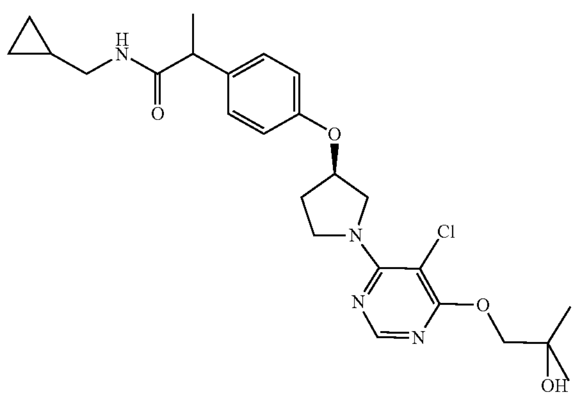 [SMILES: CC(C(=O)NCC1CC1)c1ccc(O[C@@H]2CCN(c3ncnc(OCC(C)(C)O)c3Cl)C2)cc1] | 489 [M + H]⁺ | 1.13 (H) |
| 1.84 | XI | NC-CH₂-CH(CH₃)-NH₂·HCl | 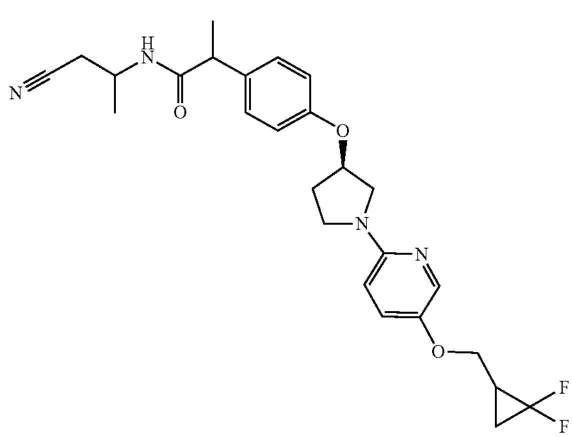 [SMILES: CC(CC#N)NC(=O)C(C)c1ccc(O[C@@H]2CCN(c3ccc(OCC4CC4(F)F)cn3)C2)cc1] | 485 [M + H]⁺ | 0.78 (H) |

| Ex. | Starting material (acid) | Starting material (amine) †, ‡ | Structure | Mass spec result | HPLC retention time (method) |
|---|---|---|---|---|---|
| 1.85 | VIII | oxetan-3-ylmethylamine | [structure] | 505 [M + H]+ | 0.97 (H) |
| 1.86 | XI | 3-aminopropan-1-ol | [structure] | 476 [M + H]+ | 0.71 (H) |
| 1.87 | VII | N-(4-(aminomethyl)thiazol-2-yl)acetamide | [structure] | 579 [M + H]+ | 1.13 (H) |

| Ex. | Starting material (acid) | Starting material (amine) †, ‡ | Structure | Mass spec result | HPLC retention time (method) |
|---|---|---|---|---|---|
| 1.88 | XI | | 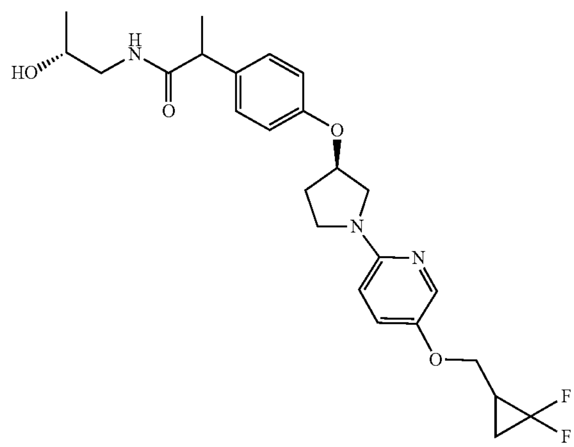 [SMILES: CC(C(=O)NC[C@@H](C)O)c1ccc(O[C@@H]2CCN(c3ccc(OCC4CC4(F)F)cn3)C2)cc1] | 476 [M + H]⁺ | 0.71 (H) |
| 1.89 | XI | | 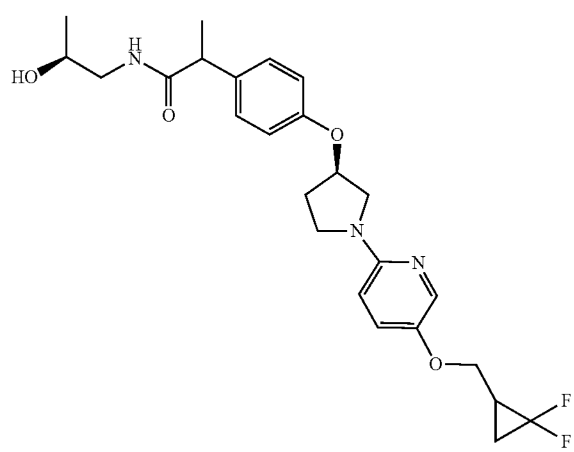 [SMILES: CC(C(=O)NC[C@H](C)O)c1ccc(O[C@@H]2CCN(c3ccc(OCC4CC4(F)F)cn3)C2)cc1] | 476 [M + H]⁺ | 0.71 (H) |
| 1.90 | VI | | 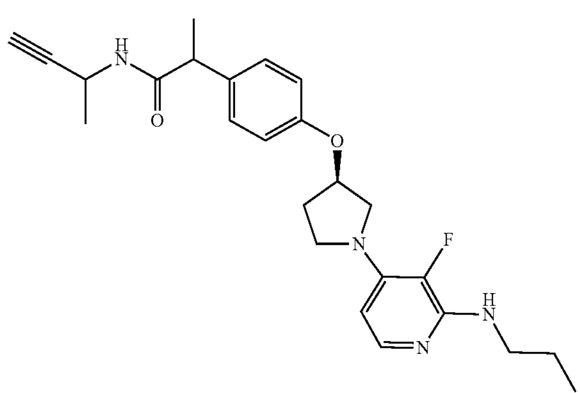 [SMILES: C#CC(C)NC(=O)C(C)c1ccc(O[C@@H]2CCN(c3ccnc(NCCC)c3F)C2)cc1] | 439 [M + H]⁺ | 0.81 (H) |

-continued

| Ex. | Starting material (acid) | Starting material (amine) †, ‡ | Structure | Mass spec result | HPLC retention time (method) |
|---|---|---|---|---|---|
| 1.91 | VIII | | 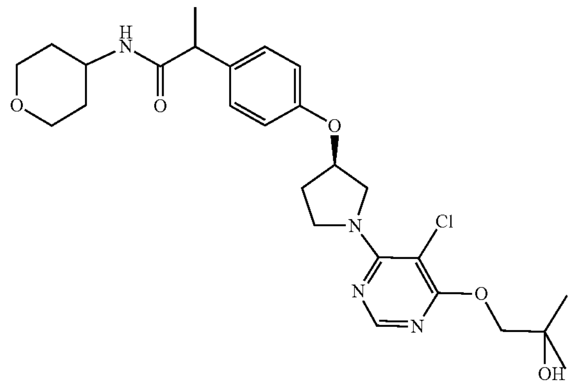 [SMILES: CC(C(=O)NC1CCOCC1)c1ccc(O[C@@H]2CCN(c3ncnc(OCC(C)(C)O)c3Cl)C2)cc1] | 519 [M + H]+ | 1.02 (H) |
| 1.92 | VI | | 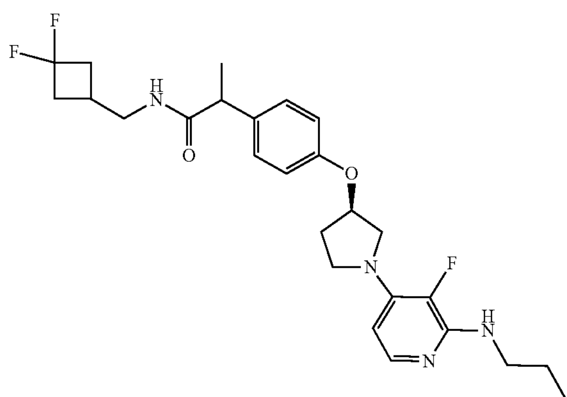 [SMILES: CCCNc1nccc(N2CC[C@@H](Oc3ccc(C(C)C(=O)NCC4CC(F)(F)C4)cc3)C2)c1F] | 491 [M + H]+ | 0.85 (H) |
| 1.93 | IX | | 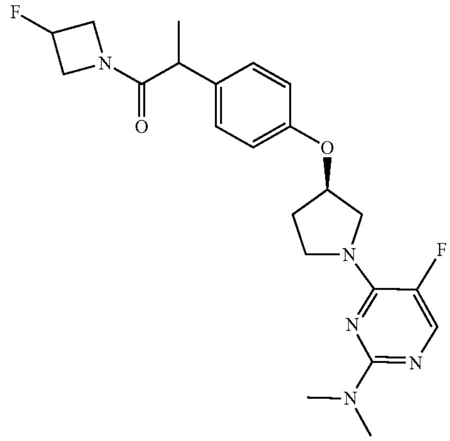 [SMILES: CC(C(=O)N1CC(F)C1)c1ccc(O[C@@H]2CCN(c3nc(N(C)C)ncc3F)C2)cc1] | 432 [M + H]+ | 0.73 (H) |

*ex 1.4,1.6,1.10, 1.13, 1.14: stereochemistry at the cyclopropane is a mixture of R,R and S,S (i.e. trans).
† for amines used as hydrochlorides 6 μL DIPEA are additionally added.
‡ amines with a boiling point below 70° C. are preferentially added to the activated acid solution in neat form.

Example 2

Example 2.1 (General Route)

(R)-2-(4-[1-(2-Diethylamino-pyrimidin-4-yl)-pyrrolidin-3-lyoxy]-phenyl)-N-ethyl-propionamide 50 mg (0.13 mmol) of example XII, 40 µl (0.38 mmol) of diethylamine and 30 µl (0.17 mmol) of DIPEA are dissolved in 2 ml ACN. The reaction mixture is stirred at 110° C. for 3 h in a sealed tube and then purified by HPLC-MS (MeOH/H₂O/TFA) yielding the title compound as TFA salt.

$C_{23}H_{33}N_5O_2$ (M=411.6 g/mol)
ESI-MS: 412 [M+H]⁺
$R_t$ (HPLC): 0.90 min (method F)

The following compounds are prepared analogously to example 2.1.

For the example 2.2 the reaction time is 2 h at 140° C. and 3.5 eq of N-ethylmethylamine are added.

For the examples 2.3, 2.4, 2.5 and 2.6 the reaction time is 3 h at 90° C.

For the examples 2.3, 2.4. and 2.5 are 2.2 eq of DIPEA added.

For the example 2.3 are added 4.1 eq of N-methyl-N-propylamine.

For the example 2.4 are added 2.6 eq of 3,3-difluoropyrrolidine hydrochloride.

For example 2.6 are added 2.5 eq of morpholine.

| Ex. | Starting material | Starting material (amine) | Structure | Mass spec result | HPLC retention time (method) |
|-----|-------------------|---------------------------|-----------|------------------|------------------------------|
| 2.1 | XII | | 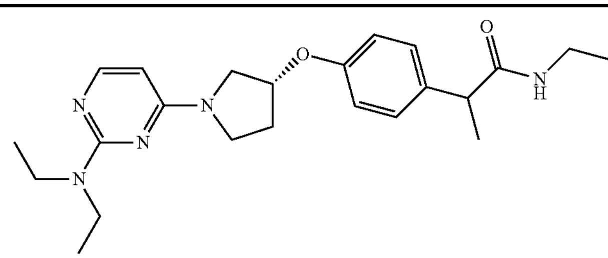 | 412 [M + H]⁺ | 0.90 (F) |
| 2.2 | XII | | 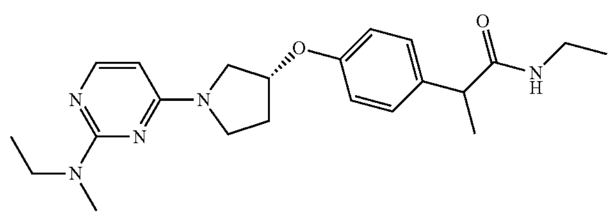 [SMILES: CCNC(=O)C(C)c1ccc(O[C@@H]2CCN(c3ccnc(N(C)CC)n3)C2)cc1] | 398 [M + H]⁺ | 1.00 (C) |
| 2.3 | XII | | 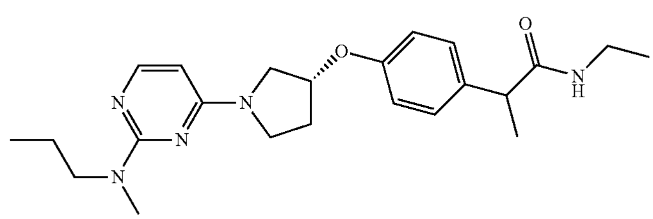 [SMILES: CCCN(C)c1nccc(N2CC[C@@H](Oc3ccc(C(C)C(=O)NCC)cc3)C2)n1] | 412 [M + H]⁺ | 1.05 (C) |
| 2.4 | XII | | 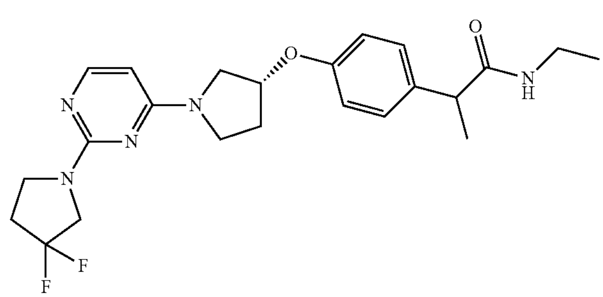 [SMILES: CCNC(=O)C(C)c1ccc(O[C@@H]2CCN(c3ccnc(N4CCC(F)(F)C4)n3)C2)cc1] | 446 [M + H]⁺ | 1.01 (C) |

| Ex. | Starting material | Starting material (amine) | Structure | Mass spec result | HPLC retention time (method) |
|---|---|---|---|---|---|
| 2.5 | XII | HN-cyclopropyl, methyl · ClH | (structure) | 410 [M + H]⁺ | 1.01 (C) |
| 2.6 | XII | morpholine (HN) | (structure) | 426 [M + H]⁺ | 0.93 (C) |

Examples 2.1, 2.2, 2.3, 2.4, 2.5 and 2.6 are isolated as TFA-salts

Example 3

Example 3.1 (General Route)

N-Cyclopropyl-2-(4-(1-[5-fluoro-6-(2-hydroxy-2-methyl-propoxy)-pyrimidin-4-yl]-(R)-pyrrolidin-3-yloxy)-phenyl)-propionamide To 42 mg (0.10 mmol) of example XIII in 3 mL DMF are added 42 µl (0.30 mmol) of TEA and 32 mg (100 µmol) TBTU and it is stirred at r.t. for 10 min. Then 14 µl (0.20 mmol) of cyclopropylamine are added and the resulting mixture is stirred at r.t over night. The mixture is directly purified by prep. HPLC-MS (ACN/H₂O/NH₄OH).

$C_{24}H_{31}FN_4O_4$ (M=458.5 g/mol)

ESI-MS: 459 [M+H]⁺

$R_t$ (HPLC): 0.67 min (method J)

The following compounds are prepared analogously to example 3.1.

For the examples 3.5 and 3.6 are added 1.1 eq of the amine.

For the example 3.11 is added 4.0 eq of the amine.

For example 3.13 are added 1.2 eq of the amine. The mixture is directly purified by prep. HPLC-MS (ACN/H₂O/TFA).

| Ex. | Starting material | Starting material (amine) | Structure | Mass spec result | HPLC retention time (method) |
|---|---|---|---|---|---|
| 3.1 | XIII | cyclopropylamine | 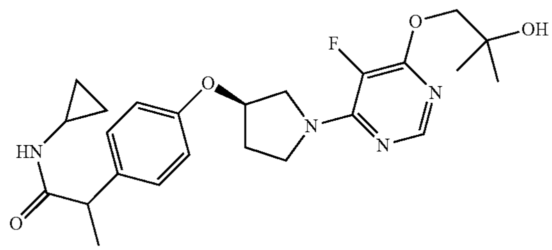 [SMILES: CC(C(=O)NC1CC1)c1ccc(O[C@@H]2CCN(c3ncnc(OCC(C)(C)O)c3F)C2)cc1] | 459 [M + H]+ | 0.67 (J) |
| 3.2* | XIII | 2-methylcyclopropylamine | 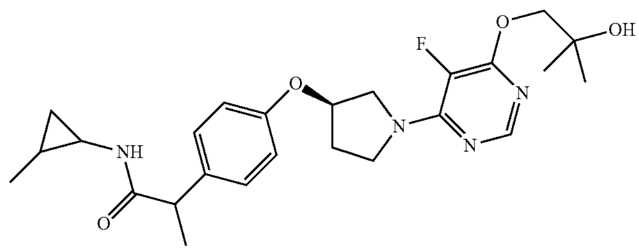 [SMILES: CC(C(=O)NC1CC1C)c1ccc(O[C@@H]2CCN(c3ncnc(OCC(C)(C)O)c3F)C2)cc1] | 473 [M + H]+ | 0.72 (J) |
| 3.3 | XIV | cyclopropylamine | 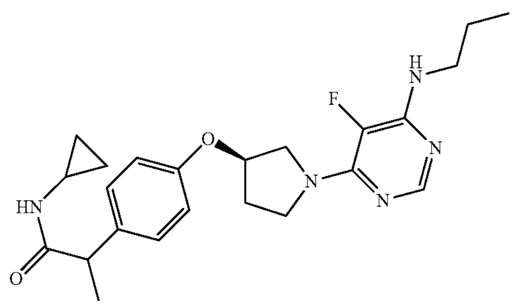 [SMILES: CCCNc1ncnc(N2CC[C@@H](Oc3ccc(C(C)C(=O)NC4CC4)cc3)C2)c1F] | 428 [M + H]+ | 0.72 (J) |
| 3.4 | IX | 3-fluoroaniline | 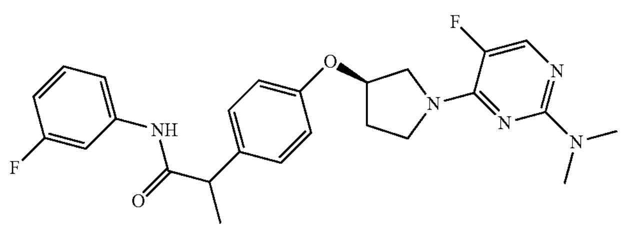 [SMILES: CC(C(=O)Nc1cccc(F)c1)c1ccc(O[C@@H]2CCN(c3nc(N(C)C)ncc3F)C2)cc1] | 468 [M + H]+ | 0.92 (J) |
| 3.5 | VIII | 3-aminopyridine | 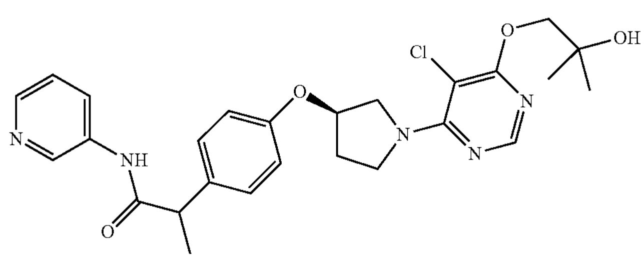 [SMILES: CC(C(=O)Nc1cccnc1)c1ccc(O[C@@H]2CCN(c3ncnc(OCC(C)(C)O)c3Cl)C2)cc1] | 512 [M + H]+ | 0.72 (J) |
| 3.6 | IX | 3-aminopyridine | 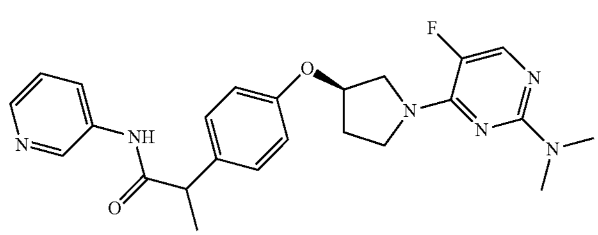 [SMILES: CC(C(=O)Nc1cccnc1)c1ccc(O[C@@H]2CCN(c3nc(N(C)C)ncc3F)C2)cc1] | 451 [M + H]+ | 0.78 (J) |

-continued

| Ex. | Starting material | Starting material (amine) | Structure | Mass spec result | HPLC retention time (method) |
|---|---|---|---|---|---|
| 3.7 | XIII | F-CH(F)-CH2-NH2 | 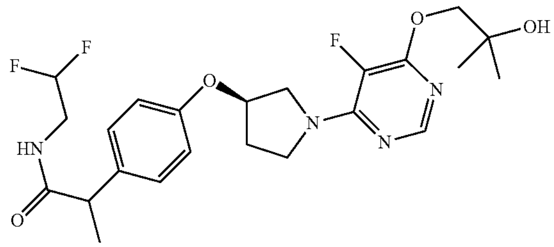 [SMILES: CC(C(=O)NCC(F)F)c1ccc(O[C@@H]2CCN(c3ncnc(OCC(C)(C)O)c3F)C2)cc1] | 483 [M + H]+ | 0.69 (J) |
| 3.8 | XIII | CH3CH2-NH2 | 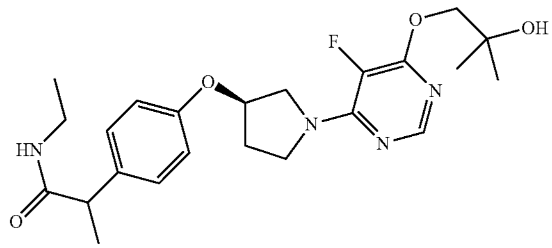 [SMILES: CCNC(=O)C(C)c1ccc(O[C@@H]2CCN(c3ncnc(OCC(C)(C)O)c3F)C2)cc1] | 447 [M + H]+ | 0.66 (J) |
| 3.9 * | XIV | H2N-cyclopropyl-CH3 | 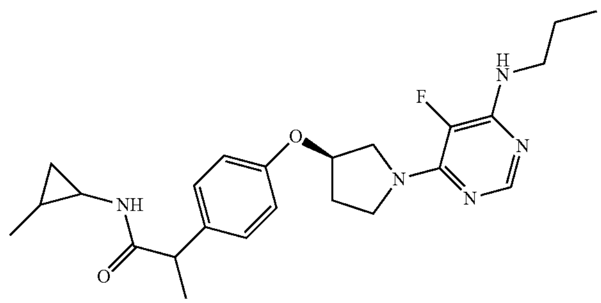 [SMILES: CCCNc1ncnc(N2CC[C@@H](Oc3ccc(C(C)C(=O)NC4CC4C)cc3)C2)c1F] | 442 [M + H]+ | 0.77 (J) |
| 3.10 | XIV | F-CH(F)-CH2-NH2 | 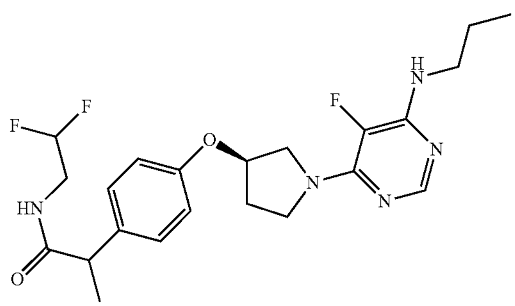 [SMILES: CCCNc1ncnc(N2CC[C@@H](Oc3ccc(C(C)C(=O)NCC(F)F)cc3)C2)c1F] | 452 [M + H]+ | 0.74 (J) |
| 3.11 | VIII | NH3 | 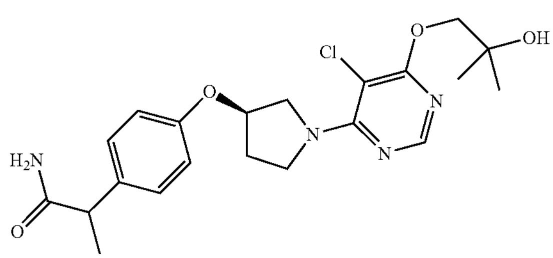 [SMILES: CC(C(N)=O)c1ccc(O[C@@H]2CCN(c3ncnc(OCC(C)(C)O)c3Cl)C2)cc1] | 435 [M + H]+ | 0.64 (J) |

| Ex. | Starting material | Starting material (amine) | Structure | Mass spec result | HPLC retention time (method) |
|---|---|---|---|---|---|
| 3.12 | XIV | ethylamine | (structure) | 416 [M + H]⁺ | 0.72 (J) |
| 3.13 | VIII | H₂N-CH(CN)·ClH | (structure) | 488 [M + H]⁺ | 0.86 (E) |

* ex 3.2, 3.9: stereochemistry at the cyclopropane is a mixture of R,R and S,S (i.e. trans)

Example 4

Example 4.1 (General Route)

2-(4-[1-(4-Ethoxyl-phenyl)-(R)-pyrrolidin-3-yloxy]-phenyl)-N-ethyl-propionamide

Under inert atmosphere the mixture of 55 mg (0.21 mmol) of example III, 42 mg (0.21 mmol) of 4-bromophenetole, 81 mg (0.84 mmol) of sodium tert. butoxide, 25 mg (84 µmol) of 2-(di-t-butylphosphino)biphenyl and 19 mg (21 µmol) of tris (dibenzylideneacetine)dipalladium(0) in 1.5 ml dioxane is stirred at 45° C. over night. The crude mixture is directly purified by prep. HPLC-MS (MeOH/H₂O/NH₄OH)

$C_{23}H_{30}N_2O_3$ (M=382.5 g/mol)

ESI-MS: 383 [M+H]⁺

R$_t$ (HPLC): 1.15 min (method A)

The following compounds are prepared analogously to example 4.1.

| Ex. | Starting material | Starting material | Structure | Mass spec result | HPLC retention time (method) |
|---|---|---|---|---|---|
| 4.1 | III | (4-bromophenetole) | (structure) | 383 [M + H]⁺ | 1.15 (A) |

| Ex. | Starting material | Starting material | Structure | Mass spec result | HPLC retention time (method) |
|---|---|---|---|---|---|
| 4.2 | III | | 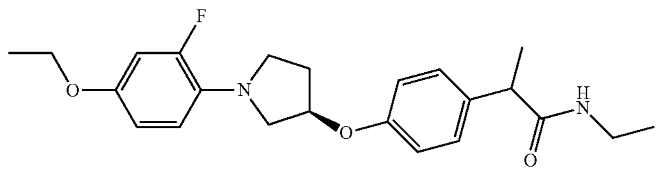 [SMILES: CCNC(=O)C(C)c1ccc(O[C@@H]2CCN(c3ccc(OCC)cc3F)C2)cc1] | 401 [M + H]⁺ | 1.18 (A) |

Example 5

2-(4-[1-(2-Cyclopropyl-pyrimidin-4-yl)-(R)-pyrrolidin-3-yloxy]-phenyl)-N-ethyl-propionamide Under inert atmosphere 50 mg (0.13 mmol) of XII are dissolved in 3 ml dioxane. 30 mg (0.35 mmol) of cyclopropylboronic acid, 55 mg (0.26 mmol) of $K_3PO_4$ and 5 mg (0.01 mmol) of 1,1'-bis(diphenylphosphino)ferrocene dichloropalladium(II) are added. The reaction mixture is stirred at 90° C. over night. The same amounts of the boronic acid, the base and of the catalyst are added. The reaction mixture is stirred at 120° C. in a microwave oven for 5 h and at 100° C. over night. The reaction mixture is diluted with MeOH and water, filtered and purified by prep. HPLC-MS (MeOH/$H_2O$/$NH_4OH$).

$C_{22}H_{28}N_4O_2$ (M=380.5 g/mol)

ESI-MS: 381 [M+H]⁺

$R_t$ (HPLC): 1.14 min (method A)

Example 6

Example 6.1 Isomer 1 and Example 6.1 Isomer 2

(R and S)-2-(4-(1-[5-Chloro-6-(2-hydroxy-2-methyl-propoxy)-pyrimidin-4-yl]-(R)-pyrrolidin-3-yloxy)-phenyl)-N-cyclopropyl-propionamide The stereoisomers of example 1.1 are separated by prep. chiral HPLC.

$R_t$ (chiral HPLC): 5.16 min (method K) isomer 1
$R_t$ (chiral HPLC): 5.69 min (method K) isomer 2

After prep. chiral HPLC, isomers 1 and 2 are single stereoisomers. However, the absolute stereochemistry at the alpha position to the amide has not been determined. Therefore, the chirality is only indicated by a star (*) in conjunction with the text "isomer 1" or "isomer 2" added to the example number. The stereocentre at the pyrrolidine ring is as shown.

The following compounds are prepared in analogy to example 6.1 isomer 1 and example 6.1 isomer 2.

| Ex. | Starting material | Structure | Mass spec result | HPLC retention time (method) |
|---|---|---|---|---|
| 6.1 isomer 1 | Example 1.1 | 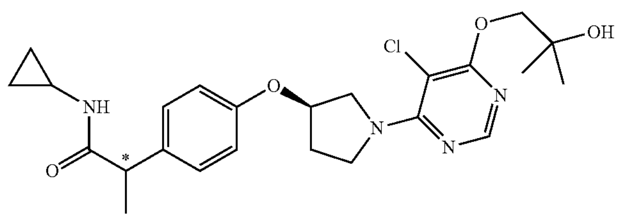 [SMILES: CC(C(=O)NC1CC1)c1ccc(O[C@@H]2CCN(c3ncnc(OCC(C)(C)O)c3Cl)C2)cc1] | 475 [M + H]+ | 5.16 (K) earlier eluting isomer |
| 6.1 isomer 2 | Example 1.1 | 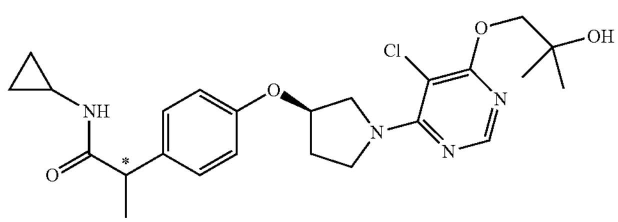 [SMILES: CC(C(=O)NC1CC1)c1ccc(O[C@@H]2CCN(c3ncnc(OCC(C)(C)O)c3Cl)C2)cc1] | 475 [M + H]+ | 5.69 (K) later eluting isomer |
| 6.2 isomer 1 * | Example 1.6 | 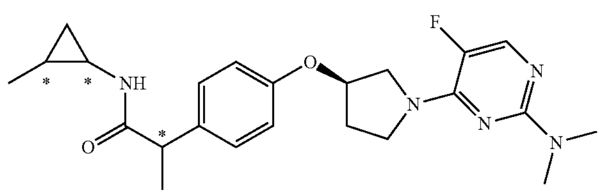 | 428 [M + H]+ | 3.30 (K) second eluting isomer |
| 6.2 isomer 2 * | Example 1.6 | 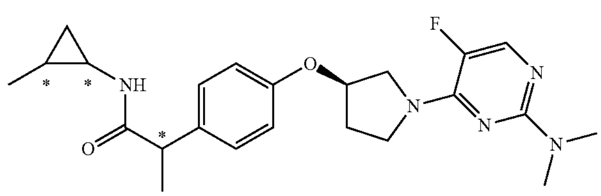 | 428 [M + H]+ | 3.13 (K) first eluting isomer |
| 6.2 isomer 3 * | Example 1.6 | 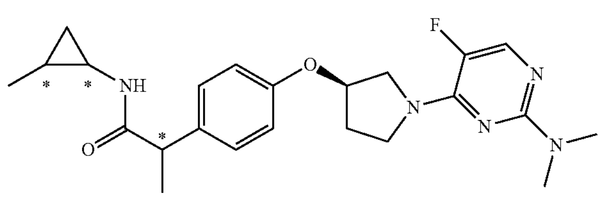 | 428 [M + H]+ | 3.37 (L) later eluting isomer |
| 6.2 isomer 4 * | Example 1.6 | 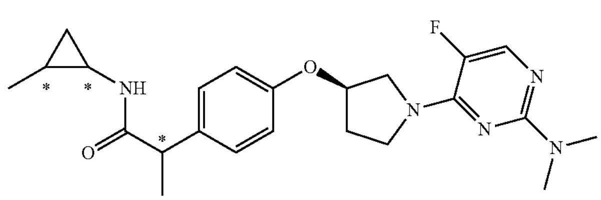 | 428 [M + H]+ | 2.98 (L) earlier eluting isomer |
| 6.3 isomer 1 | Example 1.17 | 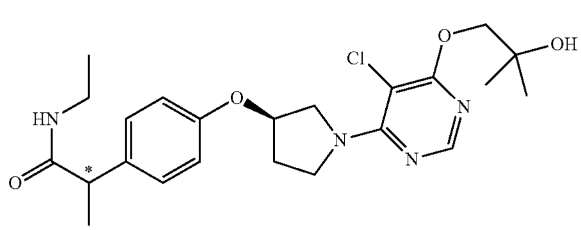 [SMILES: CCNC(=O)C(C)c1ccc(O[C@@H]2CCN(c3ncnc(OCC(C)(C)O)c3Cl)C2)cc1] | 463 [M + H]+ | 3.93 (K) earlier eluting isomer |

-continued

| Ex. | Starting material | Structure | Mass spec result | HPLC retention time (method) |
|---|---|---|---|---|
| 6.3 isomer 2 | Example 1.17 | 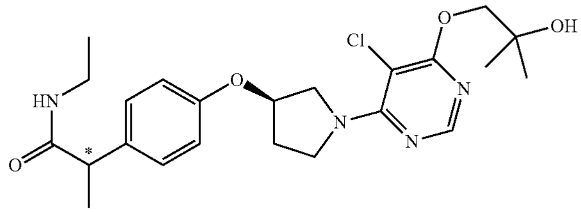 [SMILES: CCNC(=O)C(C)c1ccc(O[C@@H]2CCN(c3ncnc(OCC(C)(C)O)c3Cl)C2)cc1] | 463 [M + H]+ | 4.46 (K) later eluting isomer |
| 6.4 isomer 1 | Example 1.26 | 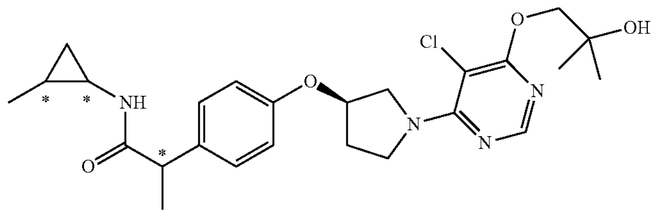 [SMILES: CC(C(=O)NC1CC1C)c1ccc(O[C@@H]2CCN(c3ncnc(OCC(C)(C)O)c3Cl)C2)cc1] | 489 [M + H]+ | 3.58 (L) fourth eluting isomer |
| 6.4 isomer 2 | Example 1.26 | 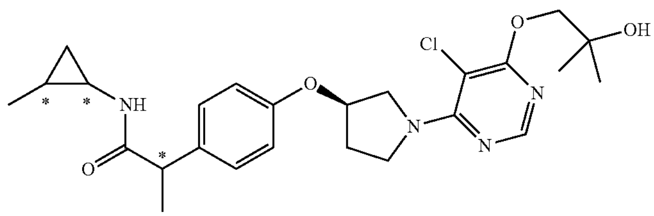 [SMILES: CC(C(=O)NC1CC1C)c1ccc(O[C@@H]2CCN(c3ncnc(OCC(C)(C)O)c3Cl)C2)cc1] | 489 [M + H]+ | 3.38 (L) third eluting isomer |
| 6.4 isomer 3 | Example 1.26 | 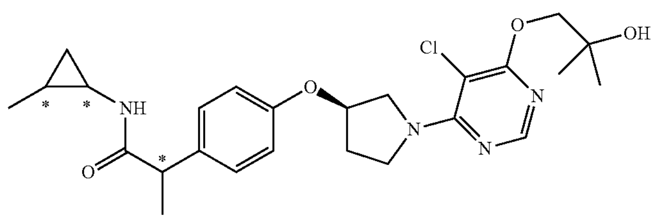 [SMILES: CC(C(=O)NC1CC1C)c1ccc(O[C@@H]2CCN(c3ncnc(OCC(C)(C)O)c3Cl)C2)cc1] | 489 [M + H]+ | 3.34 (L) second eluting isomer |
| 6.5 isomer 1 | Example 1.36 | 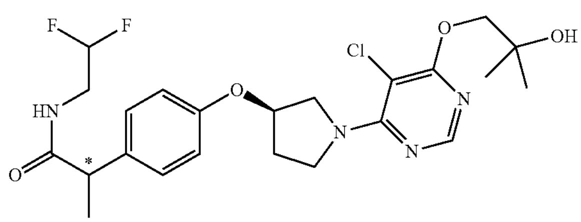 [SMILES: CC(C(=O)NCC(F)F)c1ccc(O[C@@H]2CCN(c3ncnc(OCC(C)(C)O)c3Cl)C2)cc1] | 499 [M + H]+ | 4.05 (L) later eluting isomer |
| 6.5 isomer 2 | Example 1.36 | 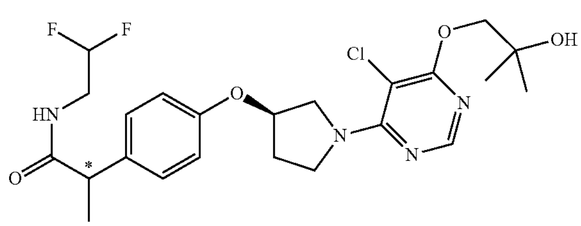 [SMILES: CC(C(=O)NCC(F)F)c1ccc(O[C@@H]2CCN(c3ncnc(OCC(C)(C)O)c3Cl)C2)cc1] | 499 [M + H]+ | 3.55 (L) earlier eluting isomer |

-continued

| Ex. | Starting material | Structure | Mass spec result | HPLC retention time (method) |
|---|---|---|---|---|
| 6.6 isomer 1 | Example 1.27 | 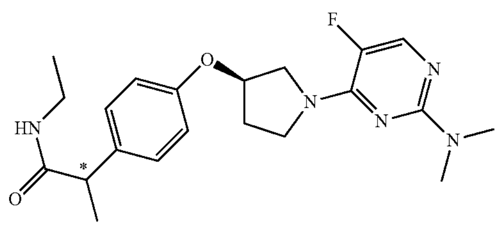 [SMILES: CCNC(=O)C(C)c1ccc(O[C@@H]2CCN(c3nc(N(C)C)ncc3F)C2)cc1] | 402 [M + H]⁺ | 3.17 (L) earlier eluting isomer |
| 6.7 isomer 1 | Example 3.13 | 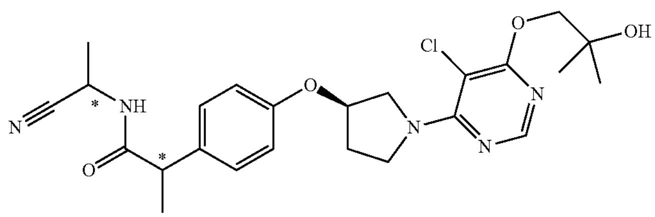 [SMILES: CC(C#N)NC(=O)C(C)c1ccc(O[C@@H]2CCN(c3ncnc(OCC(C)(C)O)c3Cl)C2)cc1] | 488 [M + H]⁺ | 3.88 (L) fourth eluting isomer |
| 6.8 isomer 1 | Example 7.34 | 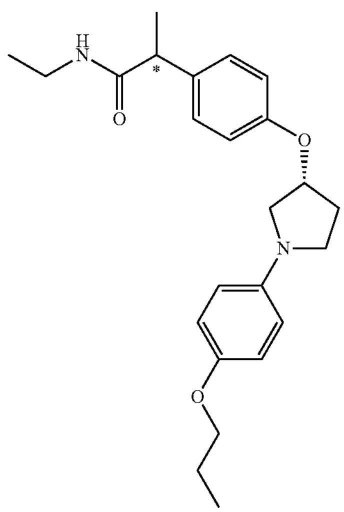 [SMILES: CCCOc1ccc(N2CC[C@@H](Oc3ccc(C(C)C(=O)NCC)cc3)C2)cc1] | 397 [M + H]⁺ | 3.59 (M) earlier eluting isomer |
| 6.9 isomer 2 | Example 7.34 | 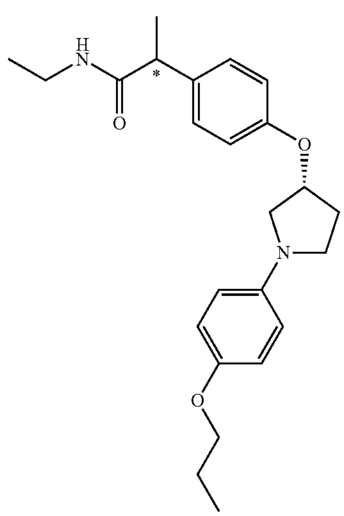 [SMILES: CCCOc1ccc(N2CC[C@@H](Oc3ccc(C(C)C(=O)NCC)cc3)C2)cc1] | 397 [M + H]⁺ | 4.19 (M) later eluting isomer |

* For examples 6.2, two subsequent chiral HPLC methods are needed for separation.

Method K leads to 6.2 isomer 1 and 6.2 isomer 2. Isomers 3 and 4 are isolated as mixture ($R_t$=3.63 min.; method K; last eluting fraction). The latter mixture was subjected to a second chiral HPLC (Method L) leading to 6.2 isomer 3 and 6.2 isomer 4.

Example 7

Example 7.1(General Route)

2-(4-[1-(4-Cyclobutoxy-phenyl)-(R)-pyrrolidin-3-yloxy]-phenyl)-N-ethyl-propionamide To 30 mg (0.10 mmol) of example III, 27 mg (0.12 mmol) of 1-bromo-4-cyclobutoxy-benzene and 40 mg (0.40 mmol) of sodium tert. butoxide in 2 mL Dioxan are added under inert atmosphere 10 mg (0.01 mmol) of chloro(2-dicyclohexylphosphino-2',4',6'-tri-propyl-1,1'-biphenyl)[2-(2-aminoethyl)phenyl]palladium(II) dissolved in dioxane. The reaction mixture is stirred at 70° C. over night in a sealed tube. The solvent is removed in vacuo. The residue is dissolved in DMF, filtered and purified by prep. HPLC-MS (ACN/H$_2$O/NH$_4$OH).

$C_{25}H_{32}N_2O_3$ (M=408.6 g/mol)
ESI-MS: 409 [M+H]$^+$
$R_t$ (HPLC): 0.68 min (method I)

The following compounds are prepared analogously to example 7.1.

The example 7.8 is extracted with water and EtOAc, dried over MgSO$_4$, filtered and the solvent is removed in vacuo. The residue is purified by prep. HPLC-MS (ACN/H$_2$O/TFA).

The examples 7.9, 7.22 and 7.33 are stirred at r.t. over night, then they are extracted with water and EtOAc, dried over MgSO$_4$, filtered and the solvent is removed in vacuo. The residue is first purified by flash chromatography (silica gel, PE/EtOAc=1/1-EtOAc), then by prep. HPLC-MS (ACN/H$_2$O/TFA).

| Ex. | Starting material | Starting material | Structure | Mass spec result | HPLC retention time (method) |
|---|---|---|---|---|---|
| 7.1 | III | XV | 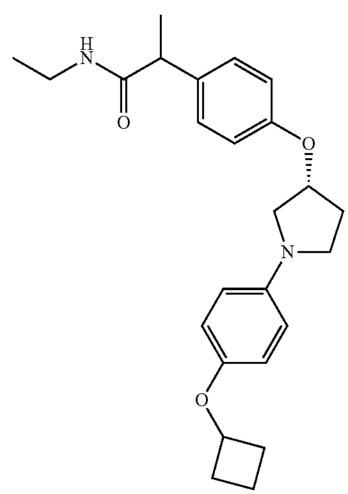 [SMILES: CCNC(=O)C(C)c1ccc(O[C@@H]2CCN(c3ccc(OC4CCC4)cc3)C2)cc1] | 409 [M + H]$^+$ | 0.68 (I) |

-continued

| Ex. | Starting material | Starting material | Structure | Mass spec result | HPLC retention time (method) |
|---|---|---|---|---|---|
| 7.2 | III | (4-bromophenyl cyclopentyl ether) | 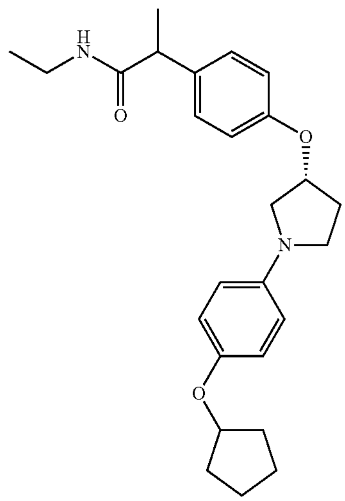 [SMILES: CCNC(=O)C(C)c1ccc(O[C@@H]2CCN(c3ccc(OC4CCCC4)cc3)C2)cc1] | 423 [M + H]⁺ | 0.71 (I) |
| 7.3 | III | XVI | 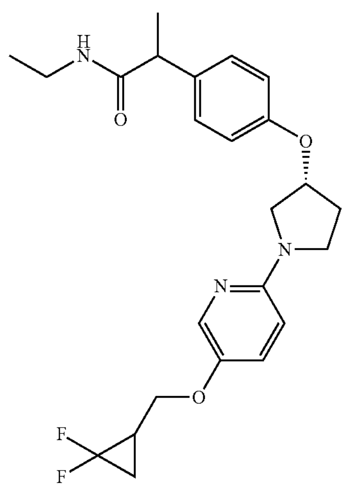 [SMILES: CCNC(=O)C(C)c1ccc(O[C@@H]2CCN(c3ccc(OCC4CC4(F)F)cn3)C2)cc1] | 446 [M + H]⁺ | 0.58 (I) |
| 7.4 | III | (1-iodo-3-(trifluoromethyl)benzene) | 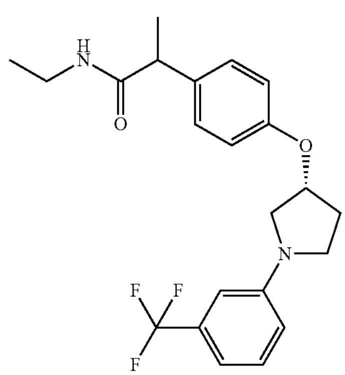 | 407 [M + H]⁺ | 0.68 (I) |

-continued

| Ex. | Starting material | Starting material | Structure | Mass spec result | HPLC retention time (method) |
|---|---|---|---|---|---|
| 7.5 | III | Cl, I (2-chloro-1-iodo-4-propoxybenzene) | 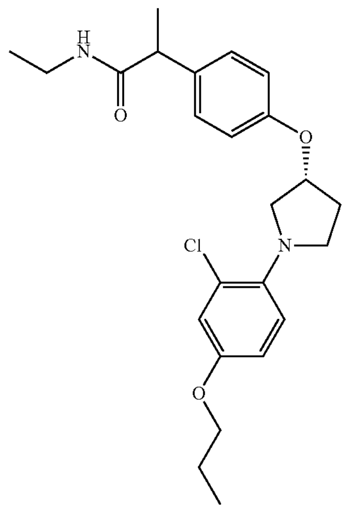 [SMILES: CCCOc1ccc(N2CC[C@@H](Oc3ccc(C(C)C(=O)NCC)cc3)C2)c(Cl)c1] | 431 [M + H]⁺ | 0.71 (I) |
| 7.6 | III | (4-fluoro-1-iodo-2-trifluoromethylbenzene) | 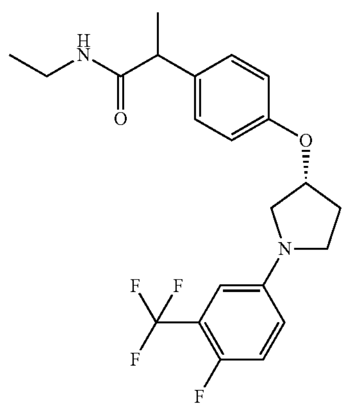 [SMILES: CCNC(=O)C(C)c1ccc(O[C@@H]2CCN(c3ccc(F)c(C(F)(F)F)c3)C2)cc1] | 425 [M + H]⁺ | 0.67 (I) |
| 7.7 | III | (4-iodo-2-butoxypyridine) | 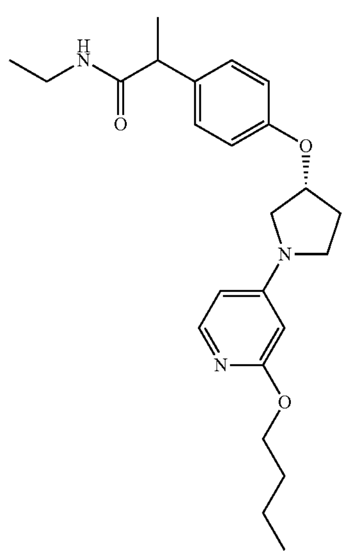 [SMILES: CCCCOc1cc(N2CC[C@@H](Oc3ccc(C(C)C(=O)NCC)cc3)C2)ccn1] | 412 [M + H]⁺ | 0.62 (I) |

-continued

| Ex. | Starting material | Starting material | Structure | Mass spec result | HPLC retention time (method) |
|---|---|---|---|---|---|
| 7.8 | III | (4-iodophenyl cyclopropylmethyl ether) | 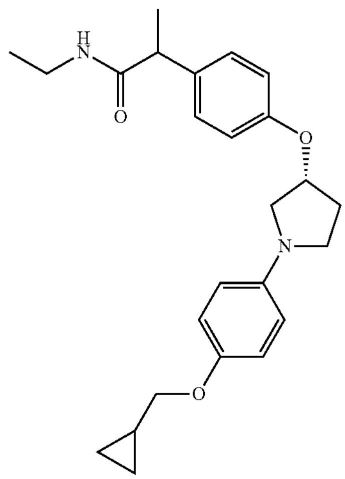 [SMILES: CCNC(=O)C(C)c1ccc(O[C@@H]2CCN(c3ccc(OCC4CC4)cc3)C2)cc1] | 409 [M + H]+ | 1.27 (C) |
| 7.9 | III | 2-bromo-6-(trifluoromethyl)pyridine | 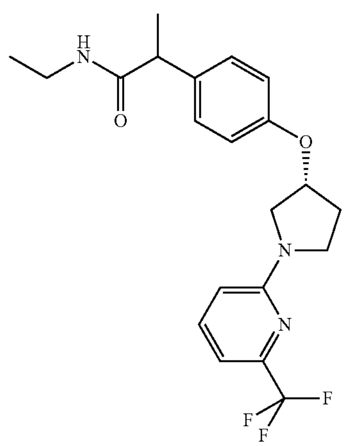 [SMILES: CCNC(=O)C(C)c1ccc(O[C@@H]2CCN(c3cccc(C(F)(F)F)n3)C2)cc1] | 408 [M + H]+ | 1.32 (C) |
| 7.10 | III | 7-bromo-3,4-dihydro-2H-1,5-benzodioxepine | 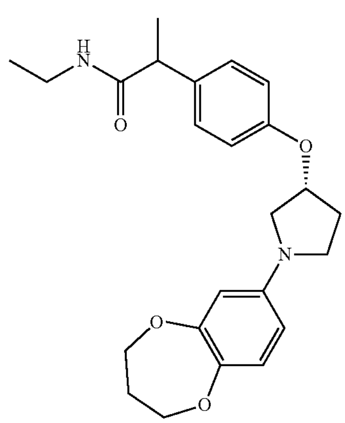 [SMILES: CCNC(=O)C(C)c1ccc(O[C@@H]2CCN(c3ccc4c(c3)OCCCO4)C2)cc1] | 411 [M + H]+ | 0.59 (I) |

-continued

| Ex. | Starting material | Starting material | Structure | Mass spec result | HPLC retention time (method) |
|---|---|---|---|---|---|
| 7.11 | III | | 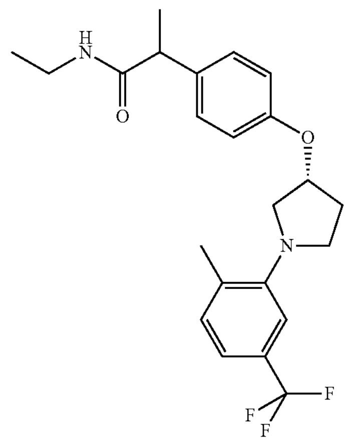 [SMILES: CCNC(=O)C(C)c1ccc(O[C@@H]2CCN(c3cc(C(F)(F)F)ccc3C)C2)cc1] | 421 [M + H]+ | 0.70 (I) |
| 7.12 | III | | 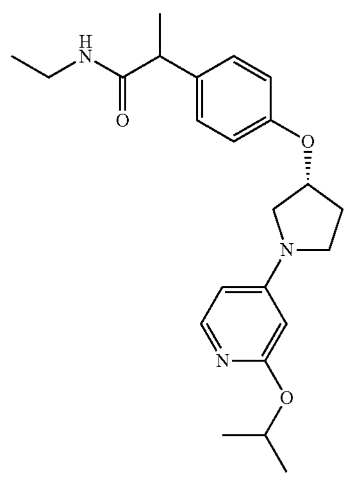 [SMILES: CCNC(=O)C(C)c1ccc(O[C@@H]2CCN(c3ccnc(OC(C)C)c3)C2)cc1] | 398 [M + H]+ | 0.58 (I) |
| 7.13 | III | | 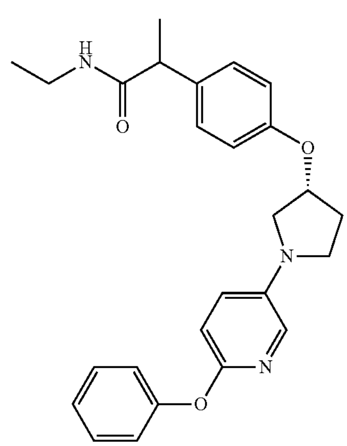 [SMILES: CCNC(=O)C(C)c1ccc(O[C@@H]2CCN(c3ccc(Oc4ccccc4)nc3)C2)cc1] | 432 [M + H]+ | 0.62 (I) |

-continued

| Ex. | Starting material | Starting material | Structure | Mass spec result | HPLC retention time (method) |
|---|---|---|---|---|---|
| 7.14 | III | | 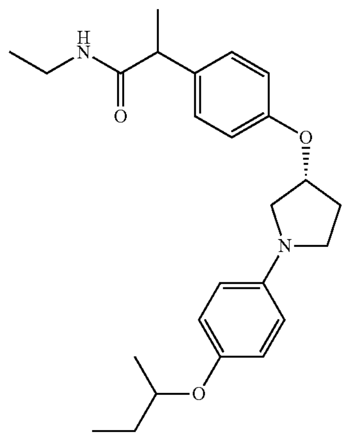 [SMILES: CCNC(=O)C(C)c1ccc(O[C@@H]2CCN(c3ccc(OC(C)CC)cc3)C2)cc1] | 411 [M + H]+ | 0.69 (I) |
| 7.15 | III | | 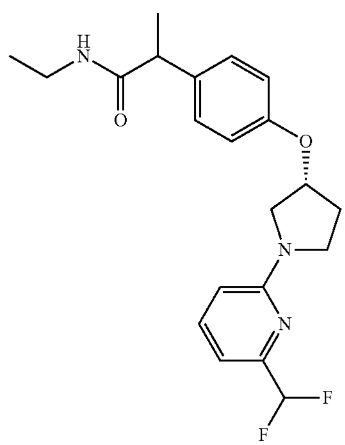 [SMILES: CCNC(=O)C(C)c1ccc(O[C@@H]2CCN(c3cccc(C(F)F)n3)C2)cc1] | 390 [M + H]+ | 0.60 (I) |
| 7.16 | III | | 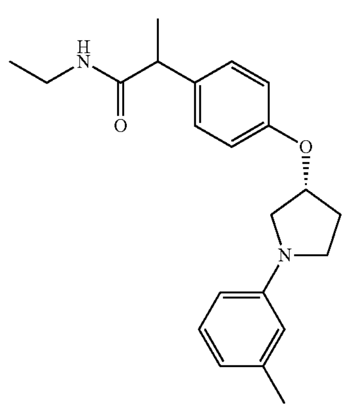 [SMILES: CCNC(=O)C(C)c1ccc(O[C@@H]2CCN(c3cccc(C)c3)C2)cc1] | 353 [M + H]+ | 0.99 (E) |

| Ex. | Starting material | Starting material | Structure | Mass spec result | HPLC retention time (method) |
|---|---|---|---|---|---|
| 7.17 | III | I | 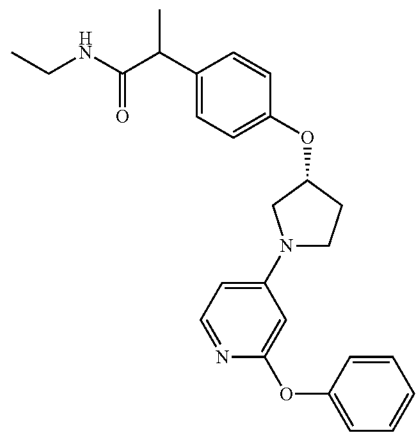 [SMILES: CCNC(=O)C(C)c1ccc(O[C@@H]2CCN(c3ccnc(Oc4ccccc4)c3)C2)cc1] | 432 [M + H]$^+$ | 0.58 (I) |
| 7.18 | III | XVII | 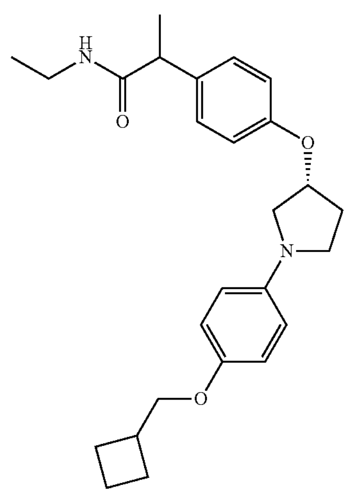 [SMILES: CCNC(=O)C(C)c1ccc(O[C@@H]2CCN(c3ccc(OCC4CCC4)cc3)C2)cc1] | 423 [M + H]$^+$ | 0.72 (I) |
| 7.19 | III | | 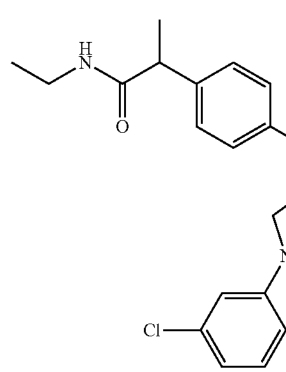 | 373 [M + H]$^+$ | 0.67 (I) |

-continued

| Ex. | Starting material | Starting material | Structure | Mass spec result | HPLC retention time (method) |
|---|---|---|---|---|---|
| 7.20 | III | (6-bromo-N,N-dimethylpyridin-2-amine) | 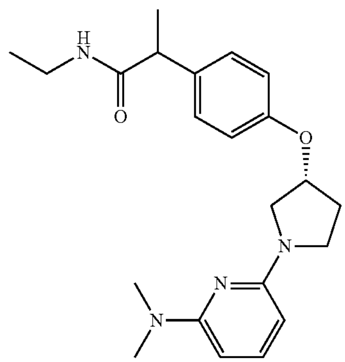 [SMILES: CCNC(=O)C(C)c1ccc(O[C@@H]2CCN(c3cccc(N(C)C)n3)C2)cc1] | 383 [M + H]⁺ | 0.65 (I) |
| 7.21 | III | (1-(2-cyclopropylethoxy)-4-bromobenzene) | 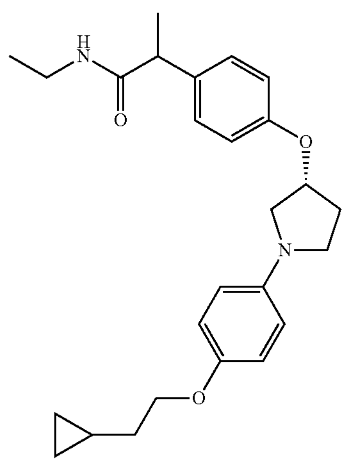 [SMILES: CCNC(=O)C(C)c1ccc(O[C@@H]2CCN(c3ccc(OCCC4CC4)cc3)C2)cc1] | 423 [M + H]⁺ | 0.70 (I) |
| 7.22 | III | (1-iodo-4-isopropoxybenzene) | 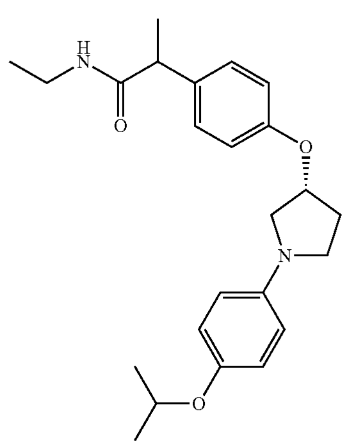 [SMILES: CCNC(=O)C(C)c1ccc(O[C@@H]2CCN(c3ccc(OC(C)C)cc3)C2)cc1] | 397 [M + H]⁺ | 1.25 (C) |

| Ex. | Starting material | Starting material | Structure | Mass spec result | HPLC retention time (method) |
|---|---|---|---|---|---|
| 7.23 | III | | 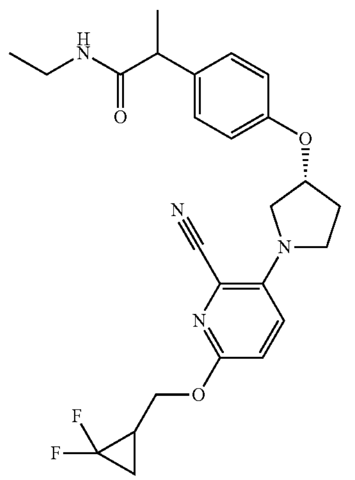 [SMILES: CCNC(=O)C(C)c1ccc(O[C@@H]2CCN(c3ccc(OCC4CC4(F)F)nc3C#N)C2)cc1] | 471 [M + H]+ | 0.62 (I) |
| 7.24 | III | | 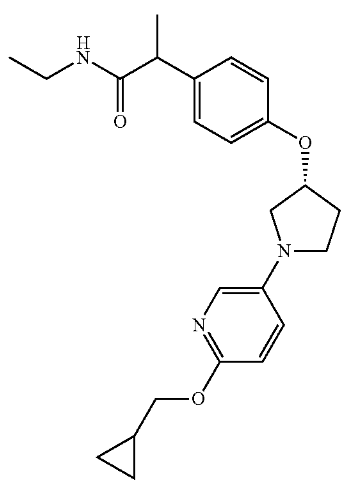 [SMILES: CCNC(=O)C(C)c1ccc(O[C@@H]2CCN(c3ccc(OCC4CC4)nc3)C2)cc1] | 410 [M + H]+ | 0.61 (I) |
| 7.25 | III | | 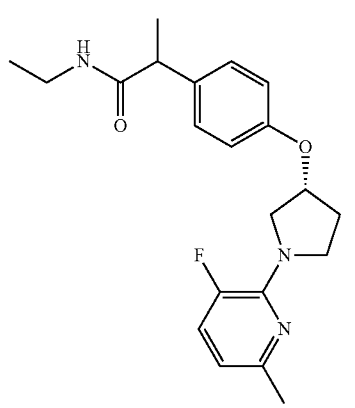 [SMILES: CCNC(=O)C(C)c1ccc(O[C@@H]2CCN(c3nc(C)ccc3F)C2)cc1] | 372 [M + H]+ | 0.63 (I) |

-continued

| Ex. | Starting material | Starting material | Structure | Mass spec result | HPLC retention time (method) |
|---|---|---|---|---|---|
| 7.26 | III | XIX | 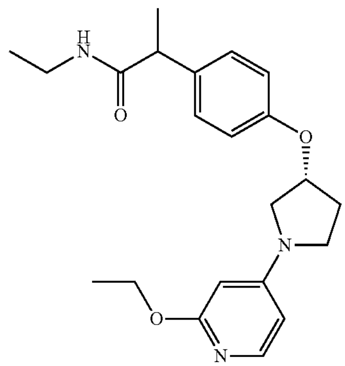 [SMILES: CCNC(=O)C(C)c1ccc(O[C@@H]2CCN(c3ccnc(OCC)c3)C2)cc1] | 384 [M + H]+ | 0.54 (I) |
| 7.27 | III | (6-bromo-3-fluoro-2-methylpyridine) | 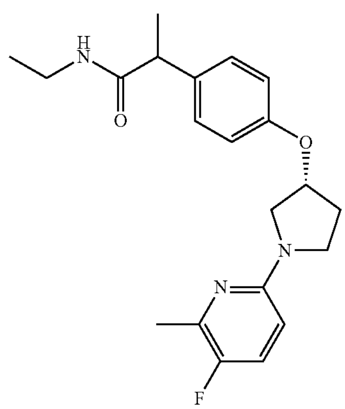 [SMILES: CCNC(=O)C(C)c1ccc(O[C@@H]2CCN(c3ccc(F)c(C)n3)C2)cc1] | 372 [M + H]+ | 0.60 (I) |
| 7.28 | III | (2-cyclohexyloxy-5-iodopyridine) | 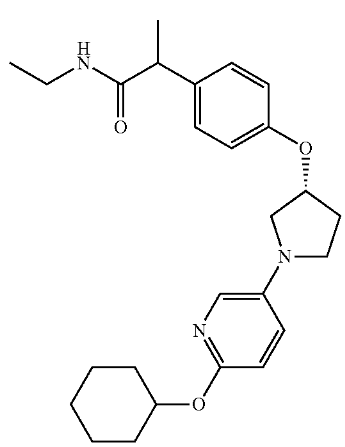 [SMILES: CCNC(=O)C(C)c1ccc(O[C@@H]2CCN(c3ccc(OC4CCCCC4)nc3)C2)cc1] | 438 [M + H]+ | 0.70 (I) |

| Ex. | Starting material | Starting material | Structure | Mass spec result | HPLC retention time (method) |
|---|---|---|---|---|---|
| 7.29 | III | | 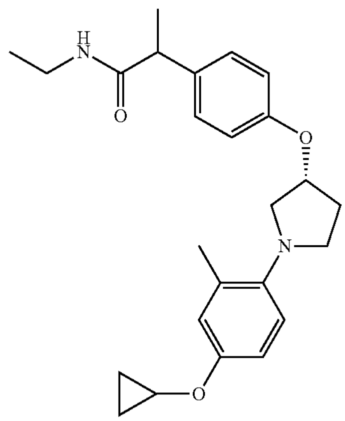 [SMILES: CCNC(=O)C(C)c1ccc(O[C@@H]2CCN(c3ccc(OC4CC4)cc3C)C2)cc1] | 409 [M + H]⁺ | 0.67 (I) |
| 7.30 | III | | 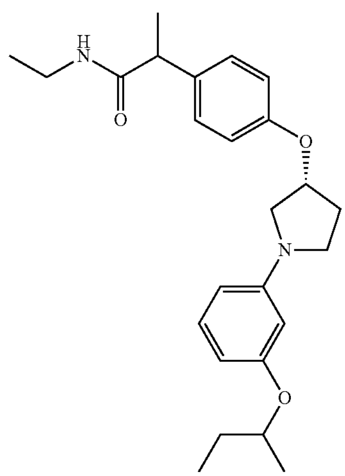 [SMILES: CCNC(=O)C(C)c1ccc(O[C@@H]2CCN(c3cccc(OC(C)CC)c3)C2)cc1] | 411 [M + H]⁺ | 0.71 (I) |
| 7.31 | III | | 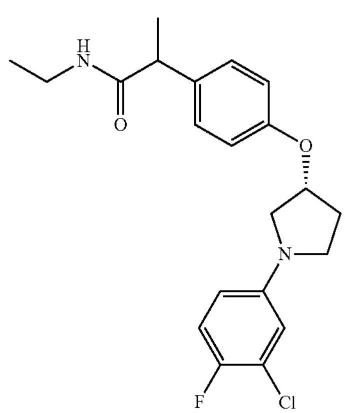 [SMILES: CCNC(=O)C(C)c1ccc(O[C@@H]2CCN(c3ccc(F)c(Cl)c3)C2)cc1] | 391 [M + H]⁺ | 0.66 (I) |

-continued

| Ex. | Starting material | Starting material | Structure | Mass spec result | HPLC retention time (method) |
|---|---|---|---|---|---|
| 7.32 | III | (4-bromo-2-benzyloxypyridine) | 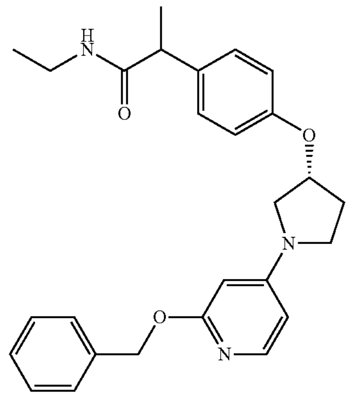 [SMILES: CCNC(=O)C(C)c1ccc(O[C@@H]2CCN(c3ccnc(OCc4ccccc4)c3)C2)cc1] | 446 [M + H]⁺ | 0.62 (I) |
| 7.33 | III | (2-bromo-6-methylpyridine) | 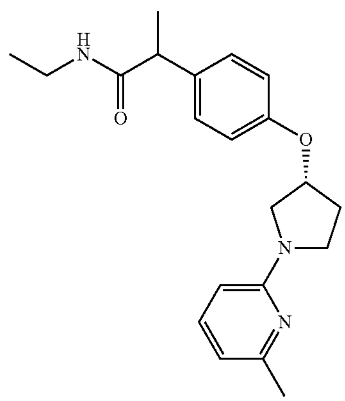 [SMILES: CCNC(=O)C(C)c1ccc(O[C@@H]2CCN(c3cccc(C)n3)C2)cc1] | 354 [M + H]⁺ | 0.85 (C) |
| 7.34 | III | (1-bromo-4-propoxybenzene) | 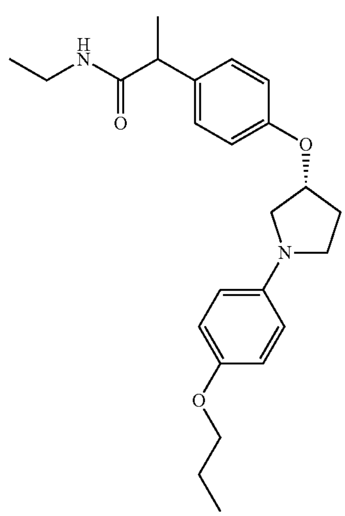 [SMILES: CCCOc1ccc(N2CC[C@@H](Oc3ccc(C(C)C(=O)NCC)cc3)C2)cc1] | 397 [M + H]⁺ | 0.67 (I) |

Example 8

Example 8.1 (General Route)

2-(4-[1-(5-Cyclopentyloxy-3-fluoro-pyridin-2-yl)-(R)-pyrrolidin-3-yloxy]-phenyl)-N-ethyl-propionamide 30 mg (0.10 mmol) of example III are dissolved in 0.25 ml DCM. 20 mg (0.12 mmol) of 2-chloro-5-cyclopentyloxy-3-fluoro-pyridine are dissolved in 0.25 ml DCM and added to the mixture with example III. The reaction mixture is stirred at 70° C. until the DCM is evaporated. The tube is sealed an heated at 180° C. for 3 h. 200 μl of NMP are added and it is stirred at 180° C. for 24 h. The reaction mixture is purified by prep. HPLC-MS (ACN/H$_2$O/NH$_4$OH).

$C_{25}H_{32}FN_3O_3$ (M=441.6 g/mol)

ESI-MS: 442 [M+H]$^+$

R$_t$ (HPLC): 0.70 min (method I)

The following compounds are prepared analogously to example 8.1.

| Ex. | Starting material | Starting material | Structure | Mass spec result | HPLC retention time (method) |
|-----|-------------------|-------------------|-----------|------------------|------------------------------|
| 8.1 | III | 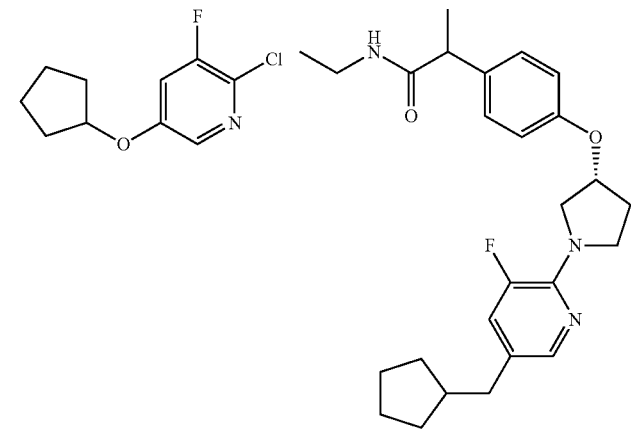 | 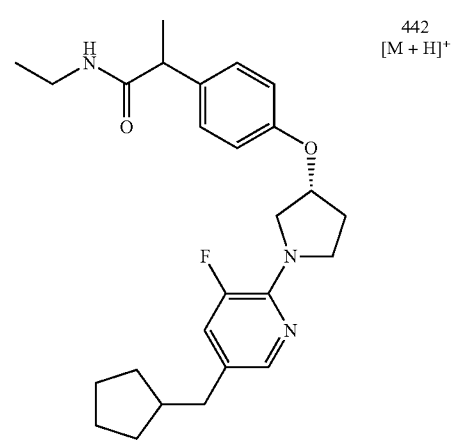 | 442 [M + H]$^+$ | 0.70 (I) |

-continued

| Ex. | Starting material | Starting material | Structure | Mass spec result | HPLC retention time (method) |
|---|---|---|---|---|---|
| 8.2 | III | | 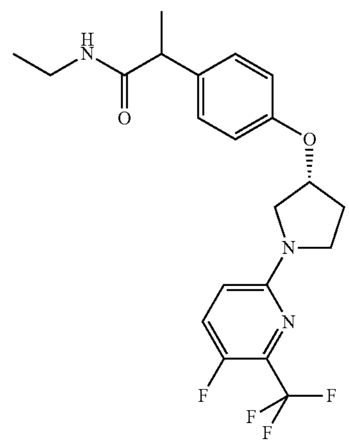 [SMILES: CCNC(=O)C(C)c1ccc(O[C@@H]2CCN(c3ccc(F)c(C(F)(F)F)n3)C2)cc1] | 426 [M + H]+ | 0.65 (I) |
| 8.3 | III | | 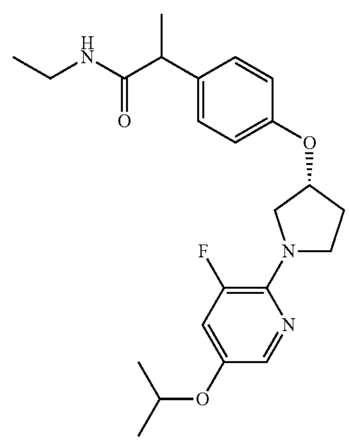 [SMILES: CCNC(=O)C(C)c1ccc(O[C@@H]2CCN(c3ncc(OC(C)C)cc3F)C2)cc1] | 416 [M + H]+ | 0.64 (I) |
| 8.4 | III | | 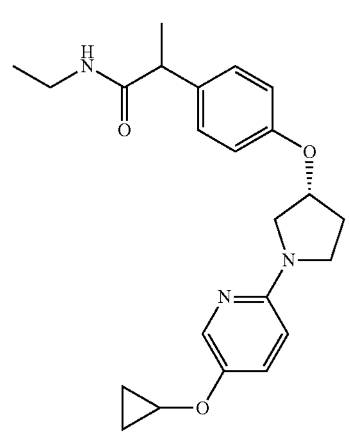 | 396 [M + H]+ | 0.57 (I) |

Example 9

Example 9.1 (General Route)

2-(4-(1-[5-(2,2-Difluoro-cyclopropylmethoxy)-pyrimidin-2-yl]-(R)-pyrrolidin-3-yloxy)-phenyl)-N-ethyl-propionamide 44 mg (0.20 mmol) of example XVIII are dissolved in 1 ml NMP. 30 mg (0.10 mmol) of example III are dissolved in 1 ml NMP and added to the mixture with example XVIII. 30 µl of DIPEA are added and the reaction mixture is stirred for 3 h at 140° C. in a sealed tube. The reaction mixture is purified by prep. HPLC-MS (ACN/H$_2$O/NH$_4$OH).

C$_{23}$H$_{28}$F$_2$N$_4$O$_3$ (M=446.5 g/mol)

ESI-MS: 447 [M+H]$^+$

R$_t$ (HPLC): 0.56 min (method I)

The following compounds are prepared analogously to example 9.1.

| Ex. | Starting material | Starting material | Structure | Mass spec result | HPLC retention time (method) |
|---|---|---|---|---|---|
| 9.1 | III | XVIII | 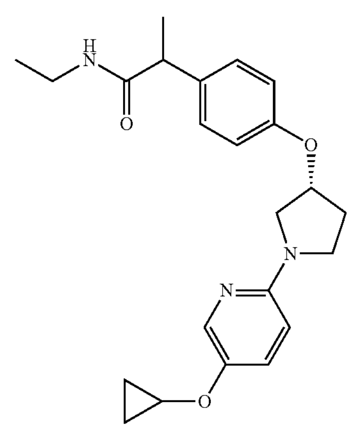 | 447 [M + H]$^+$ | 0.56 (I) |

-continued

| Ex. | Starting material | Starting material | Structure | Mass spec result | HPLC retention time (method) |
|---|---|---|---|---|---|
| 9.2 | III | Cl | 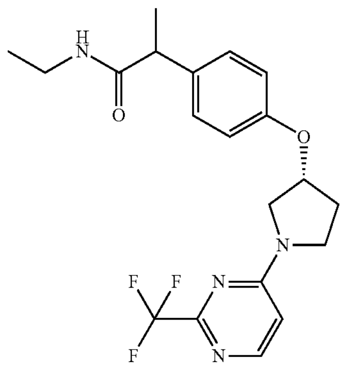 [SMILES: CCNC(=O)C(C)c1ccc(O[C@@H]2CCN(c3ccnc(C(F)(F)F)n3)C2)cc1] | 409 [M + H]$^+$ | 0.55 (I) |

Analytic Methods

Method A

| time (min) | Vol % water (incl. 0.1% NH$_3$) | Vol % MeOH |
|---|---|---|
| 0.00 | 95 | 5 |
| 0.05 | 95 | 5 |
| 1.40 | 0 | 100 |
| 1.80 | 0 | 100 |

Analytical column: XBridge C18 (Waters) 2.5 μm; 3.0×30 mm;
column temperature: 60° C.; flow: 2.2 ml/min.

Method B

| time (min) | Vol % water (incl. 0.1% TFA) | Vol % ACN | Flow [ml/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: Sunfire C18 (Waters) 2.5 μm; 3.0×30 mm;
column temperature: 60° C.

Method C

| time (min) | Vol % water (incl. 0.1% TFA) | Vol % MeOH |
|---|---|---|
| 0.00 | 95 | 5 |
| 0.05 | 95 | 5 |
| 1.40 | 0 | 100 |
| 1.80 | 0 | 100 |

Analytical column: Stablebond C18 (Waters) 1.8 μm; 3.0×30 mm; column temperature: 60° C.; flow: 2.2 ml/min.

Method D

| time (min) | Vol % water (incl. 0.1% NH$_3$) | Vol % MeOH | Flow [ml/min] |
|---|---|---|---|
| 0.00 | 95 | 5 | 2.2 |
| 0.30 | 95 | 5 | 2.2 |
| 1.50 | 0 | 100 | 2.2 |
| 1.55 | 0 | 100 | 2.9 |
| 1.70 | 0 | 100 | 2.9 |

Analytical column: XBridge C18 (Waters) 2.5 μm; 3.0×30 mm;
column temperature: 60° C.

Method E

| time (min) | Vol % water (incl. 0.1% NH$_3$) | Vol % ACN | Flow [ml/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: XBridge C18 (Waters) 2.5 μm; 3.0×30 mm;
column temperature: 60° C.

Method F

| time (min) | Vol % water (incl. 0.1% TFA) | Vol % ACN | Flow [ml/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stablebond C18 (Agilent) 1.8 μm; 3.0×30 mm;
column temperature: 60° C.

Method G

| time (min) | Vol % water (incl. 0.1% TFA) | Vol % MeOH (incl. 0.1% TFA) | Flow [ml/min] |
|---|---|---|---|
| 0.00 | 95 | 5 | 4.0 |
| 0.15 | 95 | 5 | 4.0 |
| 1.70 | 0 | 100 | 4.0 |
| 2.25 | 0 | 100 | 4.0 |

Analytical column: Sunfire C18 (Waters) 3.5 µm; 4.6×30 mm;
column temperature: 60° C.

Method H

| time (min) | Vol % water (incl. 0.1% TFA) | Vol % ACN |
|---|---|---|
| 0.00 | 98 | 2 |
| 1.50 | 0 | 100 |
| 1.80 | 0 | 100 |

Analytical column: Sunfire C18 (Waters) 3.5 µm; 4.6×30 mm;
column temperature: 60° C.; flow: 2.5 ml/min.

Method I

| time (min) | Vol % water (incl. 0.1% $NH_3$) | Vol % ACN (incl. 0.08% TFA) |
|---|---|---|
| 0.00 | 95 | 5 |
| 0.80 | 0.1 | 99.9 |
| 0.90 | 0.1 | 99.9 |

Analytical column: XBridge C18 (Waters) 1.7 µm; 3.0×30 mm;
column temperature: 60° C.; flow: 1.5 ml/min.

Method J

| time (min) | Vol % water (incl. 0.1% $NH_3$) | Vol % ACN |
|---|---|---|
| 0.00 | 98.0 | 2 |
| 1.20 | 0 | 100 |
| 1.40 | 0 | 100 |

Analytical column: XBridge C18 (Waters) 2.5 µm; 3.0×30 mm;
column temperature: 60° C.; flow: 2.0 ml/min.

Method K

| Time (min) | Vol % $CO_2$ | Vol % isopropanol (incl. 0.2% diethylamine) |
|---|---|---|
| 0.00 | 80 | 20 |
| 10.00 | 80 | 20 |

Analytical column: Daicel Chiralpak® AYH, 5 µm; 4.6×250 mm, flow: 4.0 ml/min

Method L

| Time (min) | Vol % $CO_2$ | Vol % EtOH (incl. 0.2% diethylamine) |
|---|---|---|
| 0.00 | 65 | 35 |
| 10.00 | 65 | 35 |

Analytical column: Daicel Chiralpak® AYH, 5 µm; 4.6×250 mm, flow: 4.0 ml/min

Method M

| Time (min) | Vol % $CO_2$ | Vol % MeOH (incl. 0.2% diethylamine) |
|---|---|---|
| 0.00 | 70 | 30 |
| 10.00 | 70 | 30 |

Analytical column: Daicel Chiralpak® AYH, 5 µm; 4.6×250 mm, flow: 4.0 ml/min

The invention claimed is:
1. A compound of the formula

$$(R^1)_n-Ar^1-N\underset{R^5}{\overset{O-Ar^2}{\diagdown}}\underset{O}{\overset{R^2}{\diagdown}}N\underset{R^4}{\overset{R^3}{\diagdown}},\quad (I)$$

wherein
$Ar^1$ is selected from the group consisting of: phenylene and 6-membered heteroarylene containing 1, 2 or 3 nitrogen atoms,
$R^1$ is selected from the group consisting of:
halogen, CN, OH, —$NO_2$, $C_{1-6}$-alkyl, $C_{2-4}$-alkenyl, $C_{3-7}$-cycloalkyl, —($C_{1-3}$-alkyl)-($C_{3-7}$-cycloalkyl), —O—($C_{1-6}$-alkyl), —O—($C_{3-7}$-cycloalkyl), —O—($C_{1-3}$-alkyl)-($C_{3-7}$-cycloalkyl), —$NH_2$, heterocyclyl, —($C_{1-3}$-alkyl)-heterocyclyl, —O-(heterocyclyl), —O—($C_{1-3}$-alkyl)-(heterocyclyl), —O-phenyl and —O—($C_{1-3}$-alkyl)-phenyl,
wherein each alkyl, cycloalkyl and heterocyclyl is optionally substituted with one or more substituents selected from F and OH;
wherein in the $NH_2$-group, one or both hydrogen atoms may independently of each other be replaced by a group selected from $C_{1-6}$-alkyl, $C_{3-7}$-cycloalkyl and —($C_{1-3}$-alkyl)-($C_{3-7}$-cycloalkyl),
wherein said $C_{1-6}$-alkyl, $C_{3-7}$-cycloalkyl and —($C_{1-3}$-alkyl)-($C_{3-7}$-cycloalkyl) groups may each be substituted by one or more F or OH, wherein said substituents are the same or different; and
wherein each heterocyclyl group is selected from a 4- to 7-membered monocyclic heterocyclic ring that contains 1, 2 or 3 hetereoatoms independently selected from N, O and S and may be substituted with one or more substituents independently of each other selected from methyl, —$CF_3$, F and OH, wherein, if two methyl groups are attached to the same carbon atom of the heterocyclyl group, they may be connected to each other to form a spirocyclopropyl group;
or, if two $R^1$-groups are attached to adjacent C-atoms of $Ar^1$, they may be linked with each other and together form a $C_{3-5}$-alkylene bridging group in which 1, 2 or 3

—CH$_2$-groups may independently of each be replaced by —O—, —C(=O)—, —S—, —S(=O)—, —S(=O)$_2$—, —NH— or —N(C$_{1-4}$-alkyl)-, wherein the alkylene bridge may optionally be substituted by one or two C$_{1-3}$-alkyl groups;

n is 1, 2 or 3;

Ar$^2$ is phenylene,
which is optionally substituted with F;

R$^2$ is selected from the group consisting of: H and C$_{1-4}$-alkyl optionally substituted with 1-3 F;

R$^3$ is selected from the group consisting of: H and C$_{1-4}$-alkyl;

R$^4$ is selected from the group consisting of:
C$_{1-6}$-alkyl, C$_{3-7}$-cycloalkyl, (C$_{3-7}$-cycloalkyl)-(C$_{1-3}$-alkyl)-, C$_{3-6}$-alkenyl, C$_{3-6}$-alkynyl, heterocyclyl, heterocyclyl-(C$_{1-3}$-alkyl)-, aryl, aryl-(C$_{1-3}$-alkyl)-, 5- or 6-membered heteroaryl containing 1, 2 or 3 heteroatoms independently selected from N, O and S and (5-membered heteroaryl)-(C$_{1-3}$-alkyl)-, wherein the heteroaryl moiety has 5 ring atoms and contains 1, 2 or 3 heteroatoms independently selected from N, O and S,
wherein each cycloalkyl and heterocyclyl may be optionally substituted with one or more C$_{1-4}$-alkyl, and
wherein in each cycloalkyl and heterocyclyl a —CH$_2$-group may optionally be replaced by —C(=O)—, and
wherein each alkyl, cycloalkyl and heterocyclyl may be optionally substituted with one or more groups independently selected from the group consisting of: F, Cl, Br, CN, OH and optionally mono- or polyfluorated —O—(C$_{1-4}$-alkyl), wherein the alkyl moiety of said —O—(C$_{1-3}$-alkyl) group may be substituted by one or more F, and
wherein each aryl and heteroaryl group may be optionally substituted with one or more substituents independently of each other selected from F, Cl, —O—CH$_3$, —O—CF$_3$, —O—CHF$_2$, CH$_3$ and —NH—C(=O)—(C$_{1-3}$-alkyl);

or R$^3$ and R$^4$ are connected with each other and together with the N-atom to which they are attached form a group selected from the group consisting of:
azetidinyl, pyrrolidinyl, piperidinyl and azepanyl,
wherein in each of these cyclic groups one or two CH$_2$-groups may independently of each other be replaced by N, O, S, C(=O) or SO$_2$, and/or
wherein each of these groups may be substituted by one or more F or C$_{1-4}$-alkyl; and R$^5$ is selected from the group consisting of H, F, Cl, CN and —O—(C$_{1-3}$-alkyl), wherein the alkyl moiety of the —O—(C$_{1-3}$-alkyl) group may be substituted by one or more F; and
wherein each of the above-mentioned alkyl and —O-alkyl groups may be substituted by one or more F;
or a tautomer or a salt thereof.

2. A compound of formula (I) according to claim 1, wherein
Ar$^2$ is

*—⟨phenylene⟩—*,

R$^2$ is —CH$_3$;
R$^3$ is H or —CH$_3$;
R$^5$ is H; and
n is 1 or 2.

3. A compound of formula (I) according to claim 1, wherein Ar$^1$ is selected from the group consisting of: phenylene, pyridinylene and pyrimidinylene.

4. A compound of formula (I) according to claim 1, wherein R$^1$ is selected from the group consisting of:
F, Cl, Br, CN, OH, C$_{1-4}$-alkyl, C$_{3-7}$-cycloalkyl, —O—(C$_{1-6}$-alkyl), —O—(C$_{3-7}$-cycloalkyl), —O—(C$_{1-3}$-alkyl)-(C$_{3-7}$-cycloalkyl), —NH$_2$, heterocyclyl, —O—(C$_{1-3}$-alkyl)-(heterocyclyl), —O-phenyl and —O—(CH$_2$)$_{1-2}$-phenyl,
wherein each alkyl, cycloalkyl and heterocyclyl is optionally substituted with one or more substituents selected from F and OH;
wherein in the NH$_2$-group, one or both hydrogen atoms may independently of each other be replaced by a group selected from C$_{1-6}$-alkyl and C$_{3-7}$-cycloalkyl, wherein said C$_{1-6}$-alkyl and C$_{3-7}$-cycloalkyl groups may each be substituted by one or more F or OH, wherein said substituents are the same or different; and
wherein each heterocyclyl group is selected from tetrahydrofuranyl, tetrahydropyranyl, pyrrolidinyl, piperidinyl, piperazinyl and morpholinyl and may be substituted with one or more F or OH;
or, if two R$^1$-groups are attached to adjacent C-atoms of Ar$^1$, they may be linked with each other and together form a C$_{3-5}$-alkylene bridging group in which 1, 2 or 3 —CH$_2$-groups may independently of each be replaced by —O—, —C(=O)—, —S—, —NH— or —N(C$_{1-4}$-alkyl)-, wherein the alkylene bridge may optionally be substituted by one or two C$_{1-3}$-alkyl groups.

5. A compound of formula (I) according to claim 1, wherein R$^1$ is selected from the group consisting of:
F, Cl, Br, CN, OH, C$_{1-3}$-alkyl, C$_{3-5}$-cycloalkyl, —O—(C$_{1-6}$-alkyl), —O—(C$_{3-7}$-cycloalkyl), —O—(C$_{1-3}$-alkyl)-(C$_{3-5}$-cycloalkyl), —NH$_2$, heterocyclyl, —O-phenyl and —O—(CH$_2$)$_{1-2}$-phenyl,
wherein each alkyl, cycloalkyl and heterocyclyl is optionally substituted with one or more substituents selected from F and OH;
wherein in the NH$_2$-group, one or both hydrogen atoms may independently of each other be replaced by a group selected from C$_{1-4}$-alkyl and C$_{3-5}$-cycloalkyl; and
wherein each heterocyclyl group is selected from pyrrolidinyl and morpholinyl and may be substituted with one or two F or OH;
or, if two R$^1$-groups are attached to adjacent C-atoms of Ar$^1$, they may be linked with each other and together form a —O—CH$_2$—CH$_2$—CH$_2$—O— group;
or, if n is 2, the second R$^1$ group is selected from the group consisting of F, Cl, CN, and CH$_3$.

6. A compound of formula (I) according to claim 1, wherein R$^4$ is selected from the group consisting of:
C$_{1-5}$-alkyl, C$_{3-5}$-cycloalkyl, (C$_{3-5}$-cycloalkyl)-CH$_2$—, C$_{3-5}$-alkenyl, C$_{3-5}$-alkynyl, heterocyclyl, heterocyclyl-(C$_{1-3}$-alkyl)-, phenyl, 6-membered heteroaryl containing 1 or 2 N atoms and thiazolyl-CH$_2$—,
wherein the heterocyclyl group is selected from the group consisting of oxetanyl, tetrahydrofuranyl and tetrahydropyranyl, and
wherein each cycloalkyl may be optionally substituted with one or two CH$_3$, and
wherein each alkyl and cycloalkyl may be optionally substituted with one or more groups independently selected from the group consisting of: F, Cl, CN, OH, —O—CHF$_2$, —O—CF$_3$ and —O—CH$_3$, and wherein the phenyl, thiazolyl and 6-membered heteroaryl groups may each be optionally substituted with one or two substituents inde-pendently of each other selected from F, Cl and —NH—C(=O)—CH$_3$.

7. A compound of formula (I) according to claim 1, wherein R$^3$ is H and R$^4$ is selected from the group consisting of:
C$_{1-5}$-alkyl optionally substituted with one to three F and/or one CN or OH;
C$_{3-5}$-cycloalkyl optionally substituted with one CH$_3$, wherein said CH$_3$-group may be substituted with one to three F;
(C$_{3-5}$-cycloalkyl)-CH$_2$— optionally substituted in the cycloalkyl moiety with one or two F;
C$_{3-5}$-alkenyl;
C$_{3-5}$-alkynyl;
oxetanyl, tetrahydrofuranyl, tetrahydropyranyl;
oxetanyl-CH$_2$—;
phenyl optionally substituted with F;
pyridinyl, pyrimidinyl and
thiazolyl-CH$_2$— optionally substituted with —NH—C(=O)—CH$_3$;
or the groups R$^3$ and R$^4$ may be connected with each other and together with the N-atom to which they are attached form the group

*—N⟨□⟩—F.

8. A compound according to claim 1 having the formula (I.2)

(R$^1$)$_n$—Ar$^1$—N⟨pyrrolidine⟩—O—⟨phenyl⟩—CH(CH$_3$)—C(=O)—N(R$^3$)(R$^4$)

wherein
n is 1 or 2;
Ar$^1$ is selected from the group consisting of:

[six aromatic ring structures: phenyl, pyridinyls, pyrimidinyl, pyridazinyl]

R$^1$ is selected from the group consisting of F, Cl, Br, CN, OH, C$_{1-3}$-alkyl, C$_{3-5}$-cycloalkyl, —O—(C$_{1-6}$-alkyl), —O—(C$_{3-7}$-cycloalkyl), —O—(C$_{1-3}$-alkyl)-(C$_{3-5}$-cycloalkyl), —NH$_2$, heterocyclyl, —O-phenyl and —O—(CH$_2$)$_{1-2}$-phenyl,
wherein each alkyl, cycloalkyl and heterocyclyl is optionally substituted with one or more substituents selected from F and OH;
wherein in the NH$_2$-group, one or both hydrogen atoms may independently of each other be replaced by a group selected from C$_{1-4}$-alkyl and C$_{3-5}$-cycloalkyl; and
wherein each heterocyclyl group is selected from pyrrolidinyl and morpholinyl and may be substituted with one or two F or OH;

or, if two R$^1$-groups are attached to adjacent C-atoms of Ar$^1$, they may be linked with each other and together form a —O—CH$_2$—CH$_2$—CH$_2$—O— group;
or, if n is 2, the second R$^1$ group is selected from the group consisting of F, Cl, CN, and CH$_3$;
R$^3$ is H or CH$_3$; and
R$^4$ is selected from the group consisting of:
C$_{1-5}$-alkyl optionally substituted with one to three F and/or one CN or OH;
C$_{3-5}$-cycloalkyl optionally substituted with one CH$_3$, wherein said CH$_3$-group may be substituted with one to three F;
(C$_{3-5}$-cycloalkyl)—CH$_2$— optionally substituted in the cycloalkyl moiety with one or two F;
C$_{3-5}$-alkenyl;
C$_{3-5}$-alkynyl;
oxetanyl, tetrahydrofuranyl, tetrahydropyranyl;
oxetanyl-CH$_2$—;
phenyl optionally substituted with F;
pyridinyl, pyrimidinyl and
thiazolyl-CH$_2$— optionally substituted with —NH—C(=O)—CH$_3$;
or R$^3$ and R$^4$ are connected with each other and together with the N-atom to which they are attached form the group

*—N⟨□⟩—F;

or a salt thereof.

9. A compound according to claim 1 having the formula (I.3)

(R$^1$)$_n$—Ar$^1$—N⟨pyrrolidine⟩—O—⟨phenyl⟩—CH(CH$_3$)—C(=O)—N(H)(R$^4$), wherein
the (R$^1$)$_n$—Ar$^1$— moiety is selected from a group consisint of:

[structures showing: 3-CF$_3$-phenyl; 4-F-3-CF$_3$-phenyl; 4-(propoxy)phenyl; 2-Cl-4-(propoxy)phenyl; 4-(cyclobutoxy)phenyl; 4-(cyclopentoxy)phenyl]

and
R⁴ is selected from the group consisting of:
ethyl, —CH₂—CHF₂, cyclopropyl and or a pharmaceutically acceptable salt thereof.

10. A compound according to claim 1 selected from the group consisting of:

or a pharmaceutically acceptable salt thereof.

11. A pharmaceutically acceptable salt of a compound according to claim 1.

12. A method of therapeutically treating obesity or type 2 diabetes which comprises administering to a host suffering from one of the said conditions a therapeutically effective amount of a compound according to claim 1.

13. A pharmaceutical composition comprising a compound according to claim 1 together with one or more inert carriers and/or diluents.

* * * * *